(12) United States Patent
Shirkhan et al.

(10) Patent No.: US 12,050,209 B2
(45) Date of Patent: *Jul. 30, 2024

(54) VACUUM LIQUID EXTRACTION AND PURIFICATION SYSTEMS AND METHODS

(71) Applicant: Fluid Management Systems, Inc., Billerica, MA (US)

(72) Inventors: Hamid Shirkhan, Manchester-by-the-Sea, MA (US); Dirk P. Ten Broeck, Nashua, NH (US); Joseph C. Caruso, Waltham, MA (US); Yijun Yang, Newton, MA (US); Rashid M. Juma, Pawtucket, RI (US); Thomas G. Hall, Nottingham, NH (US)

(73) Assignee: Fluid Management Systems, Inc., Billerica, MA (US)

( * ) Notice: Subject to any disclaimer, the term of this patent is extended or adjusted under 35 U.S.C. 154(b) by 731 days.

This patent is subject to a terminal disclaimer.

(21) Appl. No.: 17/178,985

(22) Filed: Feb. 18, 2021

(65) Prior Publication Data

US 2021/0181164 A1 Jun. 17, 2021

Related U.S. Application Data

(63) Continuation of application No. 15/998,756, filed on Aug. 15, 2018, now Pat. No. 10,955,392.

(60) Provisional application No. 62/625,799, filed on Feb. 2, 2018, provisional application No. 62/545,753, filed on Aug. 15, 2017.

(51) Int. Cl.
| | |
|---|---|
| *G01N 30/52* | (2006.01) |
| *A61M 39/10* | (2006.01) |
| *B01D 15/18* | (2006.01) |
| *B01D 15/22* | (2006.01) |
| *G01N 30/02* | (2006.01) |
| *G01N 30/46* | (2006.01) |
| *G01N 30/60* | (2006.01) |

(52) U.S. Cl.
CPC ............. *G01N 30/52* (2013.01); *A61M 39/10* (2013.01); *B01D 15/1871* (2013.01); *B01D 15/22* (2013.01); *G01N 30/465* (2013.01); *G01N 30/468* (2013.01); *G01N 30/6043* (2013.01); *G01N 30/6047* (2013.01); *B01D 2215/022* (2013.01); *G01N 2030/027* (2013.01); *G01N 2030/522* (2013.01)

(58) Field of Classification Search
None
See application file for complete search history.

(56) References Cited

U.S. PATENT DOCUMENTS

| | | |
|---|---|---|
| 3,199,274 A | 8/1965 | Norem et al. |
| 4,810,471 A | 3/1989 | Wachob et al. |
| 5,133,869 A | 7/1992 | Taniguchi et al. |
| 2009/0050548 A1 | 2/2009 | Shirkan |
| 2013/0306563 A1 | 11/2013 | Blaschyk |
| 2014/0166542 A1 | 6/2014 | Chawla |

*Primary Examiner* — P. Kathryn Wright

(57) ABSTRACT

The invention features compact systems and methods for vacuum liquid purification and extraction of a liquid sample.

19 Claims, 110 Drawing Sheets

STAGE 1

STAGE 2

SECTION VIEW

86

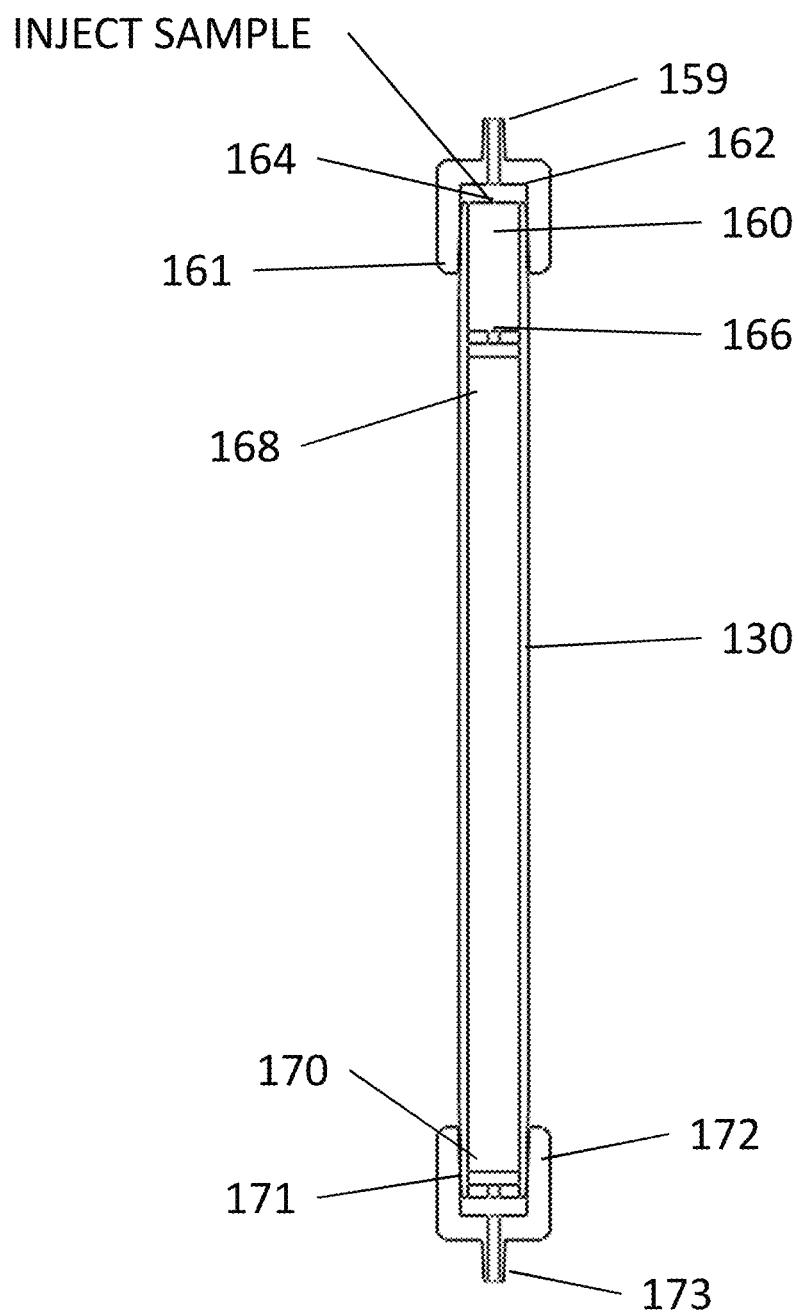

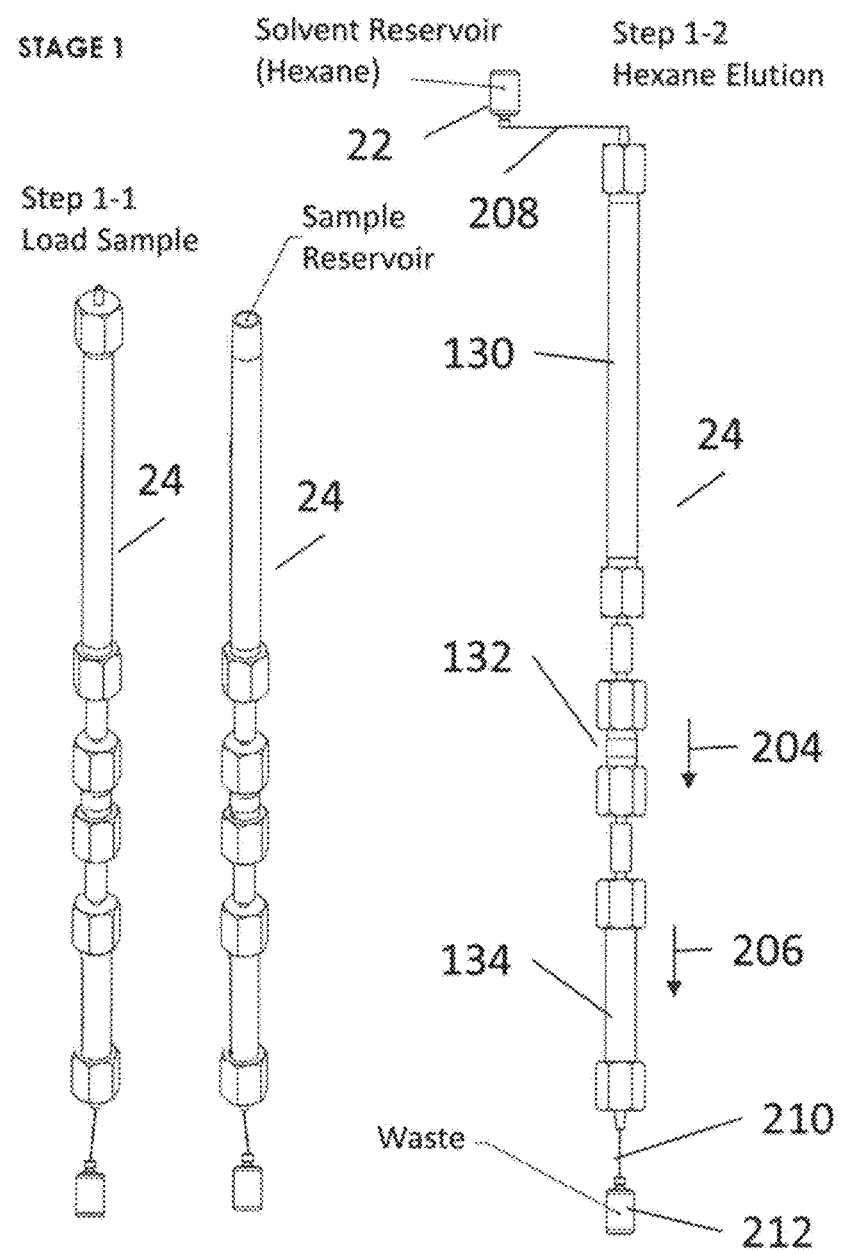

Stage 2

STEP 2-1
SAMPLE ELUTION

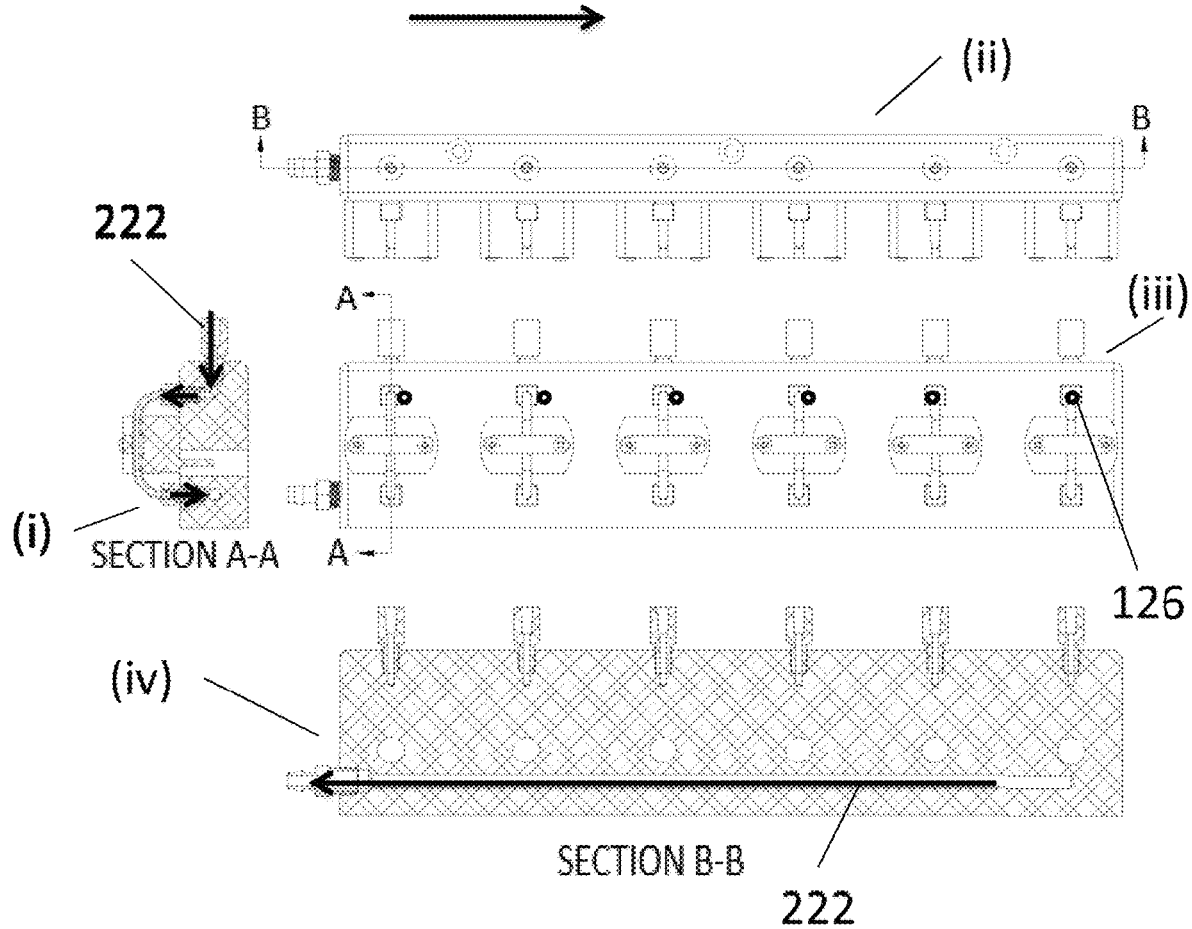

Stage 1 Manifold Transparent View

Arrow Shows
Flow Path

FIG. 14

Stage 1
Step 5
Columns-Reservoir
Installation & Connections
Arrow Represents
Tubing

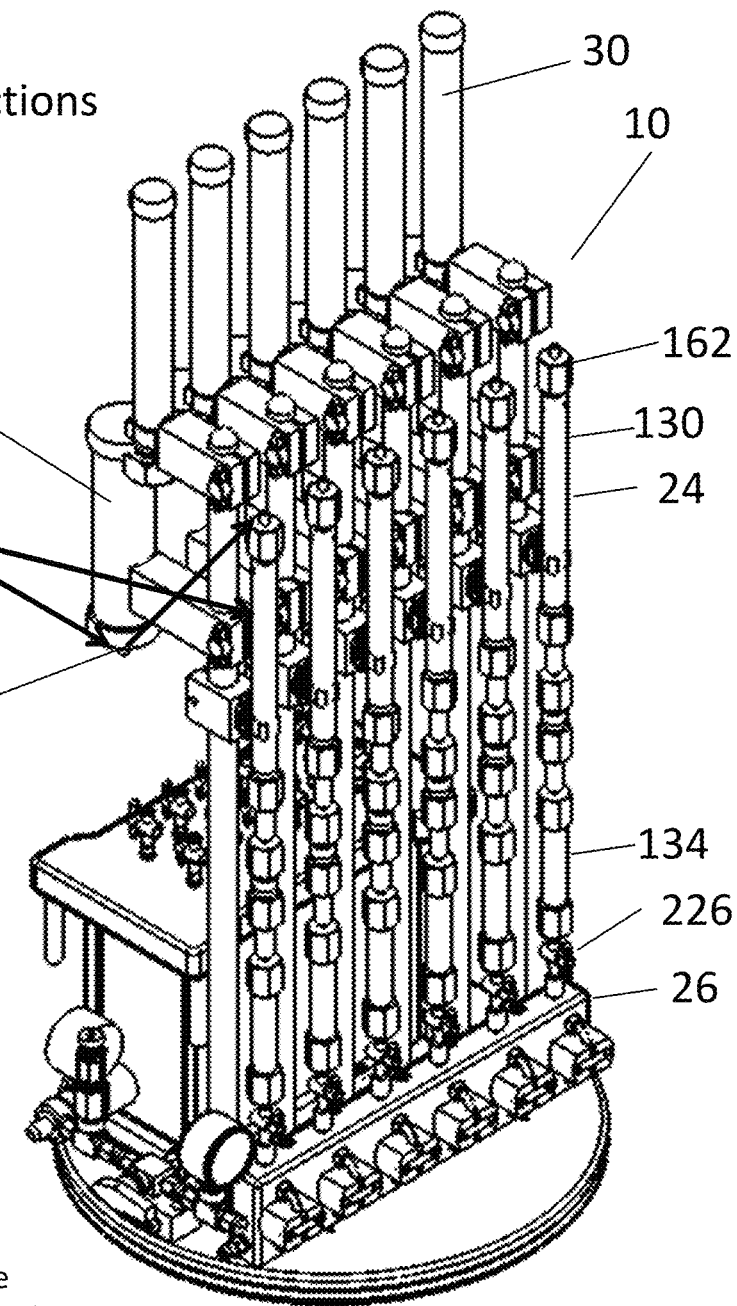

Connect the lines from each of the large Solvent Reservoirs to the top of each column

224

Install the Column Assembly (Alumina on the bottom).
Install the Luer Adapter of the Alumina Column to the Stopcock. Then push the Column Assembly onto the clip.
Install the Solvent Reservoirs by pushing each to the clips.

FIG. 15
Stage 1
Step 6
Condition Column

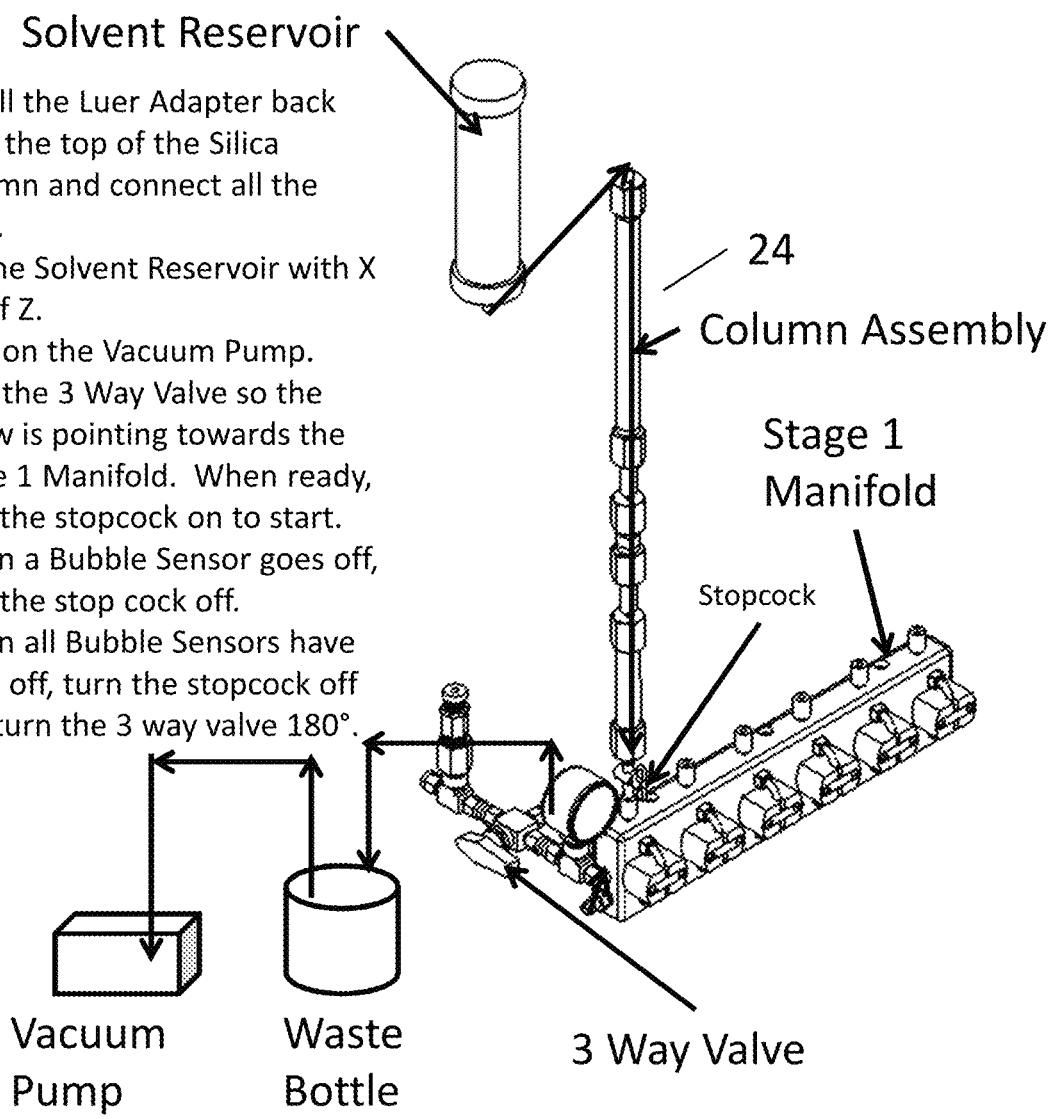

Arrow Shows Flow Path

Install the Luer Adapter back onto the top of the Silica Column and connect all the lines.
Fill the Solvent Reservoir with X mL of Z.
Turn on the Vacuum Pump.
Turn the 3 Way Valve so the arrow is pointing towards the Stage 1 Manifold. When ready, turn the stopcock on to start.
When a Bubble Sensor goes off, turn the stop cock off.
When all Bubble Sensors have gone off, turn the stopcock off and turn the 3 way valve 180°.

Stage 1
Step 7
Sample Injection

Disconnect the line from the Solvent Reservoir to the Column Assembly.
Remove the top Luer Adapter from the Silica Column.
Inject the sample into the Sample Reservoir of the Silica Column.

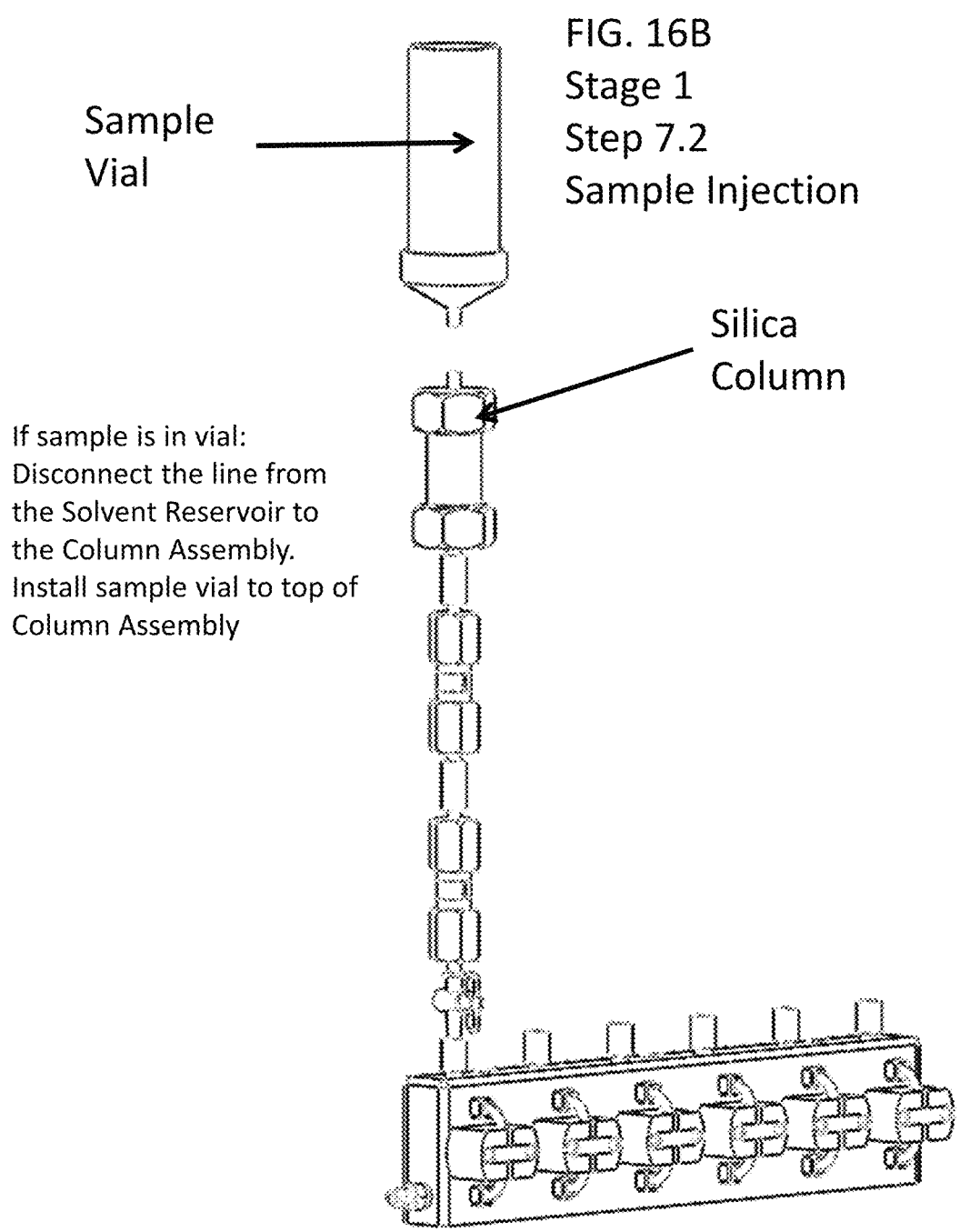

Stage 1
Step 8
Hexane Elution

Stage 2
Step 1
Column Disassembly

Remove the Columns. Disassemble the Column Assembly. Keep the Carbon and Alumina Columns

FIG. 19

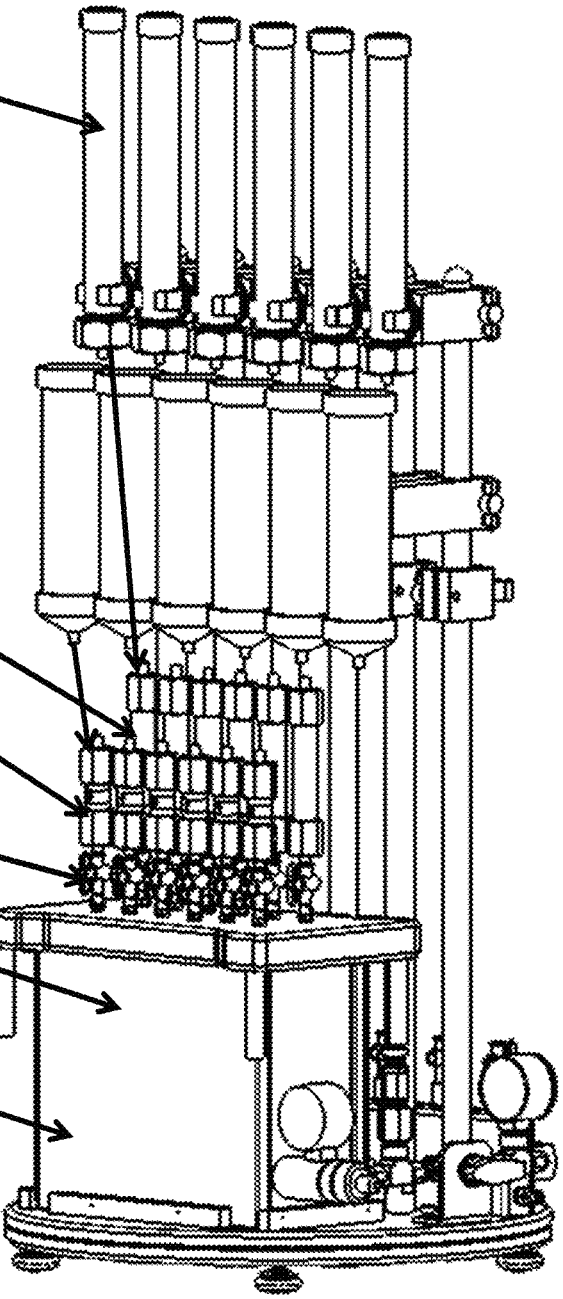

Stage 2
Step 2
Column Installation

Arrow Shows Flow Path →

Solvent Reservoir

Alumina Column

Carbon Column

Stopcock

Stage 2 Manifold

Sample Vial

Rotate the Turn Table 180°.
Remove the lid to the Stage 2 Manifold and install the Vial Rack and Sample Vials.
Flip each Carbon and Alumina Column upside down (arrow/text should be pointing down/upside down).
Install the Columns to the Stage 2 Manifold.
Connect the lines from the Solvent Reservoirs to each Column.

FIG. 20

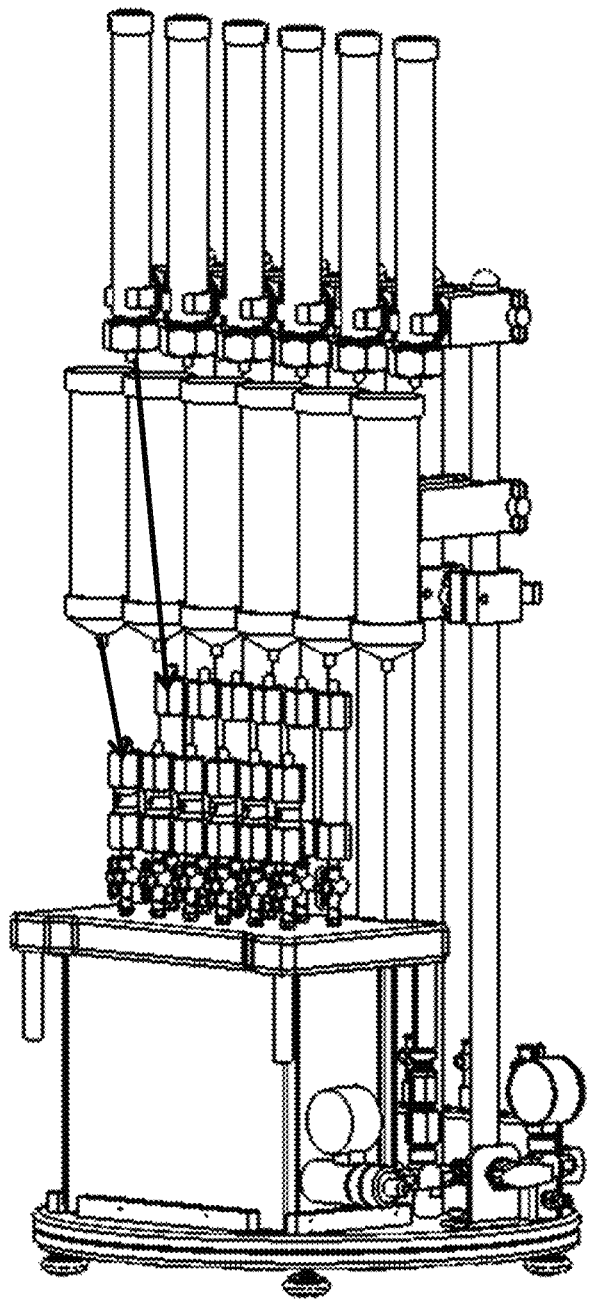

Stage 2
Step 3
Sample Elution

Arrow Shows Flow Path

Fill Solvent Reservoirs with X mL of Z.
Turn the 3 Way Valve so the arrow is pointing towards the Stage 2 Manifold.
Turn on the Vacuum Pump.
When Ready, turn the stopcock on to start Sample Elution.
When Solvent Reservoirs are empty, turn stopcock off.
When all samples are finished, turn off Vacuum Pump.
Evacuate the vacuum from the Stage 2 Manifold, remove lid, then remove Vials.

FIG. 21

STAGE 1 PROTOCOL

STEP 2: INSTALL COLUMN ONTO STAGE 1 MANIFOLD. PUSH COLUMN INTO CLIP, THEN SLIDE DOWN UNTIL COLUMN IS FIRMLY SECURED ONTO MANIFOLD.

STEP 3: CONNECT EACH SOLVENT RESERVOIR TO A COLUMN. FILL EACH SOLVENT RESERVOIR.

STEP 4: CONNECT 3 WAY VALVE ASSEMBLY TO WASTE BOTTLE. CONNECT WASTE BOTTLE TO VACUUM PUMP.

STEP 1: ASSEMBLE COLUMN.

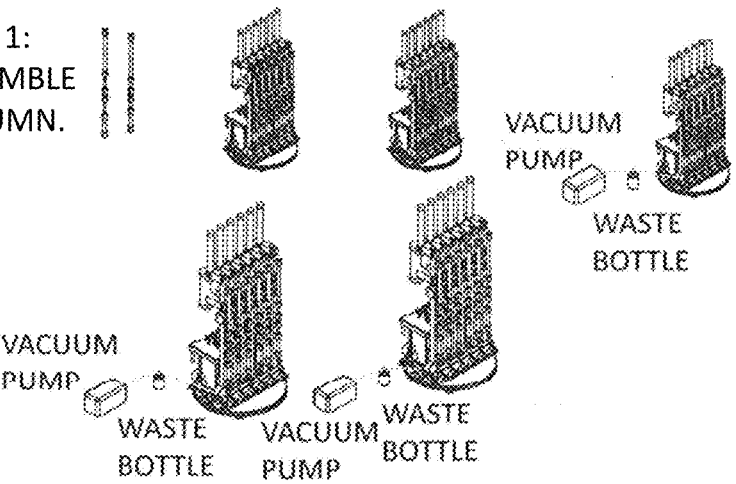

STEP 5: TURN 3 WAY VALVE SO VACUUM GOES TO STAGE 1 MANIFOLD.

STEP 6: TURN ON VACUUM PUMP AND LET SYSTEM RUN UNTIL ALL 6 SOLVENT RESERVOIRS ARE EMPTY. IF ANY COLUMNS FINISH EARLY, CLOSE OFF VALVE.

STEP 7: TURN OFF VACUUM PUMP. BLEED VACUUM IN STAGE 1 MANIFOLD BY TURNING 3 WAY VALVE. DISCONNECT SOLVENT RESERVOIR FROM COLUMN. MOVE ONTO STAGE 2.

FIG. 22

STAGE 2 PROTOCOL

STEP 1; REMOVE TOP COLUMN FROM COLUMN ASSEMBLY. DISASSEMBLE REMAINING COLUMNS.

STEP 2: ROTATE TURN TABLE 180°. FLIP EACH COLUMN UPSIDE DOWN AND INSTALL ONTO STAGE 2 MANIFOLD.

STEP 3: SWITCH 3 WAY VALVE TO DIRECT VACUUM TO STAGE 2 MANIFOLD. CONNECT EACH SOLVENT RESERVOIR TO EACH COLUMN AND FILL EACH RESERVOIR.

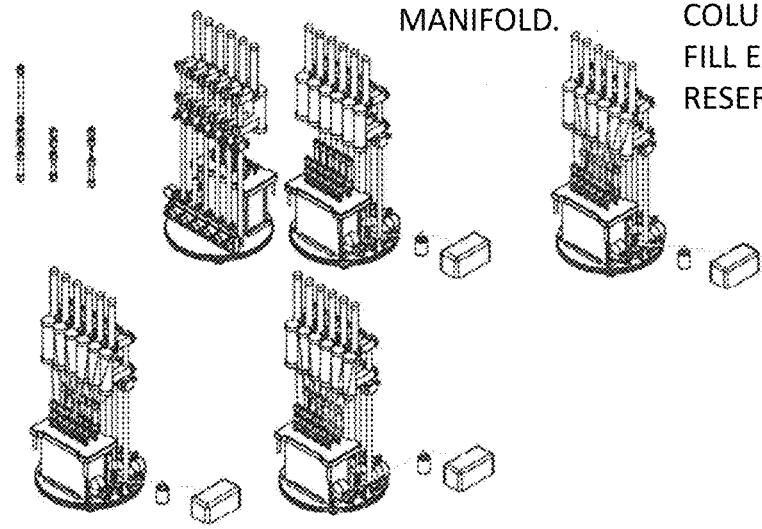

STEP 4: TURN ON VACUUM PUMP AND LET SYSTEM RUN UNTIL SAMPLES ARE IN COLLECTION TUBES.

STEP 5: ONCE ALL FIVE SAMPLES ARE IN COLLECTION TUBES, TURN ON VACUUM PUMP. EVACUATE VACUUM. REMOVE STAGE 2 MANIFOLD COVER. REMOVE COLLECTION VIALS.

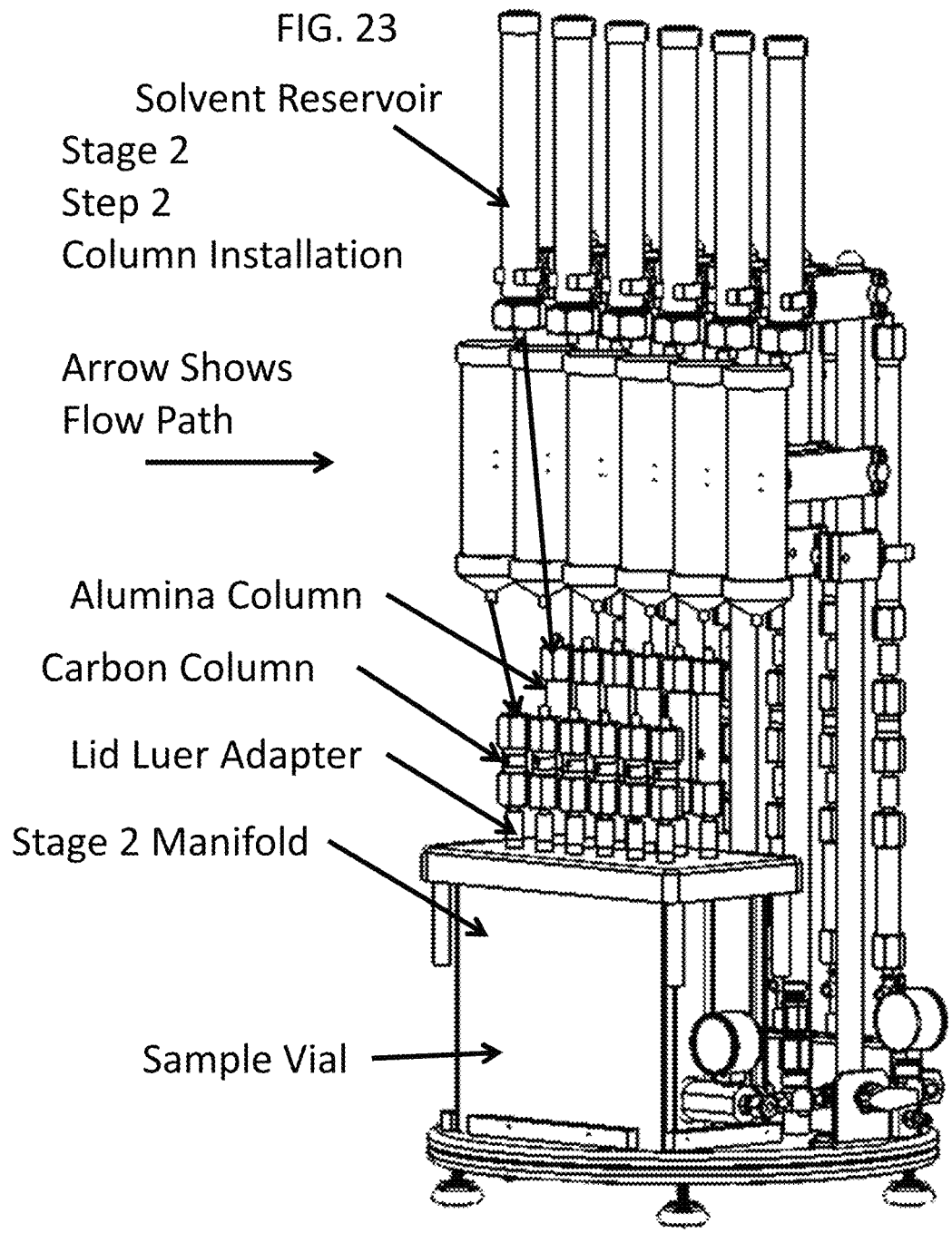

FIG. 23

Stage 2
Step 2
Column Installation

Arrow Shows Flow Path →

Labels: Solvent Reservoir, Alumina Column, Carbon Column, Lid Luer Adapter, Stage 2 Manifold, Sample Vial Rotate the Turn Table 180°
Remove the lid to the Stage 2 Manifold and install the Vial Rack and Sample Vials.
Flip each Carbon and Alumina Column upside down (arrow/text should be pointing down/upside down).
Install the Columns to the Stage 2 Manifold
Connect the lines from the Solvent Reservoirs to each Column.

FIG. 24

Stage 2
Step 3
Sample Elution

Arrow Shows
Flow Path

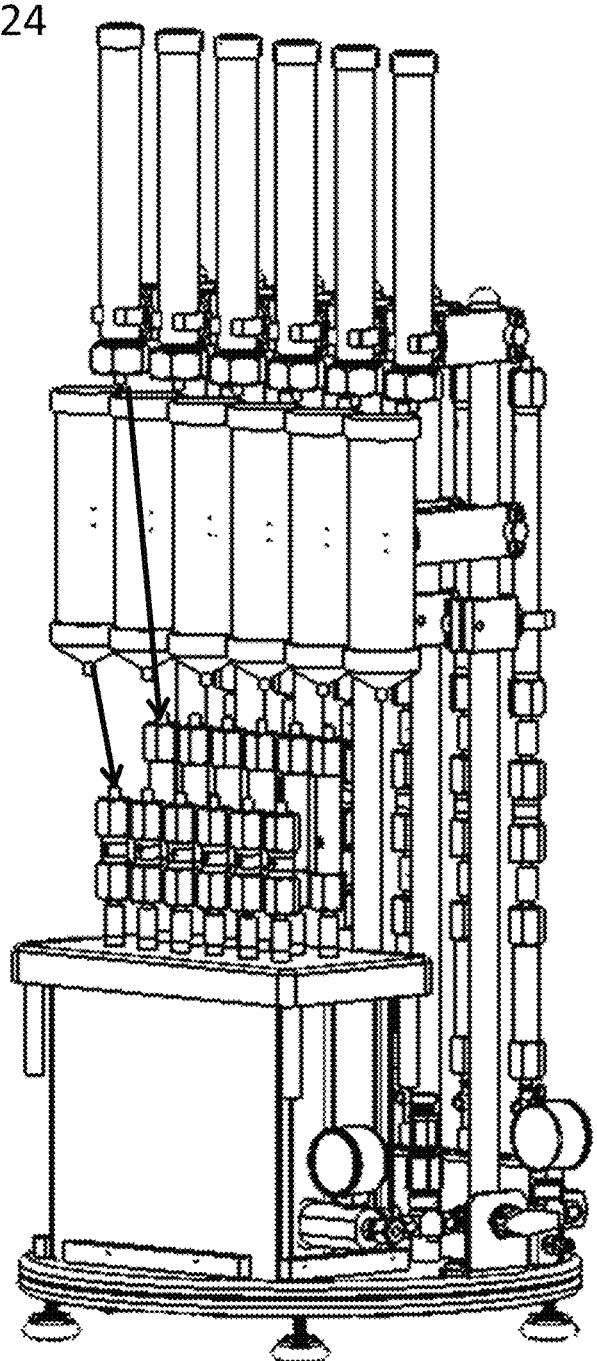

Fill Solvent Reservoirs with X mL of Z.
Turn the 3 Way Valve so the arrow is pointing towards the Stage 2 Manifold.
Turn on the Vacuum Pump.
When Ready, turn the stopcock on to start Sample Elution.
When Solvent Reservoirs are empty, turn stopcock off.
When all samples are finished, turn off Vacuum Pump.
Evacuate the vacuum from the Stage 2 Manifold, remove lid, then remove Vials.

Stage 2 Manifold Lid Luer Adapter

Stage 1

Stage 2

Exemplary Nominal Dimensions
Regular Sized Column
OD - 0.540"
ID – 0.369"
Jumbo Sized Column
OD – 0.875"
ID – 0.718"

Carbon and/or Alumina Columns of the column assembly of alternative embodiment B have a custom male luer (full taper) and female luer disposed on opposing ends. A washer disposed on each opposing end prevents the column from being repacked. Each washer is seated within a groove.

Jumbo Columns according to alternative embodiment B have a custom male and female luer disposed at opposing ends of the column. A washer disposed in a groove on each opposing end of the column prevents the column from being repacked.

Neutral/Basic Jumbo Silica columns of alternative embodiment B have a custom male luer on one end including a groove for a washer on the male luer end; and a custom Adapter press fit on the opposing end of the column for connection to the a Carbon column.

Adapter of alternative embodiment B is configured for press fit to bottom of a Neutral/Basic Jumbo Column for acting as a bottom washer.

Press Fit To Jumbo Column

Female Luer Connect to Male Luer of Carbon Column

Columns of alternative embodiments are configured for connection to one another via male and female luers machined into each column.

Jumbo columns of alternative embodiments are connected to one other via male and female luers machined into opposing ends of respective columns.

Column fitting to solvent reservoir according to alternative embodiment

Column Fitting To Stage 1 Manifold according to alternative embodiment

Stage 1 Manifold According to Embodiment A and Alternative Embodiment B:
Vacuum Relief Valve added to Stage 1 Manifold of Alternative Embodiment B allows user to adjust vacuum during Stage 1 operation to maintain optimal flow.

Vacuum Relief Valve

Large Solvent Reservoir Adapter of embodiment A and alternative embodiment B:
Adapter of alternative embodiment has a flat bottom port, such as, for a non-limiting example, a ¼-28 flat bottom port for secure attachment of tubing.
FIG. 47A
FIG. 47B
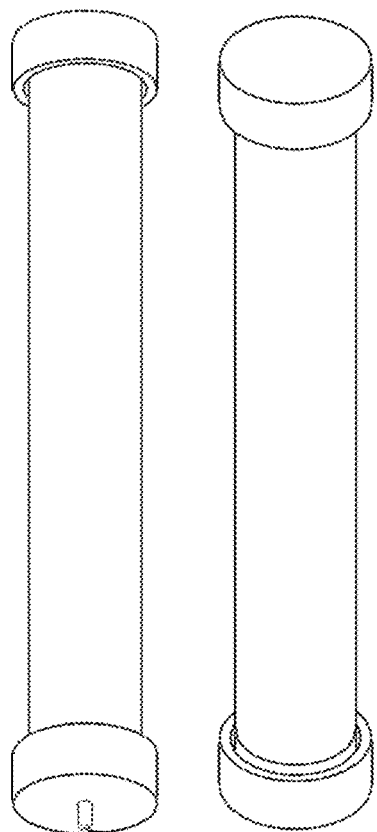
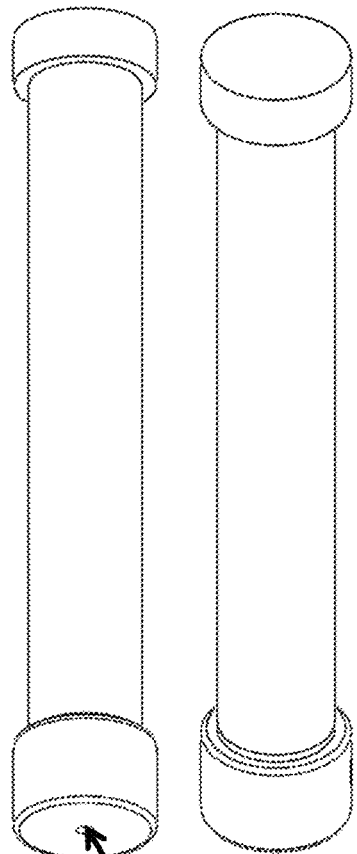
Male Luer
¼-28 Flat Bottom Port
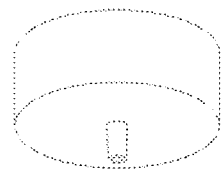
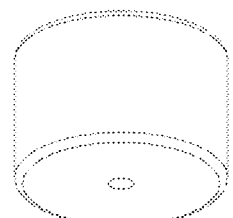

Small Solvent Reservoir Adapter of embodiment A and alterative embodiment B: Alternative embodiment adapter has a ¼-28 Flat Bottom Port for secure attachment of tubing.
FIG. 48A
FIG. 48B
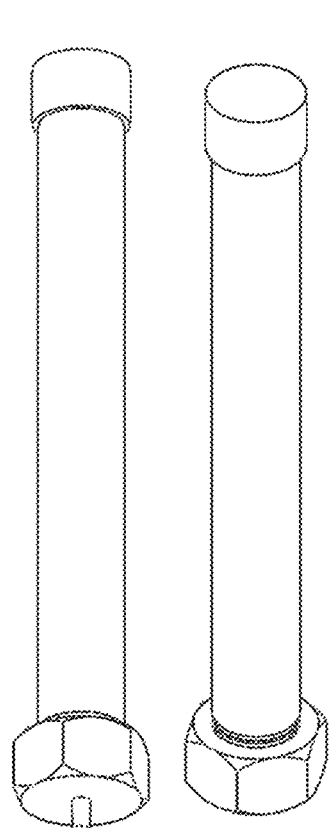
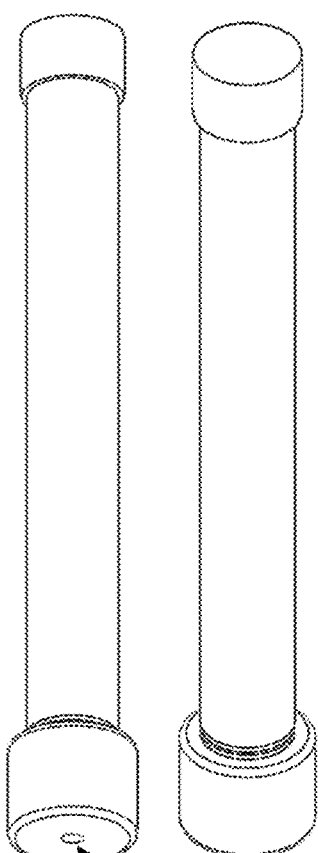
Male Luer
¼-28 Flat Bottom Port
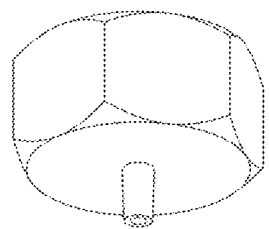
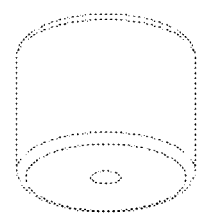

Large Reservoir Holder of embodiment A and alternative embodiment B:
Large Solvent Reservoir Holder of alternative embodiment B is attached to the Turn Table Rods by using a pass through hole in the Holder and is secured by thumb screws.
FIG. 49A
FIG. 49B
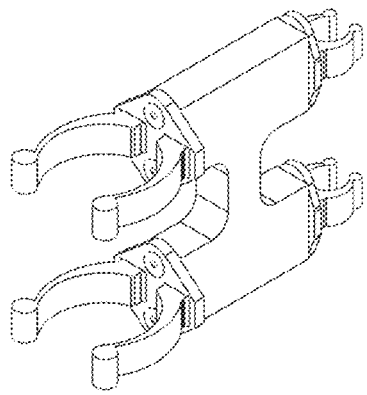
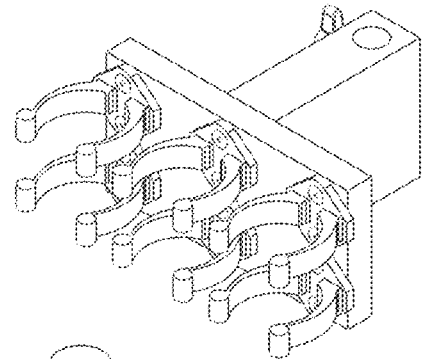
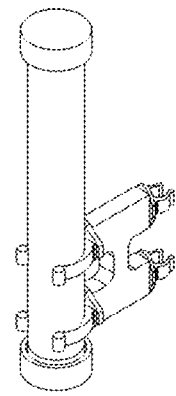
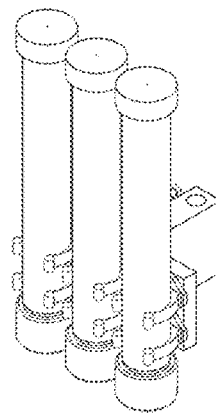
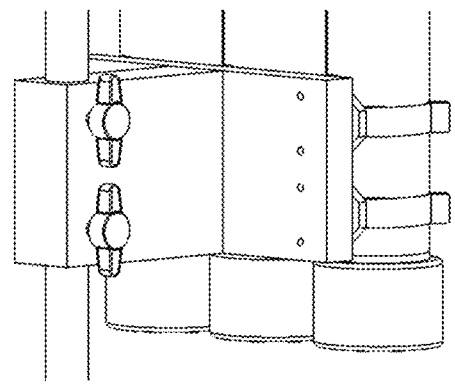

Alternative Embodiment
Large Reservoir Holder

Small Reservoir Holder
of embodiment A and alternative embodiment B:
Alternative embodiment Small Solvent Reservoir
Holder is attached to the Turn Table Rods by using the
pass through holes in the Holder and is secured by
thumb screws.
FIG. 51A          FIG. 51B
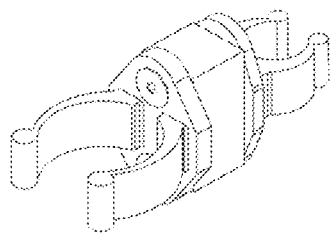
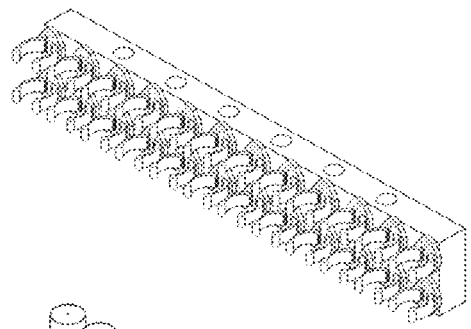
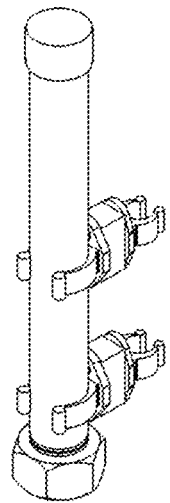
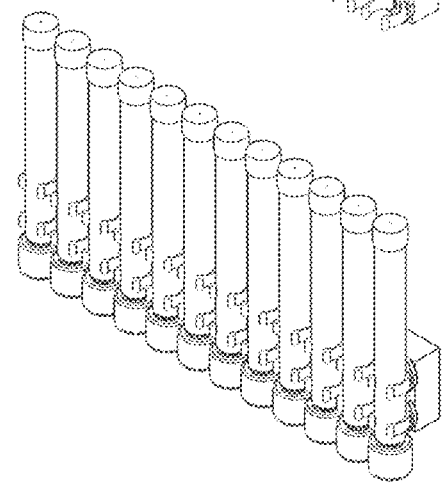
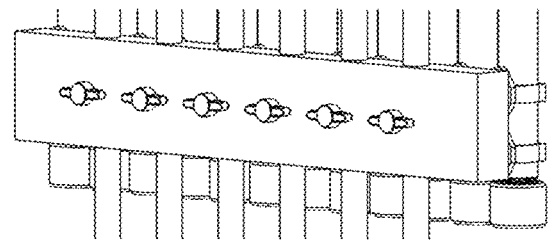

Small Reservoir Holder of alternative embodiment

Stage 2 Manifold of embodiment A and alternative embodiment B

Stage 2 Manifold Chamber
Of embodiment A and alternative
embodiment B: alternative embodiment
Stage 2 Manifold Chamber does not include
the Vacuum Adapter.

Vacuum Relief Valve

Vacuum Adapter

Fitting to 3 Way Valve

Vacuum Gauge

Stage 2 Manifold Lid
Of embodiment A and alternative embodiment B: Alternative embodiment Stage 2 Manifold Lid includes the Vacuum Adapter Stage 2 Manifold Column Connections of embodiment A include fittings for connection of columns to lid.

Stage 2 Manifold of alternative embodiment B is configured for direct connection of columns to lid without fittings.

3 Way Valve Bracket of embodiment A and alternative embodiment B
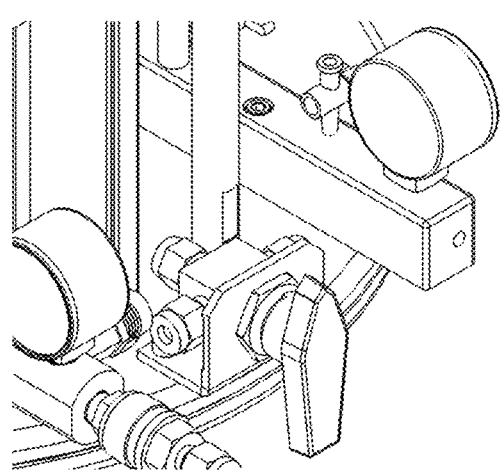
FIG. 58A
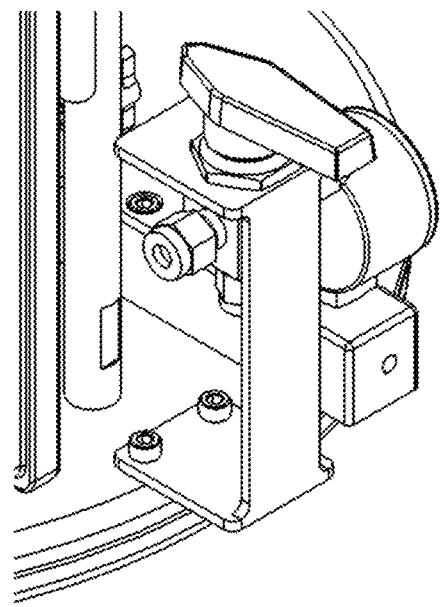
FIG. 58B
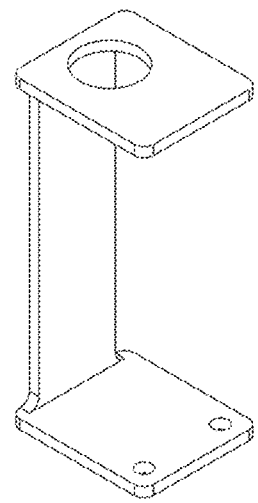

EZ-Prep SPE System uses the Stage 1 and Stage 2 Manifolds from the EZ-Prep System. This unit is for processing water samples.

Top View

Nitrogen Manifold

Stage 1 Manifold

Base Components

FIG. 63
Stage 1/Nitrogen Manifold
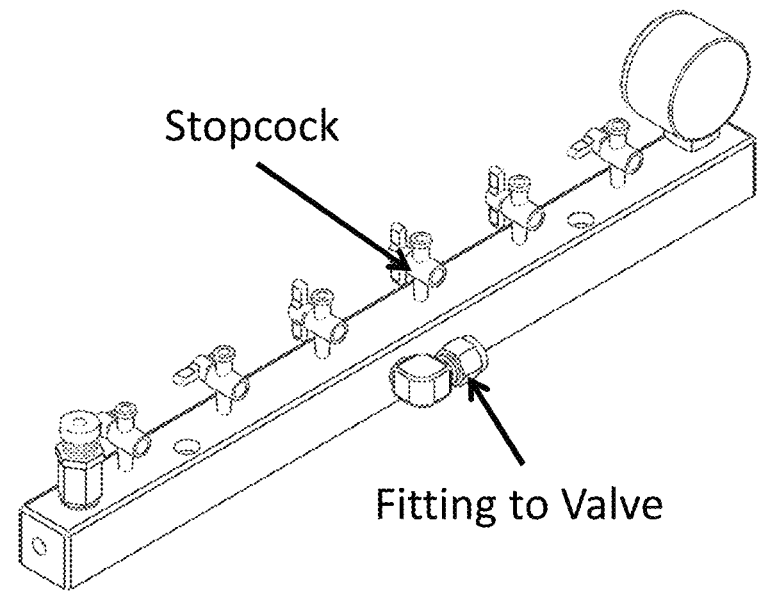
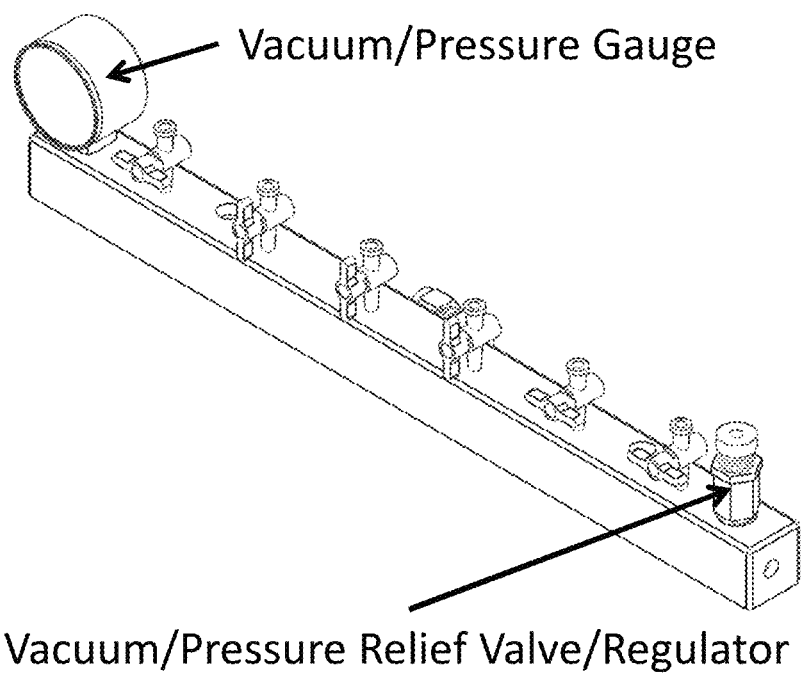

Stage 2 Manifold
Same manifold used in EZ-Prep

Column

Column having a fitting disposed on each opposing end for connection respectively to Stage 1 Manifold and to a sample bottle.

During Stage 1, connect the Columns to the Stage 1 Manifold. Then connect the Bottles to the Columns.

Stage 1 Drying: To dry the Columns, the columns are dried using a connection to a Nitrogen Manifold or with use of ambient air.

Stage 2 Sample elution: Column is connected to the Stage 2 Manifold, Syringe is connected to Column, and solvent is passed through column for elution.

NOT DRAWN TO SCALE

New EZprep Manifold

FMS Stackable Columns

Regular End caps

Regular Column

Lengths will vary depending on column type

Regular Column
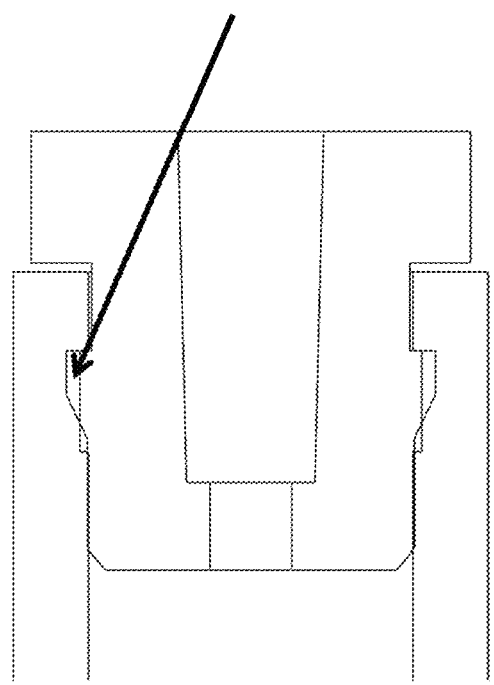
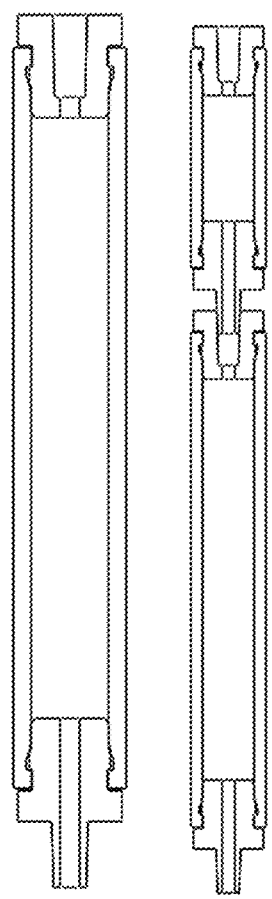
Groove/Shoulder holds End caps in place. Interference creates seal.
FIG. 80A    FIG. 80B   FIG. 80C Jumbo End caps Jumbo Column Retaining Groove Lengths will vary depending on column type FIG. 83B
Jumbo Column
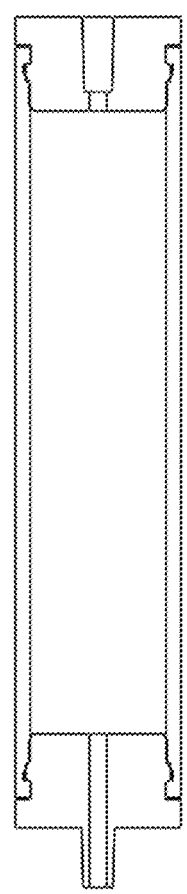
Groove/Shoulder holds
End caps in place.
Interference creates seal.
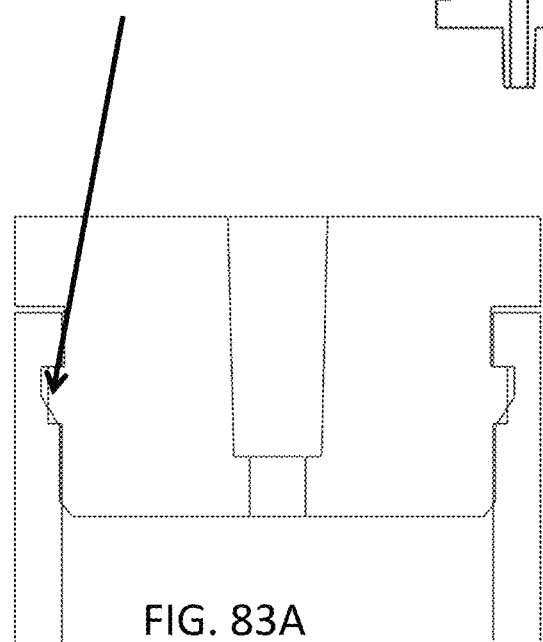
FIG. 83A
FIG. 83C FIG. 84A
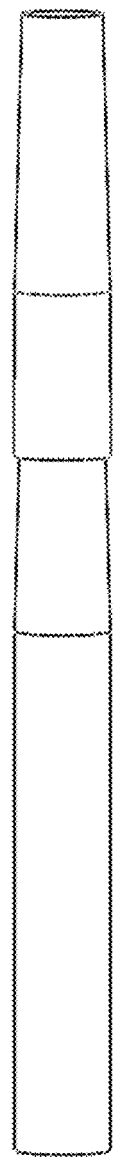
FIG. 84C
FIG. 84B
FIG. 84D

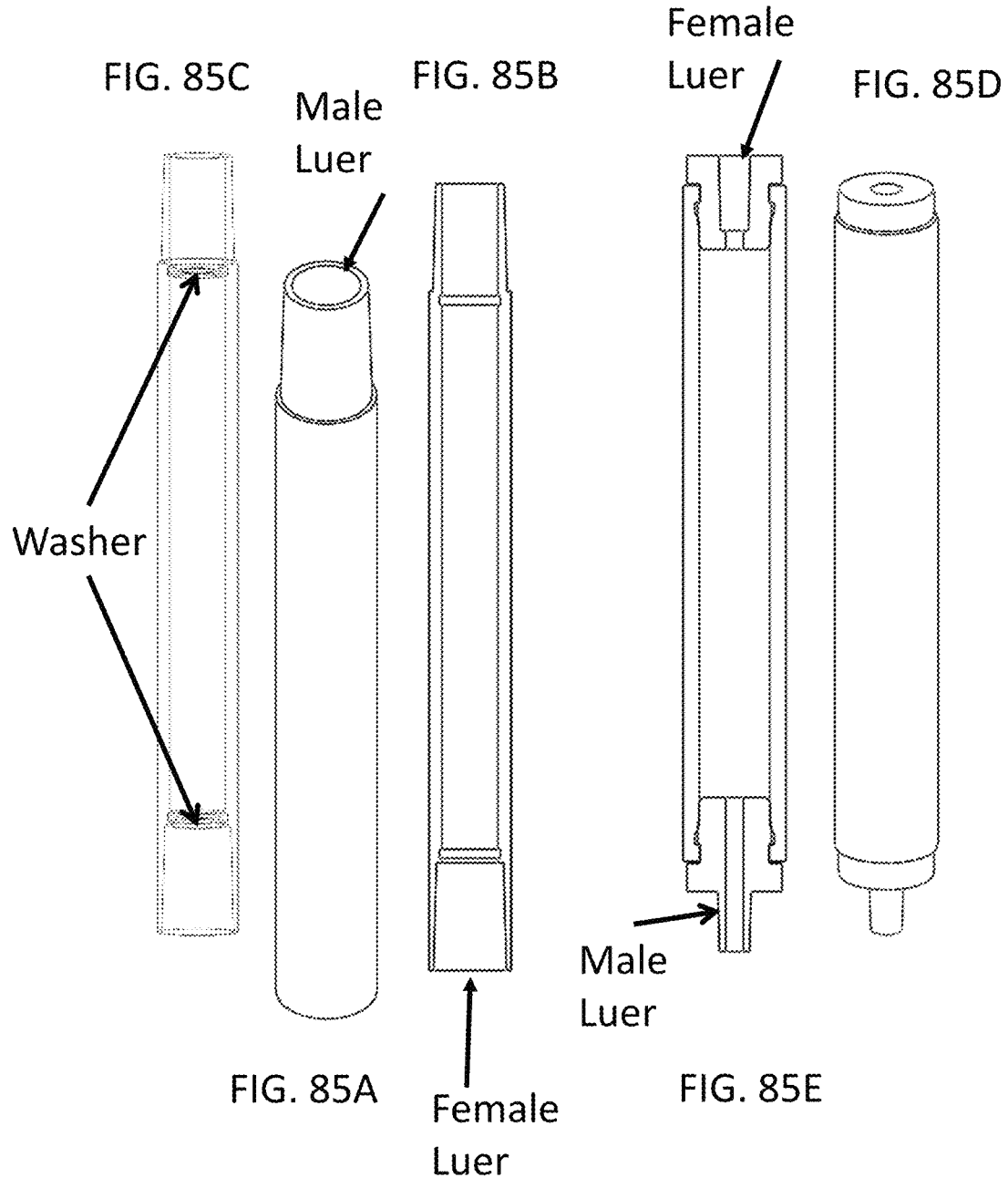

FIG. 87
Views not to scale
Perspective view
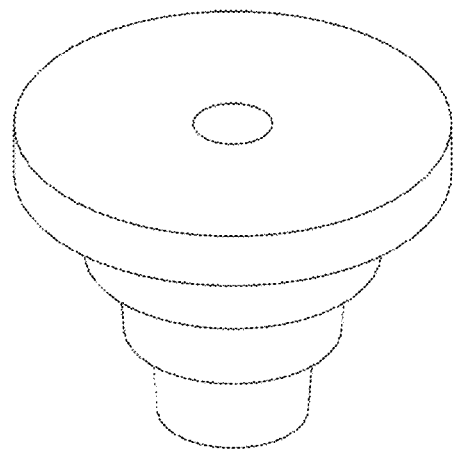
Sectional view
Female luer
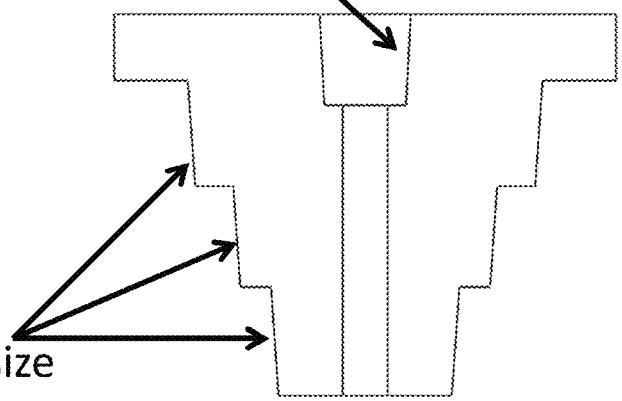
Fits difference size cartridges Views not to scale Views not to scale Perspective view    Sectional view FIG. 90
Views not to scale
Perspective views
Sectional views
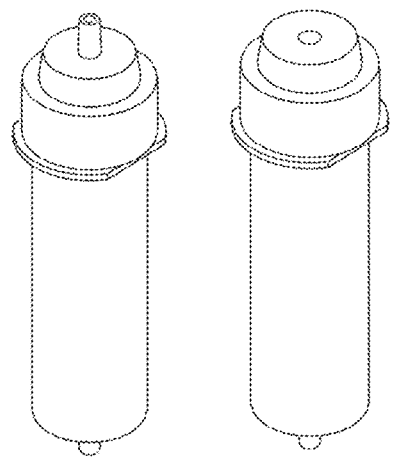
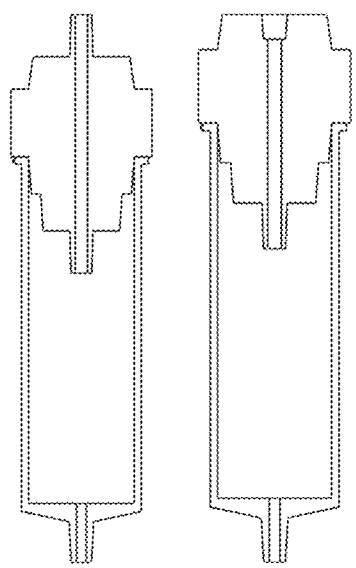

FIG. 91
Views not to scale
Perspective views
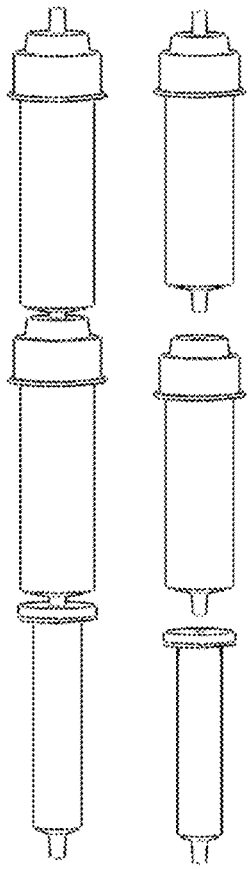
Sectional views
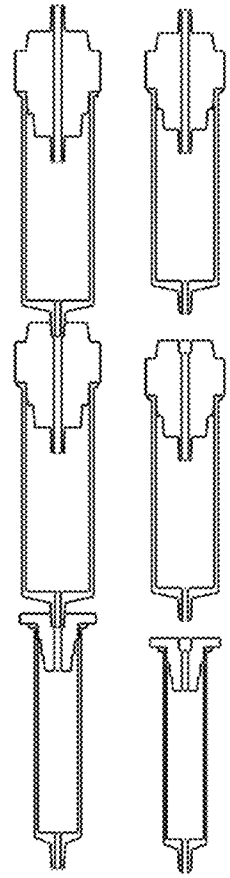

VACUUM LIQUID EXTRACTION AND PURIFICATION SYSTEMS AND METHODS

STATEMENT REGARDING FEDERALLY SPONSORED RESEARCH OR DEVELOPMENT

Not Applicable

BACKGROUND OF THE INVENTION

The present invention is related to the field of agro-products, pharmaceutical production and sample analysis. In the field of sample analysis, a large variety of studies are conducted in order to monitor for the presence of contaminants in food. In particular, toxins such as brominated and chlorinated pesticides, PCBs, and dioxins are extracted, purified and fractionated from pharmaceutical, environmental and biological samples. New and more stringent regulations regarding acceptable levels of these contaminants are continuously being adopted by the government or other regulatory agencies, driving the development of analytical systems that are more reliable and commercially practical in terms of cost and size. Important criteria in the development of such systems are the detection of more compounds, with lower detection limits, fast turn around and the ability to process a large number of samples efficiently.

Since chlorinated and brominated compounds are very toxic at sub-part per trillion (ppt) and part per quad trillion (ppqt) levels, the purification of these compounds becomes a difficult task in sample analysis. It is necessary, for example, to protect the sample from interfering compounds during the extraction, purification and fractionation processes. Interfering compounds can be introduced from the air and surrounding environment.

For example, it is required to detect some dioxins and polychlorinated biphenyls (PCBs) in low ppt level in food samples. However, the amount of PCBs in the air and other surroundings of laboratories may exceed the detection limits of the sample, so that the laboratories are unable to perform accurate testing. As a result, lab testing facilities are forced to construct new clean room labs with controlled environments. Therefore, testing for these highly toxic compounds in food is becoming very difficult, and few laboratories are able to perform this testing.

In the field of agro-products, extracted, purified and separated end products are obtained from spices, herbs, aromatic plants, and medicinal plants and are used for various end use applications such as cosmetics, flavors, medicines, perfumes, etc.

In the field of pharmaceutical production, compounds of interest are extracted, purified and separated for use in producing drugs and supplements. These processes are similar to those used in sample analysis, although they are usually carried out on a much larger scale to provide a desired amount of product.

For several years, new extraction techniques have emerged that exhibit advantages such as lower solvent consumption, automation and higher through put for processing solid and semi-solid samples such as food samples. The purification or "clean-up" step has also evolved to the use of entirely automated systems suitable for preparing a large number of samples.

Nevertheless, there is a continuing need for simpler, compact, semi-automated yet fast, efficient systems for performing high-quality sample analysis and pharmaceutical production.

BRIEF SUMMARY OF THE INVENTION

In accordance with the present invention, systems and methods are disclosed for vacuum liquid extraction, purification, fractionation and/or concentration (also referred to herein as extraction and purification") of aqueous and solid materials including water, waste water, serum, milk, food, environmental, biological agricultural and pharmaceutical samples containing trace substances that may be the subject of subsequent analysis or that may be used as an ingredient in a pharmaceutical product. The vacuum liquid extraction and purification system and method of the invention can be used, for example, in the extraction, fractionation, purification and/or concentration of a trace substance such as a pesticide, a chlorinated pesticide, a dioxin, a brominated compound, a polychlorinated biphenyl (PCB) and a polybrominated diphenyl ether (PBDE).

In one aspect, the invention features a vacuum system for purification of and extraction of at least one substance from a liquid sample. The system includes: a rotatable base for rotation between at least a first position and a second position; at least one assay column assembly having at least a first assay column and at least one second assay column; at least one Stage 1 solvent reservoir and having at least one easy connect fitting adapted for fluidic and reversible connection to the first assay column; at least one Stage 1 manifold mounted on a Stage 1 portion of the rotatable base and having at least one easy connect fitting adapted for fluidic and reversible connection with the second assay column; at least one Stage 2 reservoir and having at least one easy connect fitting adapted for fluidic and reversible connection with the second assay column; at least one Stage 2 manifold mounted on a Stage 2 portion of the rotatable base and having at least one easy connect fitting adapted for fluidic and reversible connection with the second assay column; wherein the first assay column has an easy connect fitting disposed at a first entry which is adapted for fluidic and reversible connection to the easy connect fitting of the Stage 1 solvent reservoir; wherein the first assay column has an easy connect fitting disposed at a first exit opposing the first entry of the first assay column which is adapted for fluidic and reversible connection to the second assay column; wherein the second assay column has an easy connect fitting disposed at a first entry of the second assay column which is adapted for fluidic and reversible selective alternate connection with the first assay column and the Stage 2 manifold; wherein the second assay column has an easy connect fitting disposed at a first exit opposing the first entry of the first assay column which is adapted for fluidic and reversible selective alternate connection with the Stage 1 manifold and the Stage 2 solvent reservoir, and optionally with a third assay column; and a vacuum pump adapted for selective fluidic coupling with the Stage 1 manifold and the Stage 2 manifold.

In one embodiment, the at least one liquid sample includes an organic solvent.

In another embodiment, the at least one easy connect fitting includes a female portion and a male portion at opposing ends of the easy connect fitting.

In another embodiment, the female portion includes a threaded female portion.

In another embodiment, the male portion includes a male luer.

In another embodiment, at least one easy connect fitting includes a union adapter including a female portion at opposing ends of the union adapter.

In one embodiment, at least one easy connect fitting includes a male portion machined into a body of a column at a first end of the column, and at least one easy connect fitting includes a female portion machined into the body of the column at an opposing second end of the column; where the column is selected from at least one of the first column, the second assay column and the third assay column.

In one embodiment, the system includes at least one frit being disposed at least one of a first end and an opposing second end of a column and a frit holder adjacent the frit and facing an interior of the column; where the column is selected from at least one of the first column, the second assay column and the third assay column.

In one embodiment, at least one of the first assay column, the second assay column, and the third assay column includes a column packing material selected for at least one of purification of and extraction from the liquid sample of the at least one substance selected from the group consisting of a pesticide, a chlorinated pesticide, a dioxin, a brominated compound, a polychlorinated biphenyl and a polybrominated diphenyl ether.

In one embodiment, the Stage 1 manifold includes a sensor for indicating at least one of a bubble.

In one embodiment, the system further includes the third assay column; wherein the third assay column has an easy connect fitting disposed at a first entry of third assay column which is adapted for fluidic and reversible selective alternate connection with the second assay column and the Stage 2 manifold; and wherein the third assay column has an easy connect fitting disposed at a first exit of the third assay column opposing the first entry of the third assay column which is adapted for fluidic and reversible selective alternate connection with the Stage 1 manifold and the Stage 2 solvent reservoir.

In one embodiment, at least one male luer is disposed in at least one opposing end of at least one of the first, the second and the third assay columns.

In one embodiment, at least one washer is disposed in a groove in a column body adjacent to the at least one male luer on an interior side of the assay column.

In one embodiment, at least one female luer is disposed in at least one opposing end of at least one of the first, the second and the third assay columns.

In one embodiment, at least one washer is disposed in a groove disposed adjacent to the female luer on an interior side of the assay column.

In one embodiment, the Stage 2 solvent reservoir includes a lid having a vacuum gauge and a vacuum regulator. In one embodiment, at least one of the first assay column, the second assay column and the third assay column comprises an at least one assay cartridge.

In another aspect the invention features a vacuum system for purification of and extraction of at least one substance from a liquid sample. The system includes at least one sample container for containing the liquid sample; a Stage 1 manifold; a drying gas manifold; a Stage 2 manifold; at least one assay column having an easy connect fitting disposed at a first end of the at least one assay column for fluidic and reversible selective alternate connection to the Stage 1 manifold and to the Stage 2 manifold, and an easy connect fitting disposed at an opposing second of the at least one assay column for fluidic and reversible selective alternate connection to the corresponding at least one fluid sample fluid container, the drying gas manifold and a Stage 2 solvent reservoir; and a vacuum pump for selective fluidic coupling with the Stage 1 manifold and the Stage 2 manifold.

In one embodiment, the vacuum system further includes at least one washing fluid container for containing a washing fluid for washing at least one of the sample container and the at least one assay column selectively before or after extraction;

In one embodiment, the at least one assay column includes an at least one assay cartridge.

Other aspects, features, and advantages of the present invention will be apparent from the Detailed Description that follows.

BRIEF DESCRIPTION OF THE SEVERAL VIEWS OF THE DRAWINGS

The invention will be more fully understood by reference to the following Detailed Description of the invention in conjunction with the Drawing, of which:

FIGS. 7A, 7B, 7C and 7D are respective sectional, elevation or side, exploded and perspective views of a first assay column for a liquid extraction and purification system in accordance with an embodiment of the invention;

FIGS. 11A and 11B are respective views of a Stage 1 configuration of an assay column assembly including three assay columns during sample loading and solvent elution, and a Stage 2 configuration of two assay columns during sample elution, in accordance with an embodiment of the invention;

FIG. 12A (i, ii iii, and iv) are respective sectional, plan or top, front elevation and sectional views of a Stage 1 manifold in accordance with an embodiment of the invention;

FIG. 14 is schematic representation of steps for installation of a Stage 1 configuration in accordance with an embodiment of the invention;

FIG. 15 is a schematic representation of steps for conditioning an assay column assembly in accordance with an embodiment of the invention;

FIG. 16B is a schematic representation of steps for introduction of a sample to liquid extraction and purification system in accordance with an embodiment of the invention;

FIG. 19 is a schematic representation of steps for Stage 2 assay column installation in accordance with an embodiment of the invention;

FIG. 20 is a schematic representation of steps for a Stage 2 sample elution in accordance with an embodiment of the invention;

FIG. 21 is a schematic representation of steps for a Stage 1 protocol or operational procedure in accordance with an embodiment of the invention;

FIG. 22 is a schematic representation of steps for a Stage 2 protocol or operational procedure in accordance with an embodiment of the invention, FIG. 23 is a schematic representation of steps for Stage 2 column installation in accordance with an embodiment of the invention;

FIG. 24 is a schematic representation of steps for a Stage 2 sample elution in accordance with an embodiment of the invention;

FIGS. 47A and 47B are perspective external views of Stage 1 or large solvent reservoir adapters in accordance with alternative embodiments of the invention;

FIGS. 48A and 48B are external perspective views of Stage 2 or small solvent reservoir adapters in accordance with alternative embodiments of the invention;

FIGS. 49A and 49B are external perspective views of large reservoir holders, in accordance with alternative embodiments of the invention;

FIGS. 51A and 51B are perspective views of small reservoir holders in accordance with alternative embodiments of the invention;

FIGS. 58A and 58B are views of three-way valve brackets, in accordance with alternative embodiments of the invention;

FIG. 63 includes schematics of Stage 1 or Drying Gas or Nitrogen Manifolds of a Solids Phase Extraction system, in accordance with embodiments of the invention;

FIGS. 80A, 80B, and 80C are schematics of sectional views of respective assay column end caps for a regularly-sized assay column, in accordance with an embodiment of the invention;

FIGS. 83A, 83B, and 83C are schematics of sectional views of respective assay column end caps for a jumbo-sized assay column, in accordance with an embodiment of the invention;

FIGS. 84A, 84B, 84C and 84D are schematics of respective external, sectional, perspective and sectional views of assay columns including respective alternative column end configurations, in accordance with alternative embodiments of the invention;

FIGS. 85A, 85B, 85C, 85D, and 85E are schematics of corresponding perspective, sectional, perspective sectional, perspective and sectional views of assay columns, in accordance with alternative embodiments of the invention;

FIG. 87 includes perspective and sectional views of an assay cartridge fitting, in accordance with an embodiment of the invention;

FIG. 90 includes perspective and sectional views of an assay cartridge including fittings in accordance with an embodiment of the invention; and FIG. 9I includes perspective and exploded assay cartridge assemblies including fittings in accordance with embodiments of the invention.

DETAILED DESCRIPTION OF THE INVENTION

The present application claims priority to US Prov. Appln. Nos. 62/545,753 and 62/625,799 filed respectively on Aug. 15, 2017 and Feb. 2, 2018, the disclosures of which are herein incorporated by reference. The invention features compact vacuum systems and methods for liquid or fluid extraction and/or purification of pollutants, contaminants, and/or other undesired substances. Throughout the present application the terms "liquid or liquids" are used interchangeably with the respect terms "fluid or fluids". In one aspect, the vacuum systems and methods of the invention can be used for the purification of liquid samples. In a preferred embodiment, the liquid samples include organic solvent samples. In another aspect, the vacuum systems and methods can be used for the extraction of fluid samples. In a preferred embodiment, the extraction can include solid phase extraction. Throughout the present application, the terms "solid phase extraction" and "SPE" are interchangeably. In another preferred embodiment, the vacuum systems and methods can be used for the extraction of fluid samples including water, milk, blood and/or serum. Assay chromatography columns are equipped with quick connect/disconnect fittings on a movement device such as a rotating base. The invention features easy installation, detachment and flexibility. The assay columns can be used in different configurations within the same system, and can be further reused or discarded, as necessary. The assay columns can be reused, conditioned, stored, and/or disposed after use. The systems and methods of the invention are discussed below in the context of the figures. The same numbering is generally used to the extent possible for components which can appear in more than one figure.

Figure 1A:
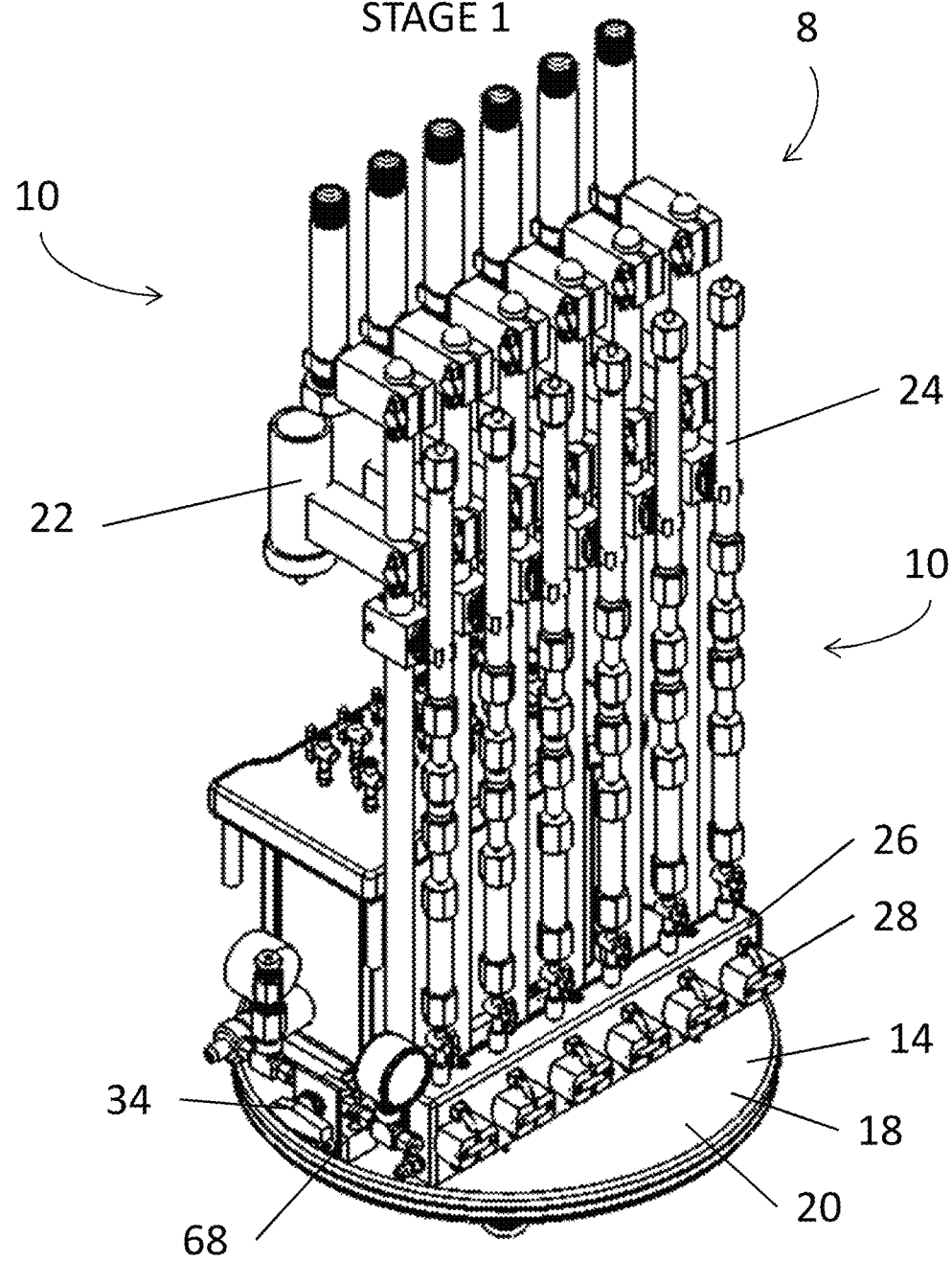
FIGS. 1A and 1B are perspective views of a respective Stage 1 and Stage 2 configuration of components for a liquid extraction and purification system in accordance with an embodiment of the invention.
Figure 1B:
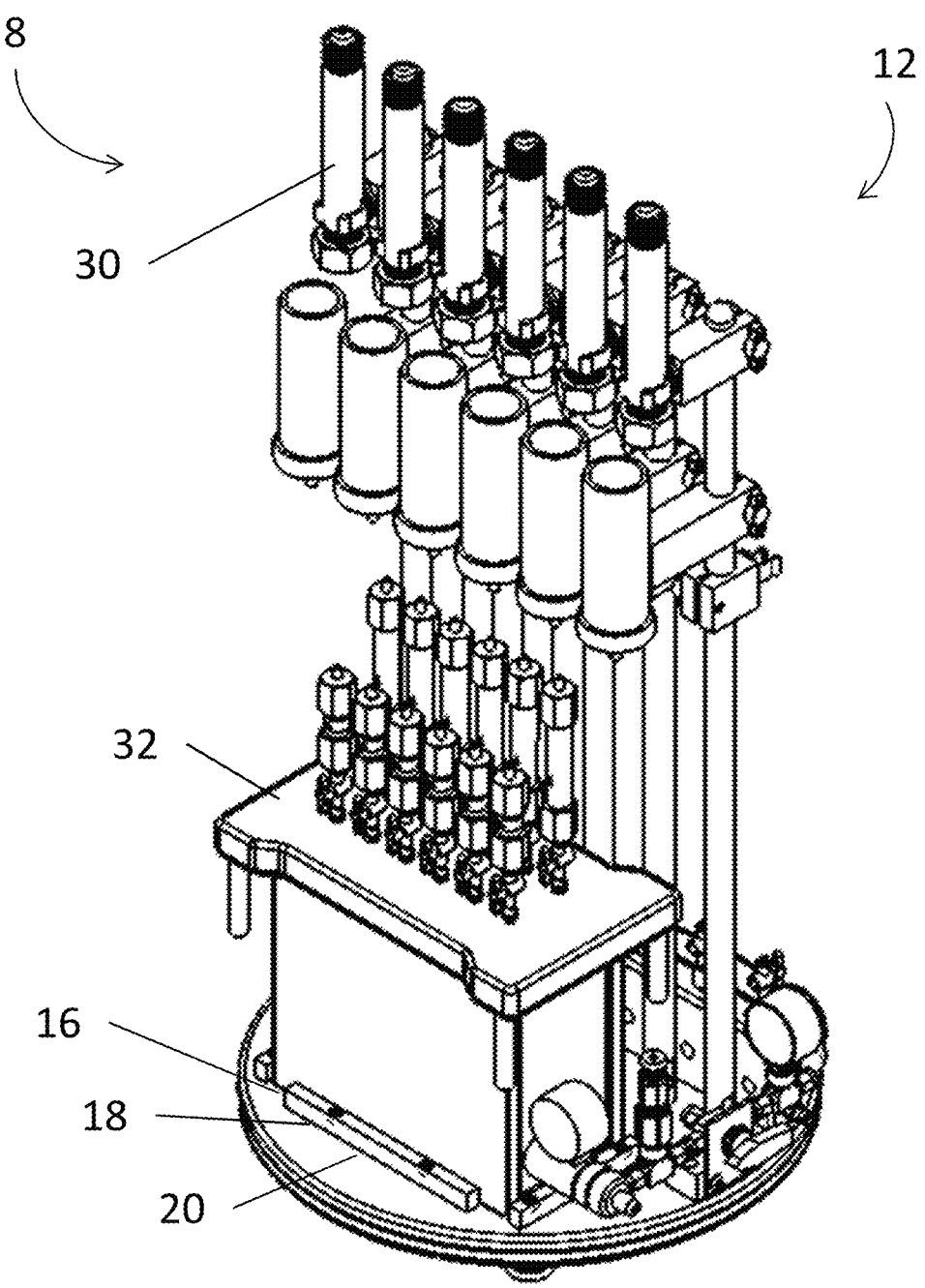

FIGS. 1A and 1B show respectively perspective views of a Stage 1 (10) and a Stage 2 (12) configuration or set-up of components for a vacuum liquid extraction and purification system (8) that can be used to test a variety of solid and semi-solid samples for the presence of any of a number of trace substances. In one aspect, the Stage 1 (10) and Stage 2 (12) configuration of components is used for the purification of and/or extraction of a substance from a liquid sample. In a preferred embodiment, the liquid sample includes an organic solvent sample. The Stage 1 configuration (10) and the Stage 2 configuration (12) are disposed respectively on a Stage 1 portion (14) and a Stage 2 portion (16) of a movement device (18) including for a non-limiting example, a rotating base (20), such as a turn-table. The Stage 1 configuration (10) includes one or more Stage 1 solvent reservoir(s) (22). Each Stage 1 reservoir is adapted for fluidic and reversible connection with a corresponding assay column assembly (24) which in turn is adapted for fluidic and reversible connection to a Stage 1 manifold(s) (26). The Stage 1 manifold (26) can include a one or more Stage 1 manifold sensor(s) (28) each corresponding to a respective assay column assembly (24). The Stage 2 configuration includes one or more Stage 2 solvent reservoir(s) (30). Each stage 2 reservoir (30) is adapted for fluidic and reversible connection to an assay column (not shown as connected here) which in turn is adapted for fluidic and reversible connection to a Stage 2 manifold (32).

Figure 2A:
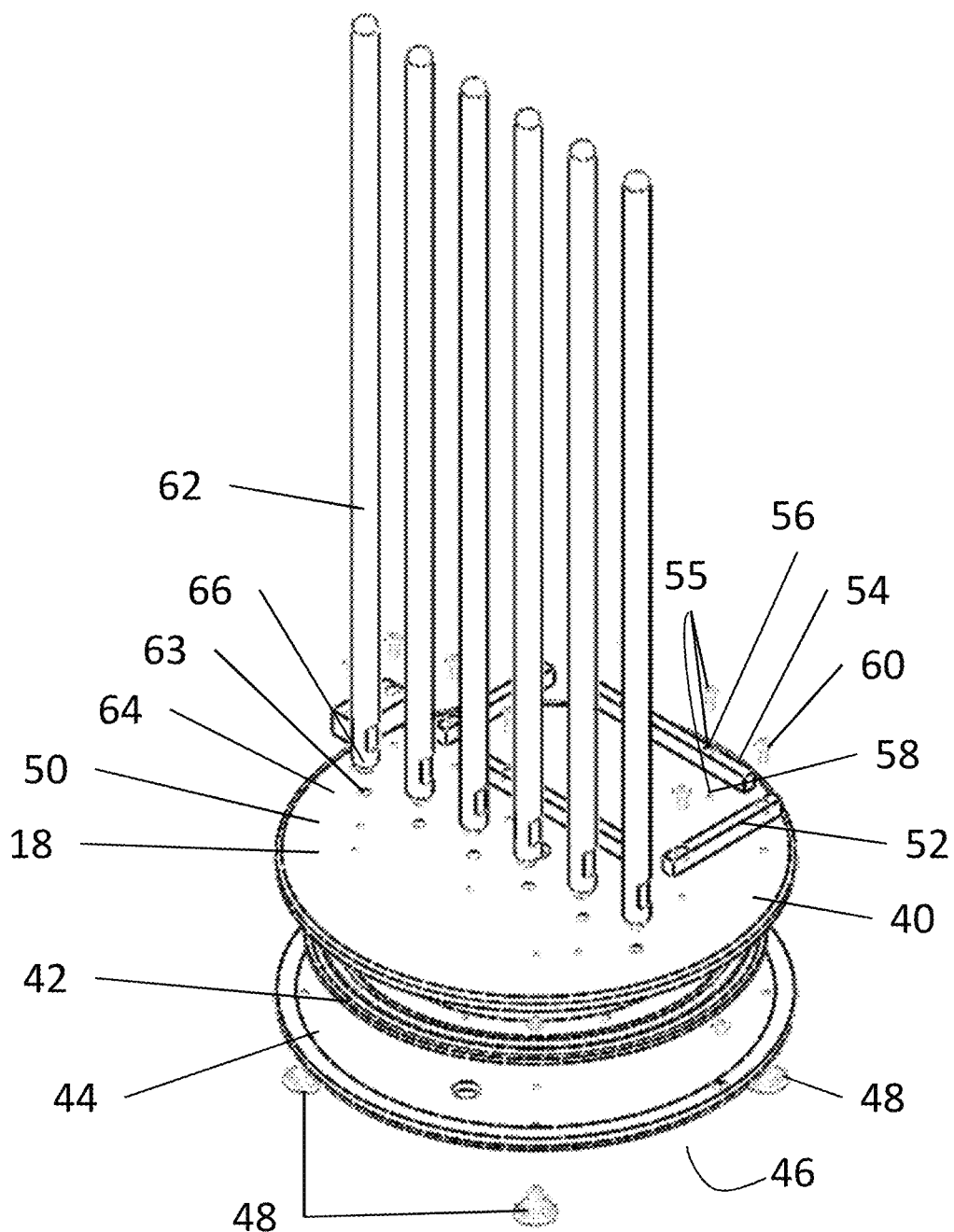
FIGS. 2A and 2B are respective perspective exploded and assembled views of the movement device and supporting mechanisms for a liquid extraction and purification system in accordance with an embodiment of the invention.
Figure 2B:
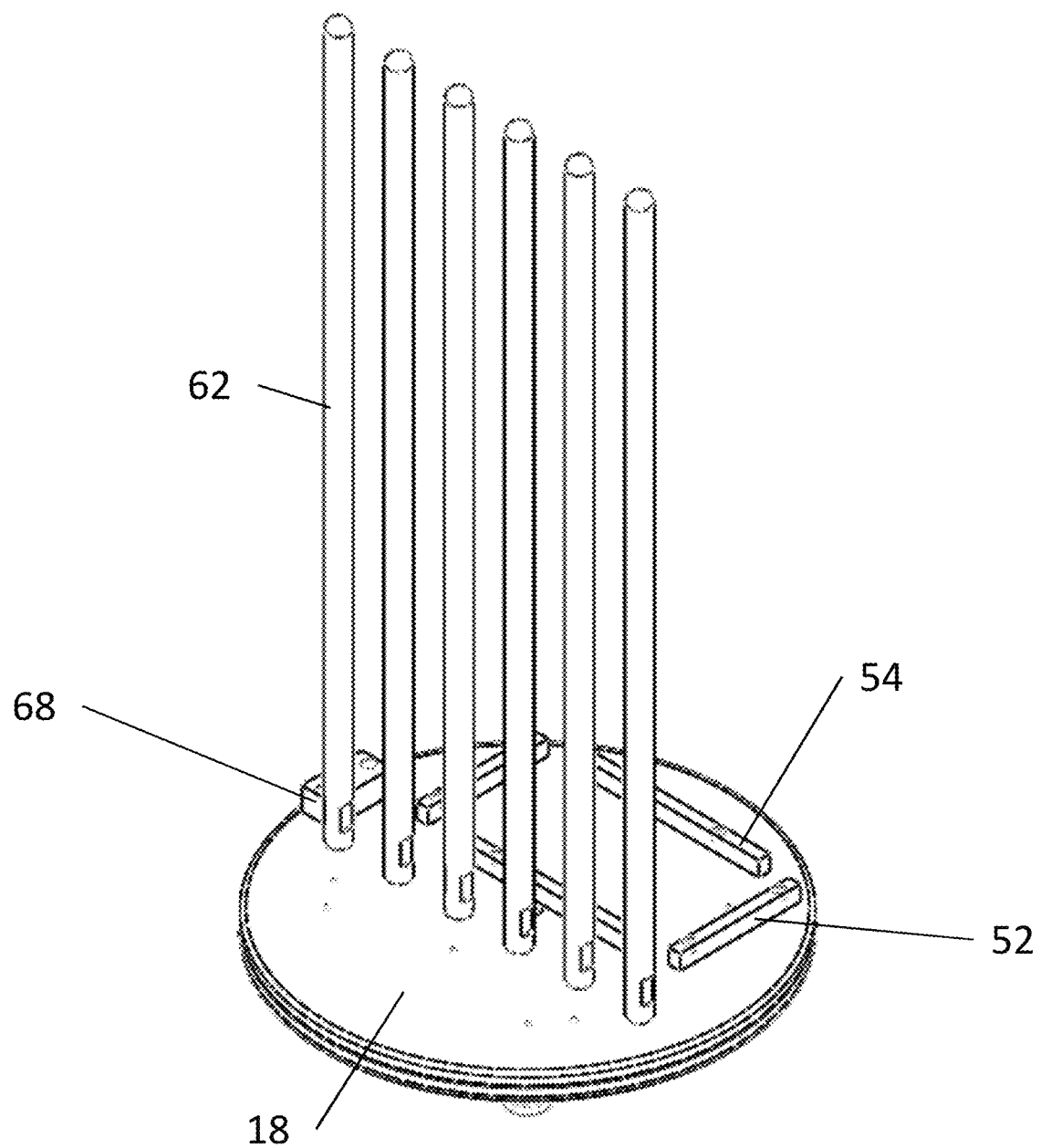

FIGS. 2A and 2B shows in detail respective exploded and assembled drawings of the movement device (18) and supporting mechanisms of the system (8). The movement device (18) includes a top cover (40) a bottom cover (44) and a moving surface (42) such as a rotating base or plate interposed between the top cover (40) and the bottom cover (44). The underside or under surface (46) of the bottom cover (44) is equipped with a plurality of feet (48), optionally removeable, for positioning the turning device (18) securely on a laboratory bench or other supporting surface. The upper side or upper surface (50) of the top cover (40) includes one or more short manifold stops (52) and one or more long manifold stops (54) for positioning the Stage 2 manifold (32).

In a preferred embodiment, the short (52) and long (54) manifold stops can be equipped with connection mechanism(s) (55) including first connectors (56) such as, for a non-limiting example, holes corresponding to second connectors, again such as, for a non-limiting example, holes (58) on the upper surface of the top cover (40). Connection devices (60) such as, for non-limiting examples, screws can be used for passing through the first connectors (56) and into the second connectors (58) for reversibly affixing the short (52) and long (54) manifold stops to the top cover (40) of the movement device (18). Other types of connection mechanisms known to those of ordinary skill in the art can be used for reversibly affixing the short (52) and long (54) manifold stops to the upper surface (5) of the top cover (40) of the turning device (18).

The movement device (18) includes one or more rod supports (62) for securing the assay columns and the Stage 1 and Stage 2 solvent reservoirs. The movement device (18) also includes a rod support positioning mechanism (63) for positioning the rod support(s) 62. The rod support positioning mechanism (63) includes one or more rod support receiver(s) (64) such as, for a non-limiting example, indentation(s), each of which corresponds to and is adapted for receiving a bottom end (66) of a respective rod support (62). Other types of support positioning mechanisms know to those of ordinary skill in the art can be used for positioning the rod supports. The turning device mechanism further includes a holder (68) such as, for a non-limiting example, a bracket for affixing a three-way valve (34) (identified in FIG. 1A) to the movement device (18).

Figure 3A:
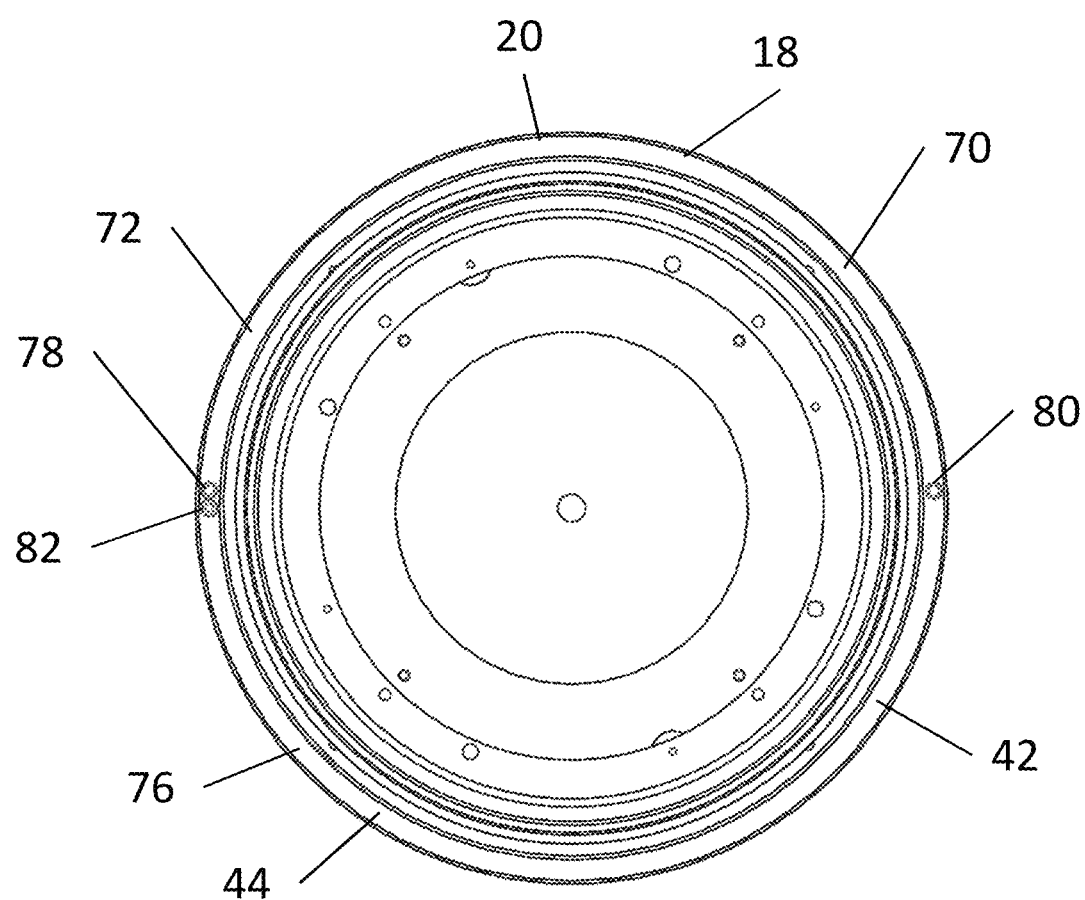
FIGS. 3A and 3B are plan or top views of a movement device in respective first and second positions.
Figure 3B:
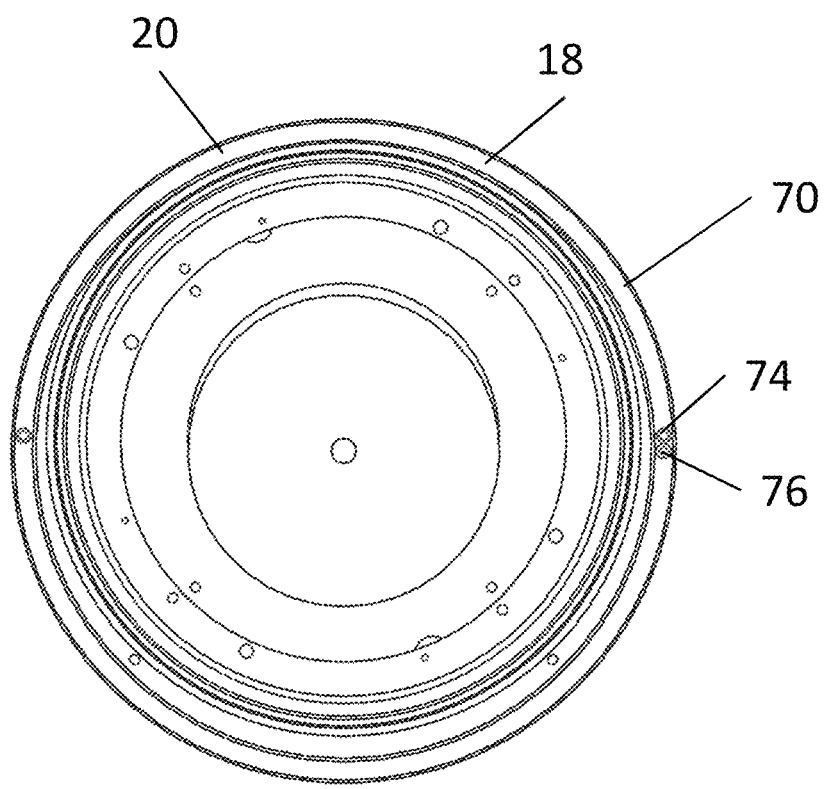
Figure 3C:
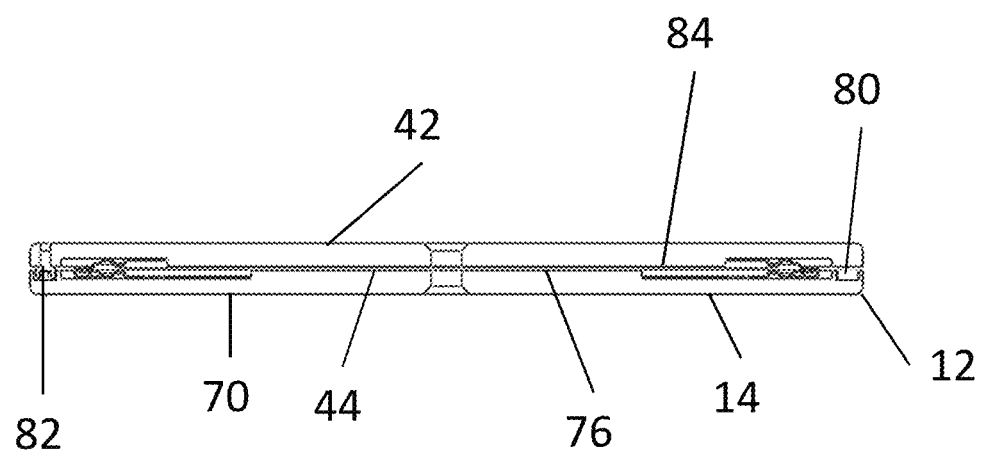
FIG. 3C is a sectional side view of the movement device for a liquid extraction and purification system in accordance with an embodiment of the invention.

In a preferred embodiment, the movement device (18) includes a rotating base (20) having a rotation mechanism (70), wherein the rotating base (20) rotates between a first position (72), as shown in FIG. 3A and a second position (74), as shown in FIG. 3B. In one embodiment, the top or upper surface (76) of the bottom cover (44) of the rotating base (20) includes at least one first rotation stop (78) bolted or otherwise affixed to the top surface (76) of the bottom cover (44) of the rotating base (20). The top surface (76) of the bottom cover (44) of the rotating base (20) includes at least one second rotation stop (80) bolted or otherwise affixed to the top surface (76) of the bottom cover (44) of the turn table (18) at a predetermined distance from the at least one first rotation stop (78). The bottom or lower surface (84) of the turning surface or plate (42) includes at least one rotation stop (82) bolted or otherwise affixed to the bottom surface (84) of the turning surface or plate (42), as shown in the section view of the rotation mechanism (70) in FIG. 3C. In operation, the maximum rotation of the turning surface (44) is thus limited in a range from the first rotation stop (78) to the second rotation stop (80). In another alternative embodiment, the rotating base (20) can include a single rotation stop including, for example, a ball plunger or a set screw for prevention of unwanted rotation in lieu of rotation stops (78), (80) and (82).

Figure 4A:
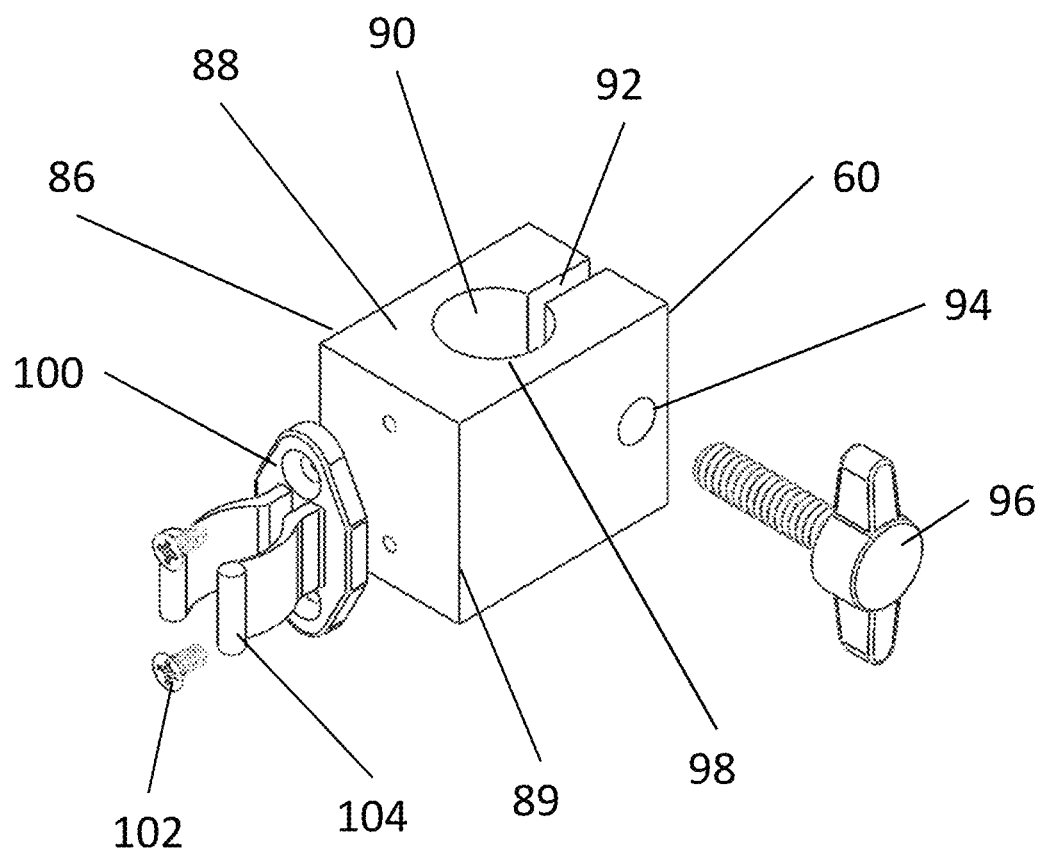
FIG. 4A is a perspective exploded view.
Figure 4B:
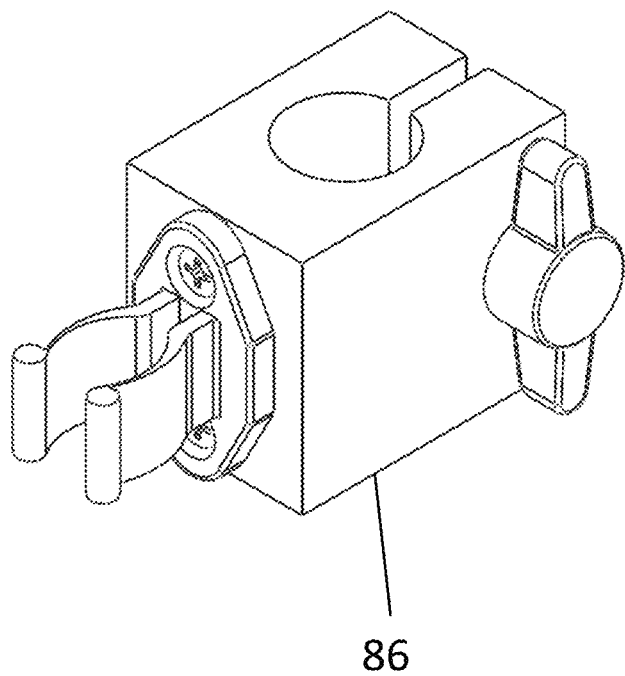
FIGS. 4B and 4C are perspective views of assembled views of lock block mechanisms for a liquid extraction and purification system in accordance with an embodiment of the invention.
Figure 4C:
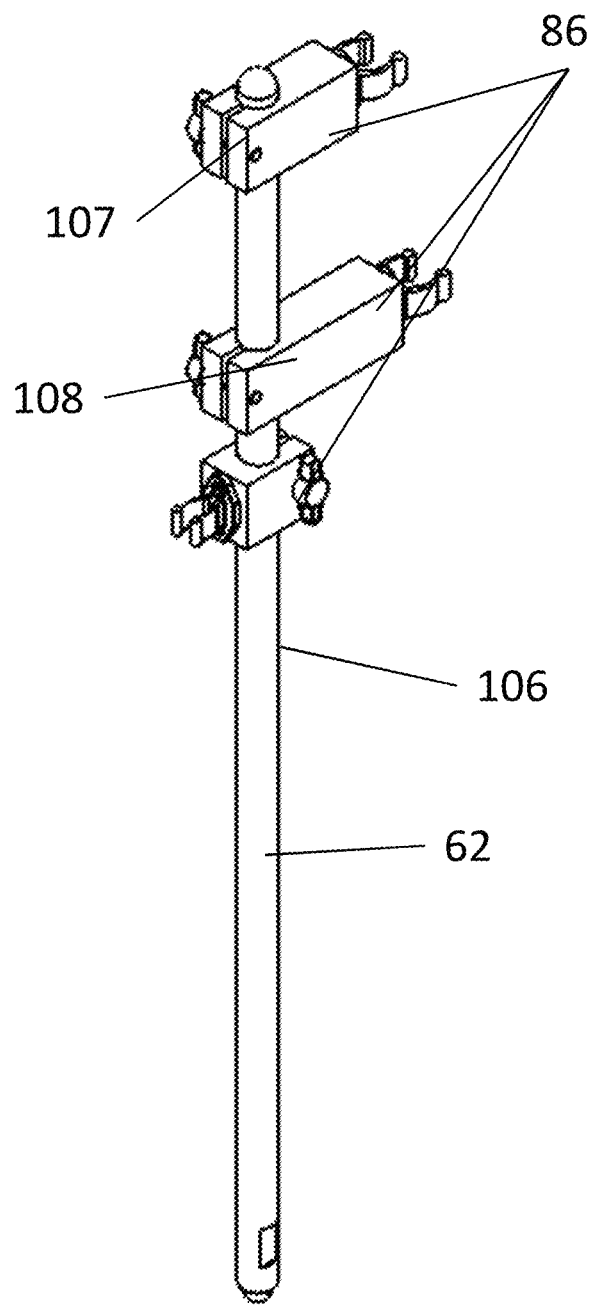

The assay column assembly (24) shown in FIG. 1A can be reversibly attached to the rod support(s) (62) by way of the lock block mechanisms (86) shown in detail FIGS. 4A, 4B and 4C. FIGS. 4A and 4B show respective exploded and assembled views of a lock block mechanism (86). In a preferred embodiment, each lock block mechanism (86) includes a lock block (88) having a lock block opening (90) and a passageway (92). The lock block mechanism (86) can be reversibly affixed onto a rod support (62) by substantially pressing the lock block (88) onto the rod support (62) via the passageway (92) after which the rod support (62) in a substantially vertical orientation passes through the opening (90) of the lock block mechanism (86). The lock block (88) can be adapted to have a tightening receiving portion (94) for reversibly receiving a tightening device (96) such as, for a non-limiting example, a thumb screw. The tightening device (96) can be can reversibly inserted into the tightening receiving portion (94) and turned or otherwise adjusted to reversibly press or compress the sides or inner surface (98) of the lock block opening (90) against a rod support (62) thereby securing the assay support column (62) in place, as shown in FIG. 4C.

The lock block mechanism (86) can also include an assay column clip (100) including assay column clip attachment devices (102), such as, for a non-limiting example, screws, for reversibly attaching the assay column clip (100) to the lock block (88), preferably on a side (89) of the lock block (88) opposed to the passageway (92). After the assay column clip (100) is attached reversibly to the lock block (88), it can then be used to receive reversibly an assay column assembly (24) oriented substantially vertically. The assay column clip (100) can be adapted to receive reversibly an assay column assembly (24) in different ways which are known to those of ordinary skill in the art. In the preferred, non-limiting embodiments shown in FIGS. 4A, B and C, the assay column clip (100) is adapted to receive reversibly an assay column with prongs (104) which open under pressure and spring back to grip the assay column assembly (24) when the assay column assembly (24) is pressed against the prongs (104) and then the pressure is released after the assay column assembly (24) is in position. The dimensions of the various parts of the lock block mechanism (86) including, for non-limiting examples, the length, width, and height dimensions of the lock block (88) and/or the assay column clip(s) (100) can be varied to accommodate different configurations of the system (8) including for non-limiting examples the different dimensions of the rod supports (62) and assay column assemblies (24). For non-limiting examples, FIG. 4C shows three differently sized small (106), medium (107) and large (108) lock block mechanisms (86) affixed to rod support (62).

Figure 5A:
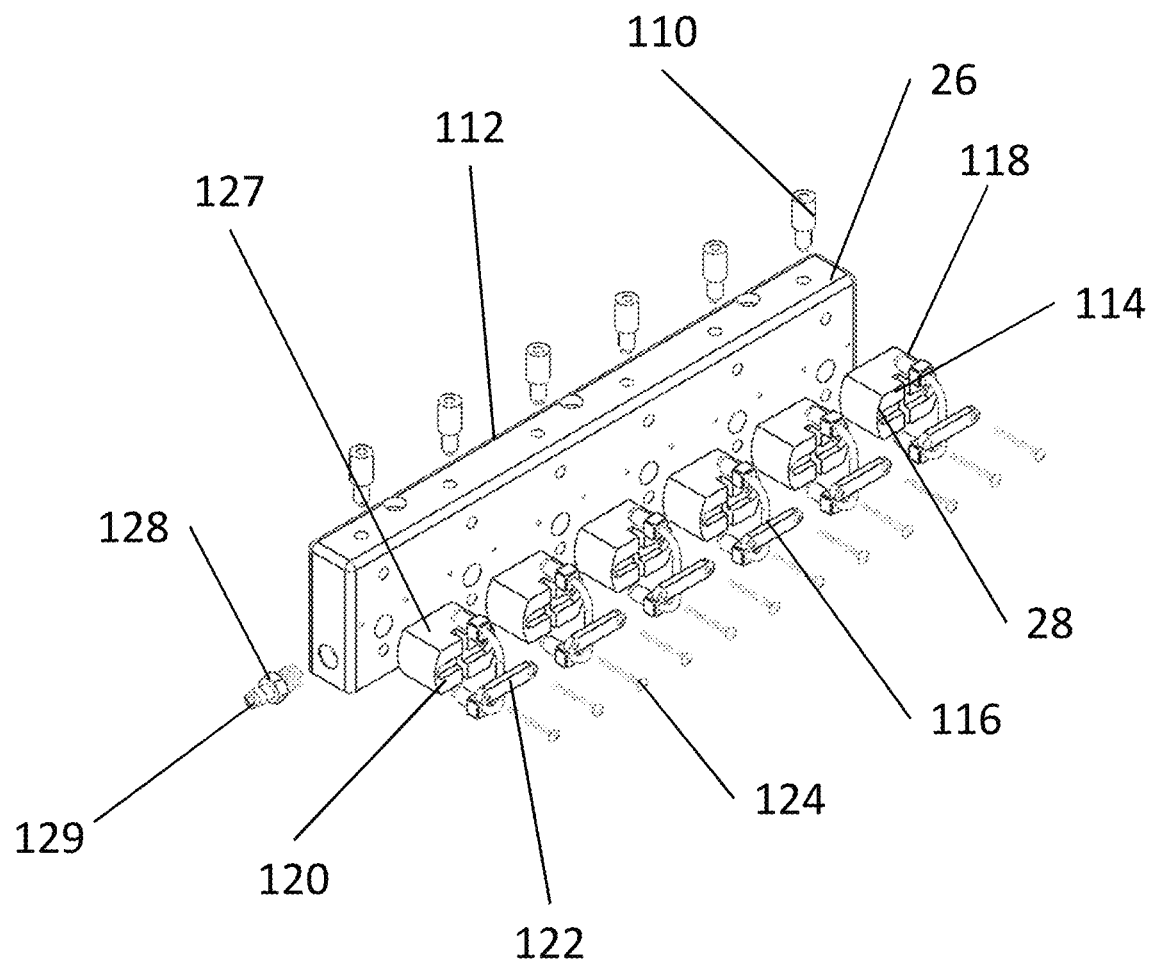
FIGS. 5A and 5B are respective exploded and assembled views of a Stage 1 Manifold for a liquid extraction and purification system in accordance with an embodiment of the invention.
Figure 5B:
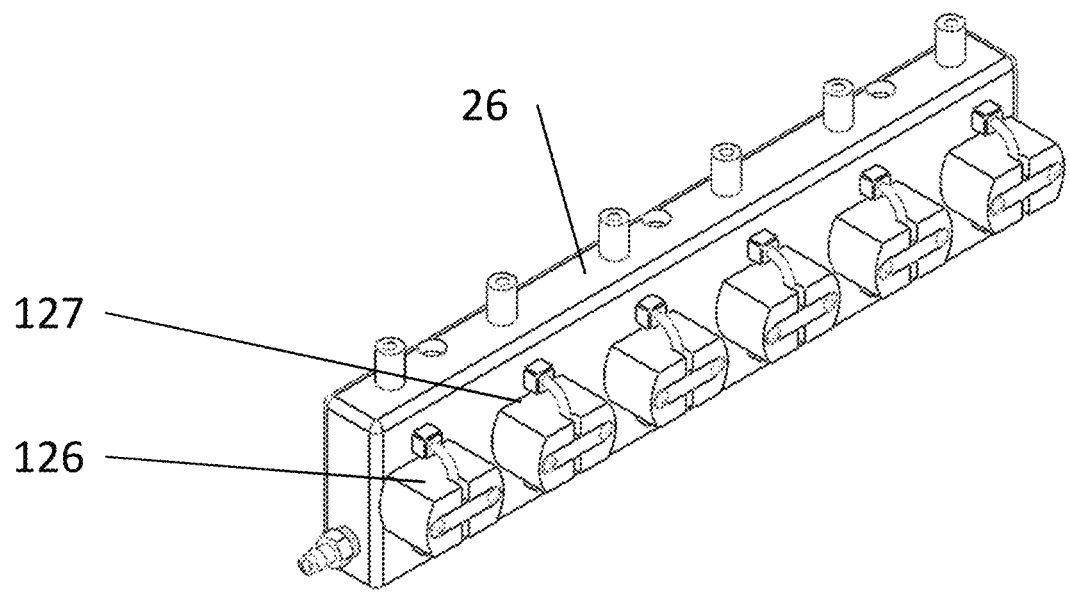

FIGS. 5A and 5B show respective exploded and assembled views of the Stage 1 manifold (26). The Stage 1 manifold (26) includes one or more adapters (110), such as luers, for fluidically connecting the Stage 1 manifold (26) to one or more corresponding assay column assemblies (24). The Stage 1 manifold (26) also includes one or more column support receivers (112) adapted for receiving one or more corresponding column supports (62). The Stage 1 manifold (26) is fluidically connected to one or more Stage 1 manifold sensors (28).

In different embodiments, the Stage 1 manifold sensor (28) can include a Stage 1 manifold bubble sensor (114), a LED sensor (126), an audio sensor (127), and/or combinations thereof, where the Stage 1 manifold sensor (28) corresponds to one or more assay column assemblies (24) and provides an indication when an extraction, purification, fractionation, and/or concentration is completed in the respective assay column assembly (24). In one embodiment, as shown in FIGS. 5A and 5B, the Stage 1 manifold bubble sensor (114) includes a see-through tubing loop (116) fluidically and reversibly connected via fittings (118) to the Stage 1 manifold (26) for visual detection of air bubble(s). The Stage 1 manifold sensor (28) can be reversibly physically connected to the Stage 1 manifold with brackets (120) and (122) and connection devices (124) such as screws for securing the Stage 1 manifold sensor (28) to the Stage 1 manifold (26). In another embodiment, the Stage 1 manifold (26) can include one or more LED sensor(s) (126) corresponding to the one or more assay column assemblies (24) for a visual indication of when a corresponding solvent from a corresponding solvent reservoir (28) has passed through and exited a corresponding assay column assembly (24). The Stage 1 manifold further includes exit port (128) including for a non-limiting example, as barb fitting (129), for fluidically connecting the Stage 1 manifold (26) to the three-way valve (34) shown in FIG. 1A.

Figure 6A:
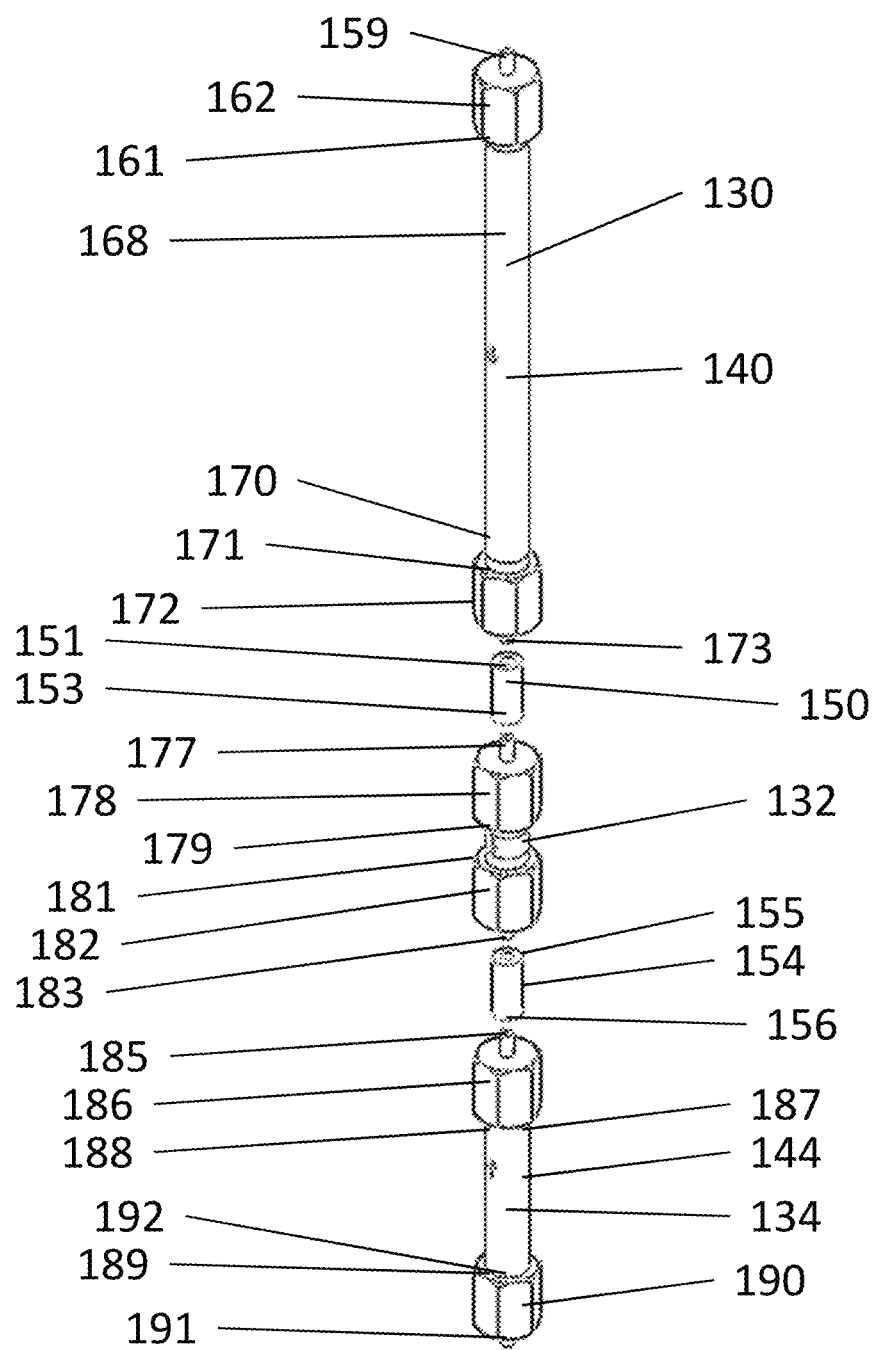
FIGS. 6A and 6B are respective exploded and assembled views of an assay column assembly for a liquid extraction and purification system in accordance with an embodiment of the invention.
Figure 6B:
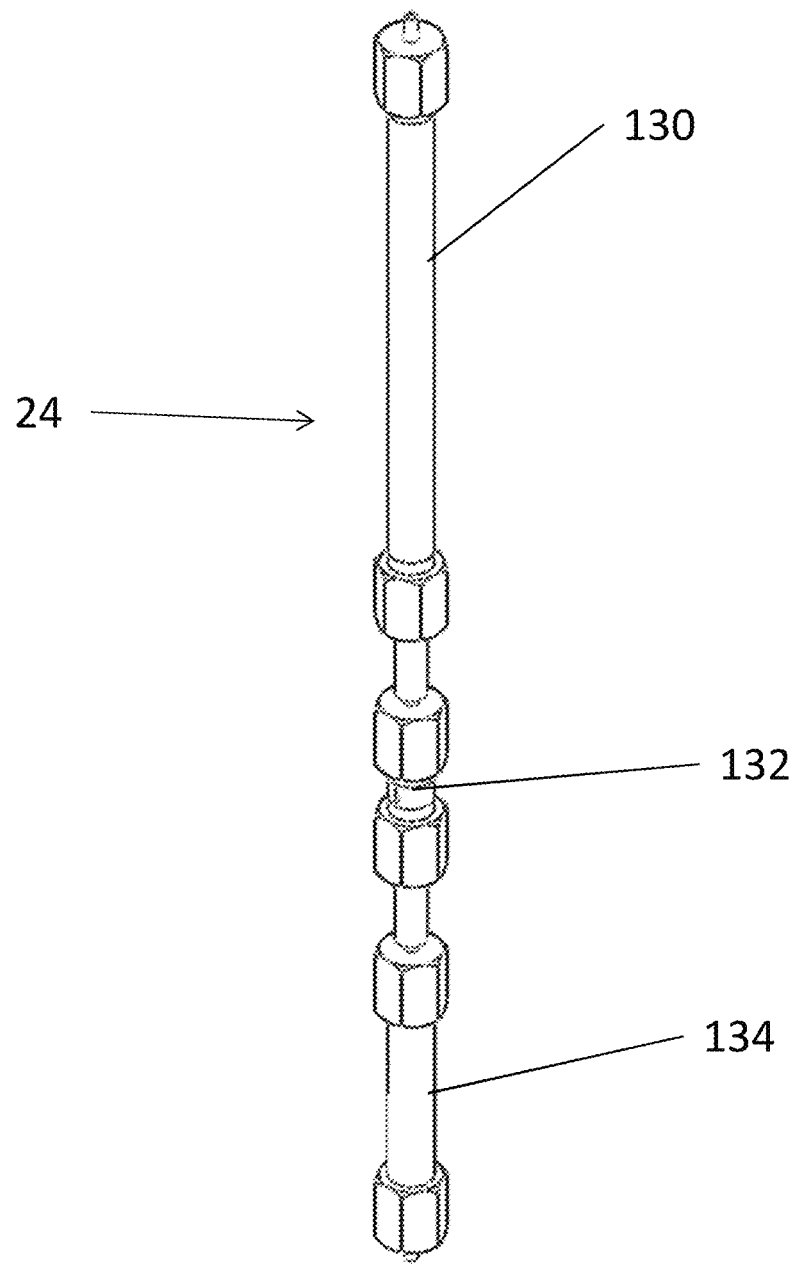

FIGS. 6A and 6B show respective exploded and assembled views of assay column assembly (24) In a preferred embodiment, an assay column assembly (24) can include a first assay column (130) fluidically and reversibly connected in series to a second assay column (132). In a more preferred embodiment, assay column assembly (24) additionally includes a third assay column (134) fluidically and reversibly connected in series to the second assay column (132). In preferred embodiments, each assay column can include a material in one or more layers and/or chemical preparations selected and/or optimized for the particular assay of the respective assay column. In one embodiment, the assay column (130) includes silica (140). In another embodiment, the second assay column (132) includes carbon (142). In yet another embodiment, the third assay column (134) includes alumina (144). In one embodiment, the first (130) and second (132) assay columns are fluidically and reversibly connected with an easy connect fitting (150) such as, for a non-limiting example, a luer having a first end (151) and a second end (153). In another embodiment, the second (132) and the third (134) assay columns are fluidically and reversibly connected with an easy connect fitting (154) such as a luer having a first end (155) and a second end (156).

Figure 7B:
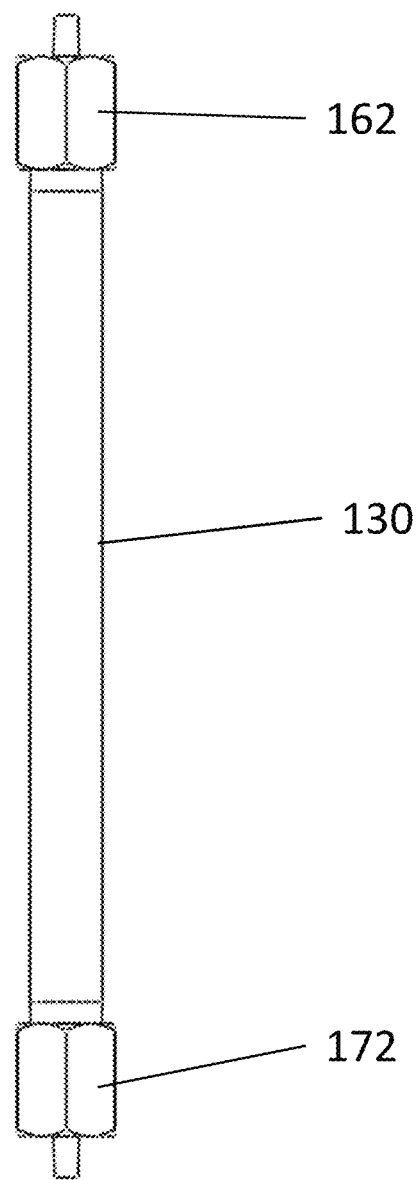

FIG. 7A is a sectional view showing the inside of the first assay column (130) in a vertical orientation. The sample for testing can be added to a sample vial which in turn can be fluidically and reversibly connected to assay column (130). Alternatively, the sample can be loaded directly into the sample chamber (160). An easy connect fitting (162) can be fluidically and reversibly connected through a portion, such as a female portion (161) to a first chamber end (164) of the sample chamber (160). The easy connect fitting (162) can be equipped with a portion such as a threaded female portion or a male portion (159), as shown in FIG. 7A, for fluidic and reversible connection from the first assay column to a Stage 1 solvent reservoir (22). The second chamber end (166) of the sample chamber (160) can be fluidically and reversibly connected to a first end (168) of the first assay column (130). A second end (170) of the first assay column (130) can be fluidically and reversibly connected to an easy connect fitting (172) through a female portion (171). Easy connect fitting (172) can have a male portion (173) such as, for a non-limiting example, a male luer adapter for fluidically and reversibly connecting to a first end (151) of the easy connect mechanism (150) shown in FIG. 6A. FIGS. 7B and 7D show respective side elevation and perspective views of the first assay column (130) fluidically and reversibly connected to easy connect fittings (162) and (172).

Notably, above, below and throughout the patent application, male and female portions, luers, and other connections can be reversed, as necessary.

Figure 7C:
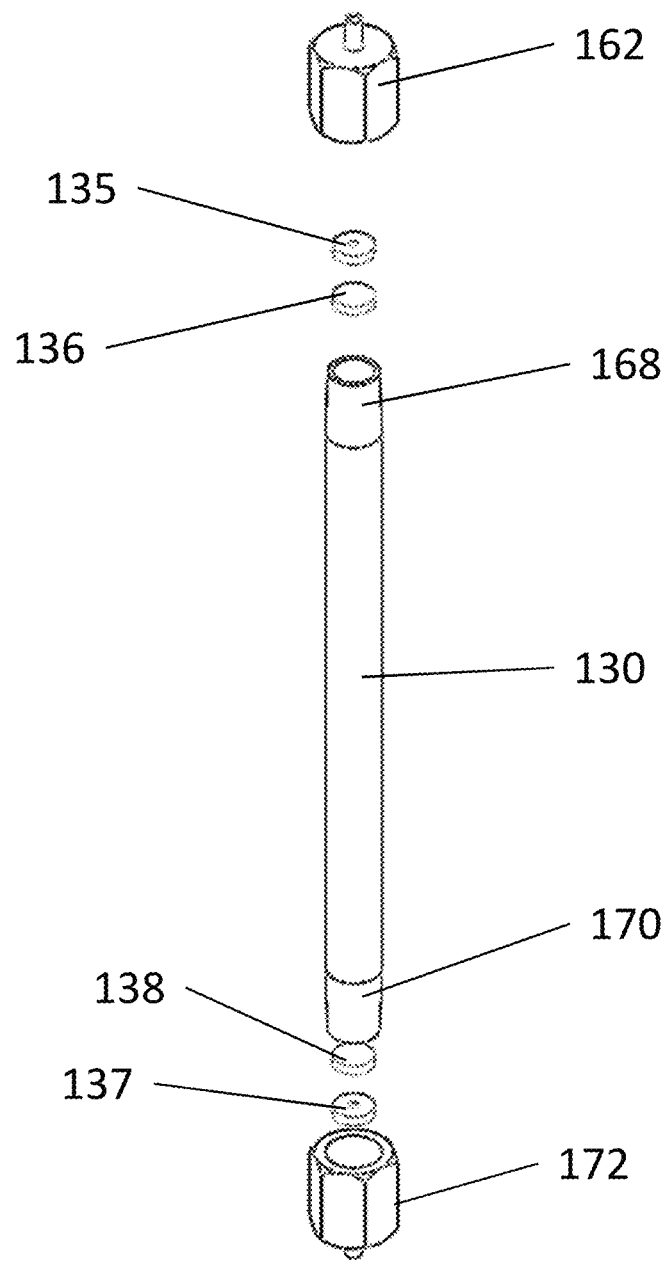
Figure 7D:
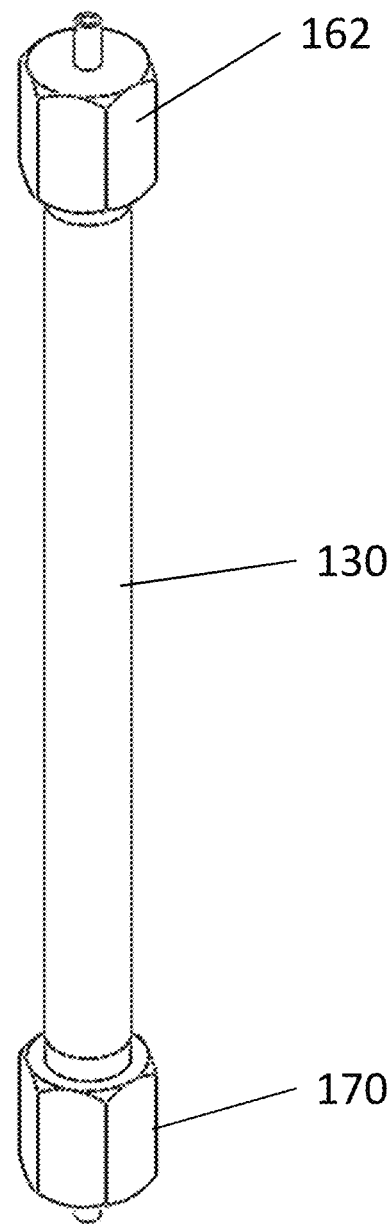

FIG. 7C shows an exploded view of a first assay column (130) including a glass frit (136) and a glass frit holder (135) disposed at a first end (168) of the first assay column (130) and a glass frit (138) and glass frit holder (137) disposed at a second end (170) of the first assay column.

Figure 8A:
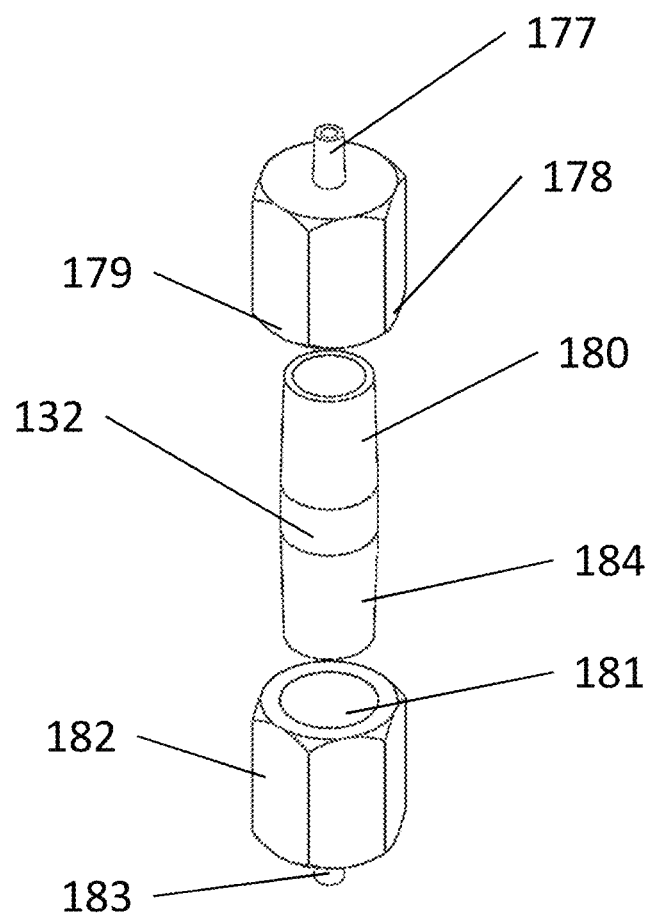
FIGS. 8A and 8B are respective exploded and assembled views of a second assay column for a liquid extraction and purification system in accordance with an embodiment of the invention.
Figure 8B:
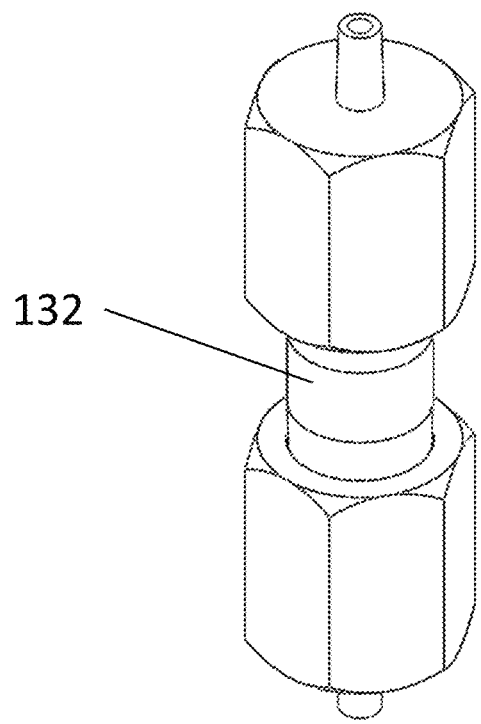

FIGS. 8A and 8B show respective exploded and assembled views of a second assay column (132). A first end (180) of the second assay column (132) can be fluidically and reversibly connected to an easy connect fitting (178) through a female portion (179). A male portion (177) portion such as a male luer adapter of the easy connect fitting (178) can be fluidically and reversibly connected to a second end (153) of easy connect fitting (150) shown in FIG. 6A. A second end (184) of the second assay column (132) shown in FIG. 8A can be fluidically and reversibly connected to a female portion (181) of an easy connect fitting (182). A male portion (183) such a male luer adapter of the easy connect fitting (182) can be fluidically and reversibly connected to a first end (155) of easy connect fitting (154) shown in FIG. 6A.

Figure 9A:
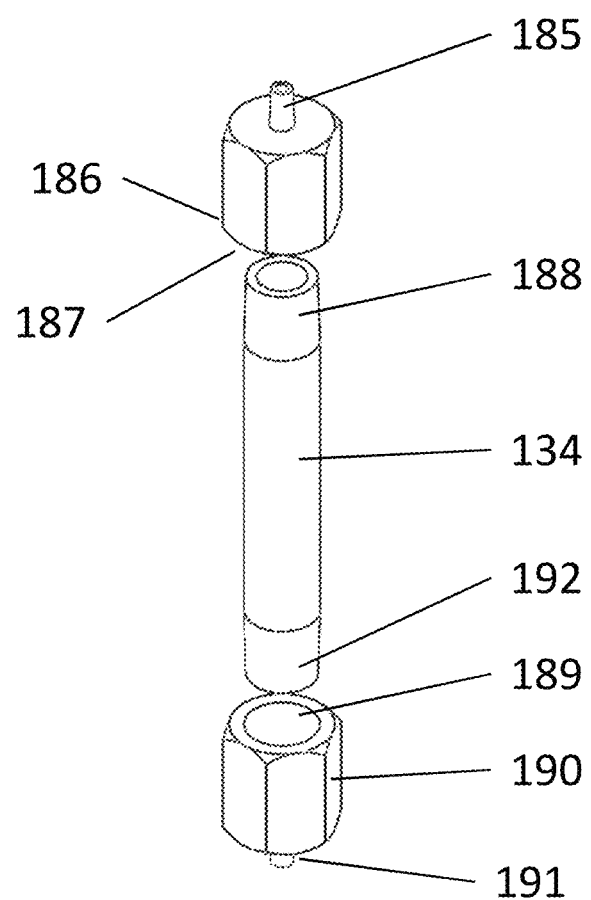
FIGS. 9A and 9B are respective exploded and assembled views of a second assay column for a liquid extraction and purification system in accordance with an embodiment of the invention.
Figure 9B:
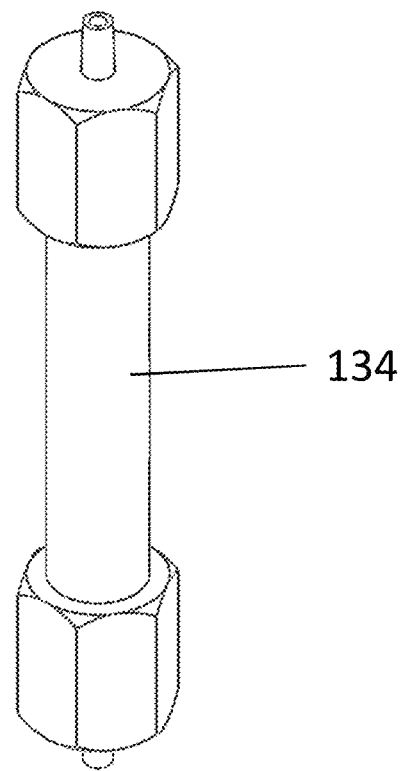
Figure 10A:
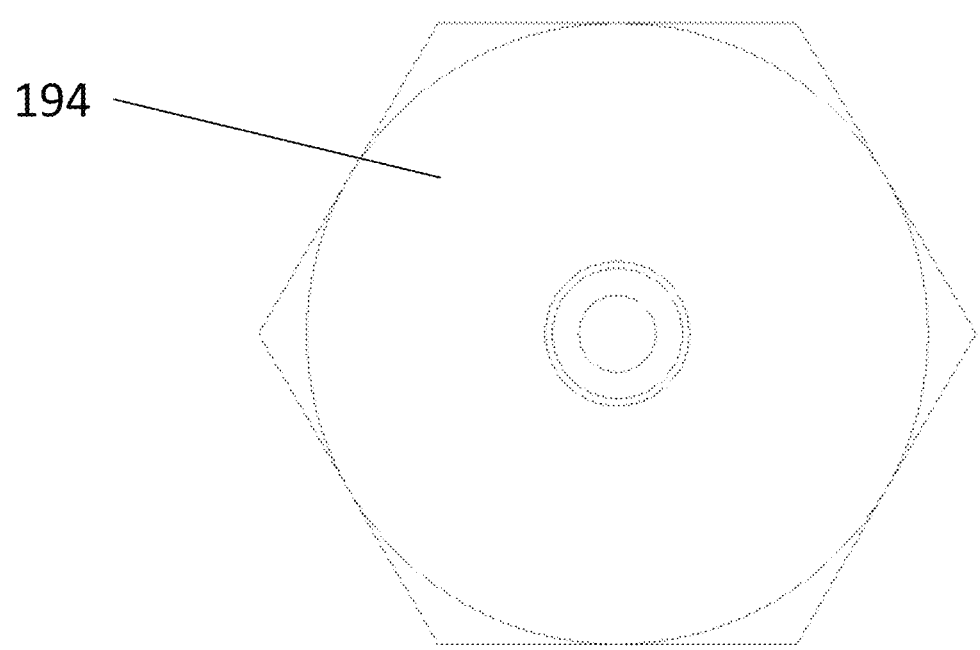
FIGS. 10A, 10B, 10C and 10D are respective front elevation, side elevation, sectional and perspective views of an easy connect fitting for use in a liquid extraction and purification system in accordance in accordance with an embodiment of the invention.
Figure 10B:
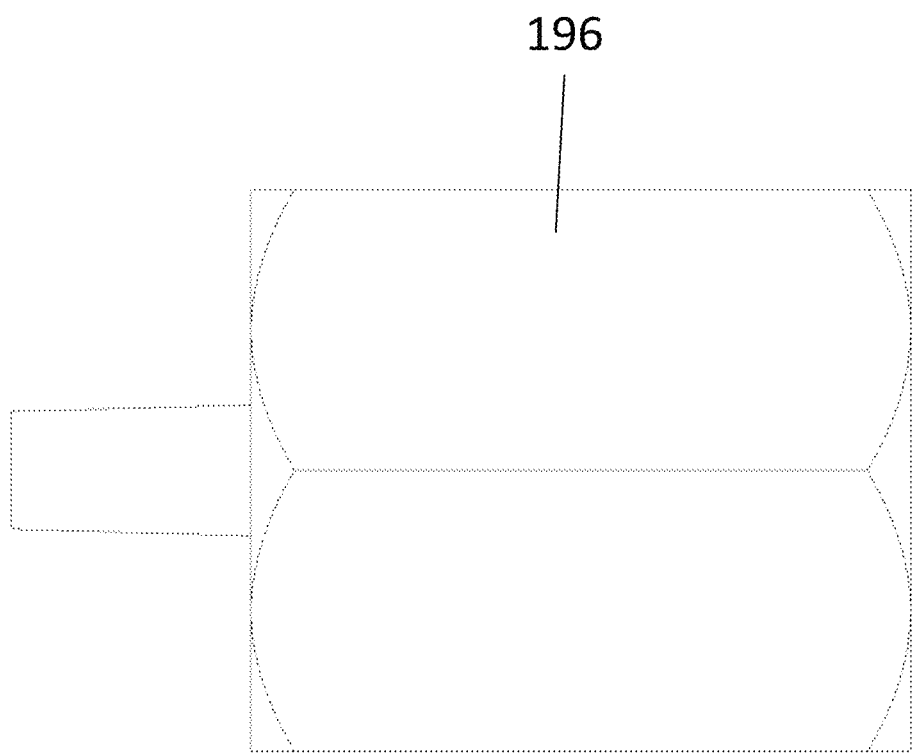
Figure 10C:
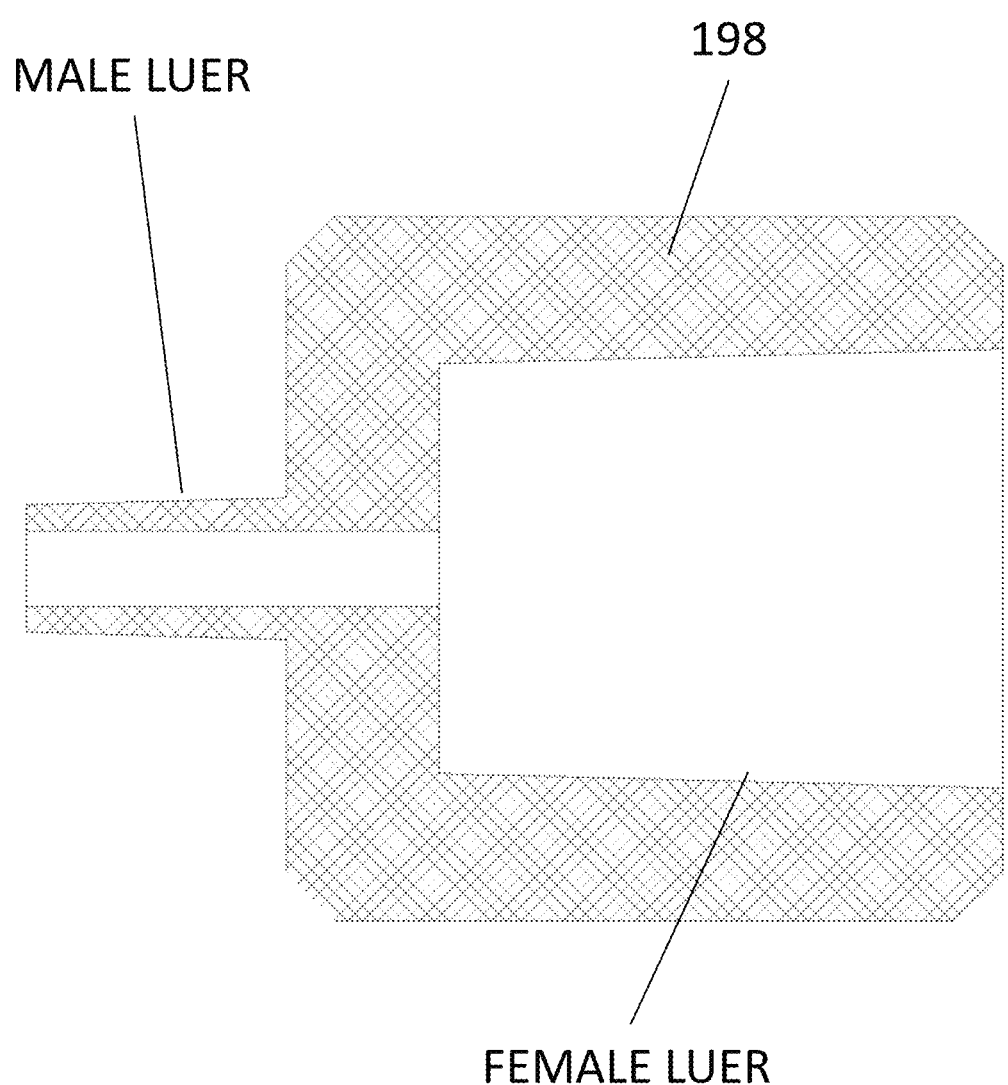
Figure 10D:
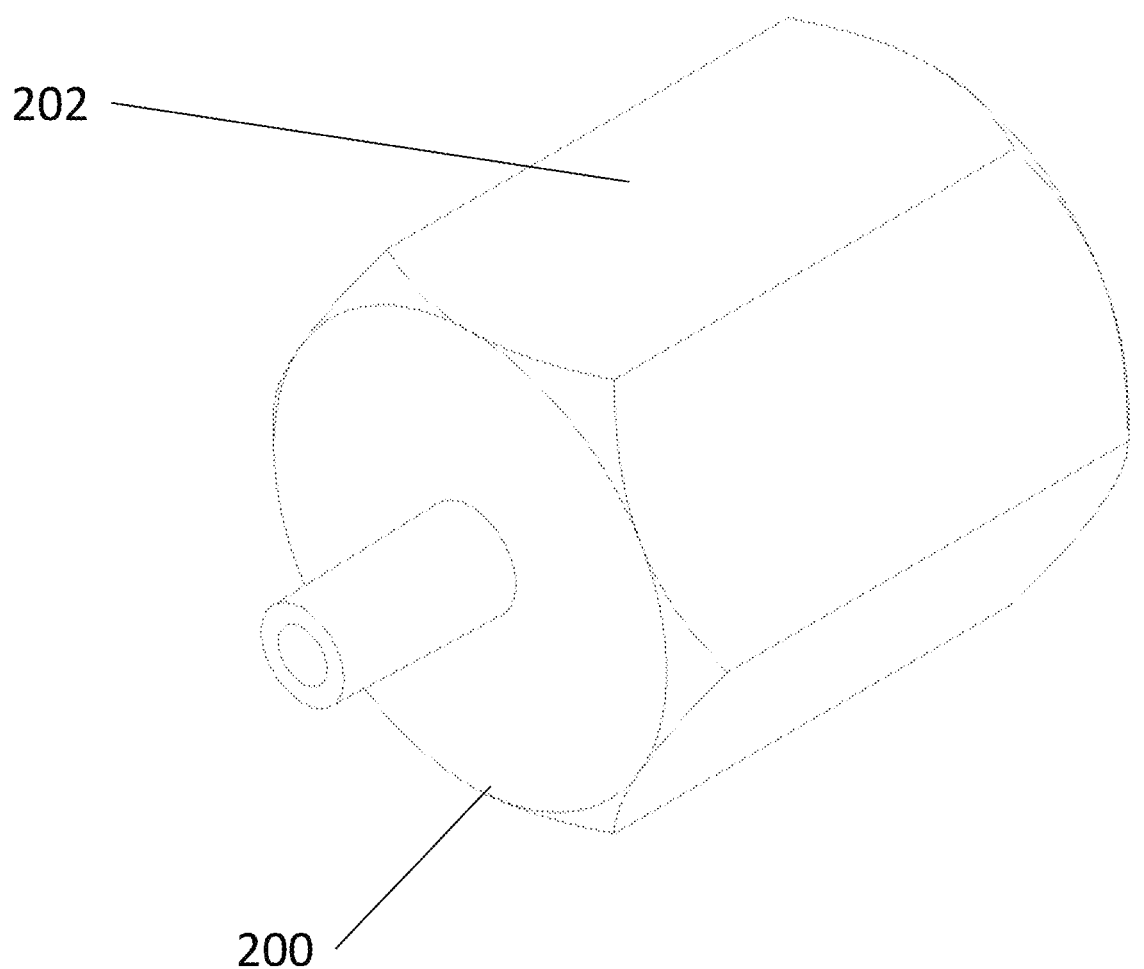

FIGS. 9A and 9B show respectively exploded and assembled views of a third assay column (134). A first end (188) of the third assay column (134) can be fluidically and reversibly connected to a female portion (187) of an easy connect fitting (186). A male portion such as a male luer adapter (185) of the easy connect fitting (186) can be fluidically and reversibly connected to a second end (156) of easy connect fitting (154) shown in FIG. 6A. A second end (192) of assay column (134) can be fluidically and reversibly connected to a female portion (189) of easy connect fitting (190). A male portion such as a male luer adapter (191) of an easy connect fitting (190) can be used to fluidically and reversibly connect to a Stage 1 manifold.

FIGS. 10A, 10B, 10C and 10D show respectively a front elevation view (194), a side elevation view (196), a sectional view (198) and a perspective view (200) of an exemplary easy connect fitting (202) adapted for fluidic and reversible connections.

FIG. 11A shows a Stage 1 configuration of the assay column assembly (24). During operation, a sample is loaded into the assay column assembly (24), as shown in Step 1-1 of FIG. 11A. The solvent reservoir (22) including, for a non-limiting example, hexane, is fluidically and reversibly connected to the column assembly (24) and the solvent is eluted through the column assembly (24). The assay column assembly (24) includes assay columns (130, 132 and 134) wherein the assay columns (132) and (134) are disposed to accomplish respective flow directions (204) and (206) for passage of a solvent (208) from the Stage 1 solvent reservoir (22) through the assay columns. Waste fluid (210) is collected in waste reservoir (212).

Figure 11B:
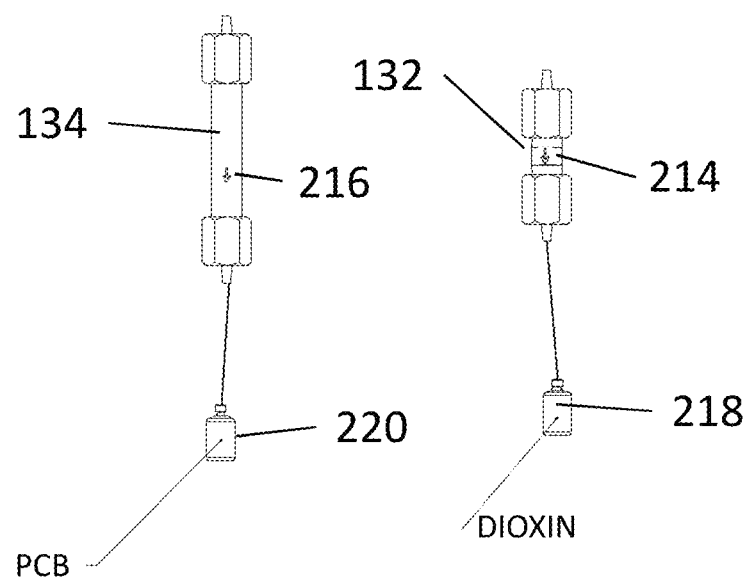

FIG. 11B shows a Stage 2 configuration including two assay columns. Assay columns (132) and (134) are disconnected from the Stage 1 assembly and turned substantially up down. Flow of solvent through the assay columns (132) and (134) is substantially reversed from respective flow directions (204) and (206) to respective reverse flow directions (214) and (216). In one embodiment, the assay columns (132) and (134) are not operated in series. Sample is eluted through the assay columns (132) and (134), as shown in FIG. 11B. Fraction is collected from assay column (132) in one or more fraction vial receptacles (218), and fraction is collected from assay column (134) in one or more fraction vial receptacles (220).

Figure 12B:
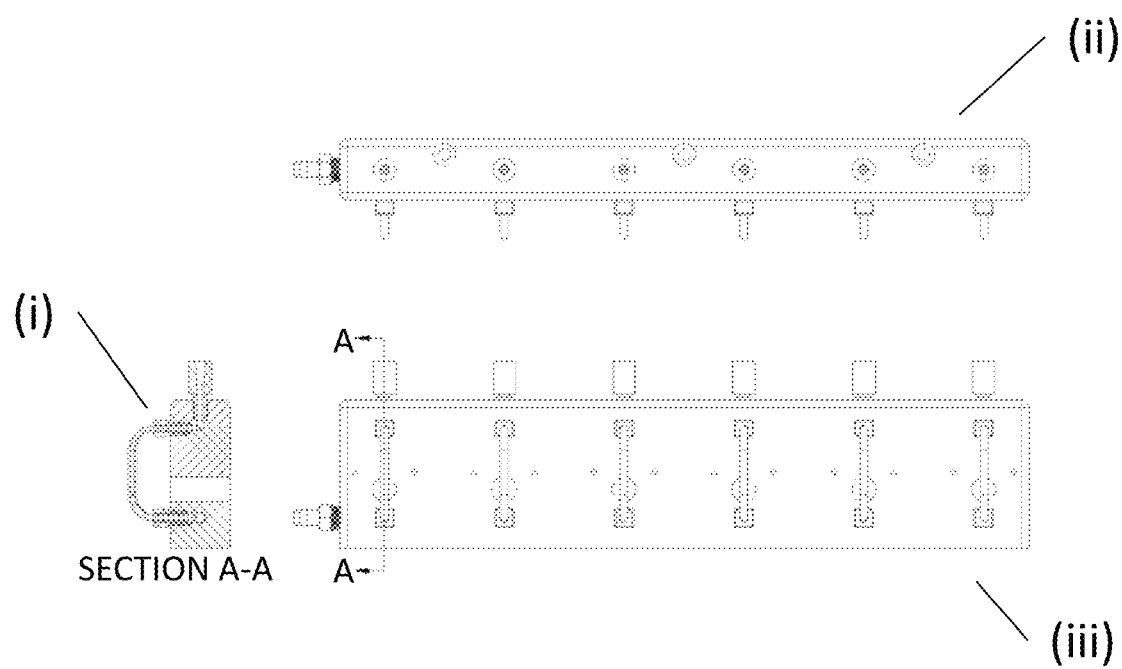
FIG. 12B (i, ii, and iii) are respective sectional, plan or top, and front elevation views of a Stage 1 manifold without Stage 1 manifold sensors in accordance with an embodiment of the invention.

FIG. 12A (i, ii iii, and iv) are respective sectional, plan or top, front elevation and sectional views of a Stage 1 manifold. The Stage 1 manifold includes one or more Stage 1 manifold sensors (126). The flow path of fluid through the Stage 1 manifold is shown by arrow (222). FIG. 12B (i, ii and iii) are respective sectional, plan or top, and front elevation views of a Stage 1 manifold without Stage 1 manifold sensors (126).

Figure 13:
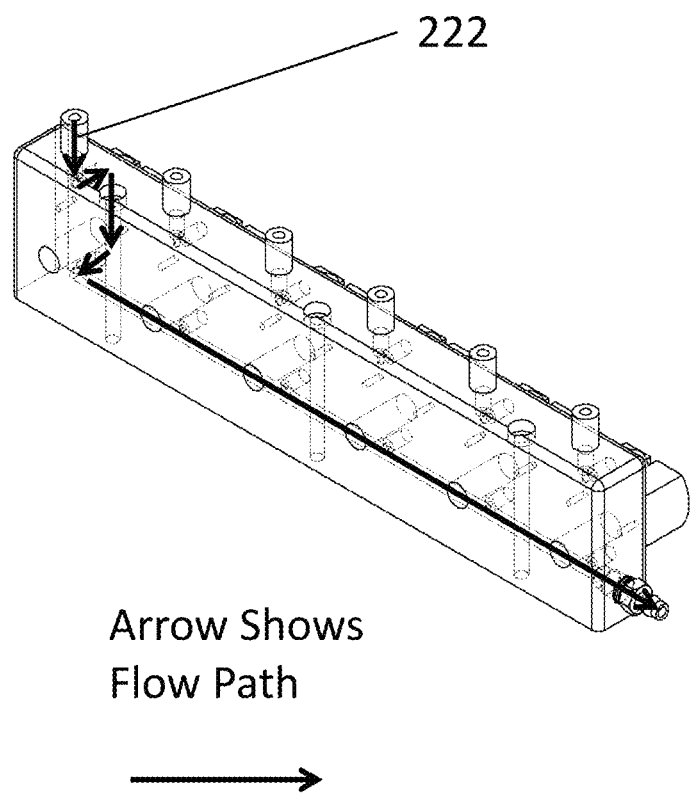
FIG. 13 is a transparent view of Stage 1 manifold including the path of fluid there through in accordance with an embodiment of the invention.

FIG. 13 shows a transparent view of the Stage 1 manifold including the path of fluid (222) there through.

FIG. 14 shows the Stage 1 configuration including assay columns, solvent reservoir installation, and connections. Tubing, as shown by exemplary arrow (224) connects each of the Stage 1 solvent reservoirs (22) to the easy connect fitting (162) disposed at the first entry of the first assay column (130) of the corresponding column assembly (24). The Stage 1 manifold (26) includes at least one stopcock (226) for reversibly stopping fluid flowing from the corresponding third assay column (134) into the first manifold (26). During an exemplary installation, a luer adapter of a third assay column (134) containing, for a non-limiting embodiment, alumina, is connected to the stopcock (226). The column assembly (24) is pushed onto the clip. The solvent reservoir is also installed by pushing onto a corresponding clip.

FIG. 15 shows the steps for conditioning the assay column assembly (24) according to an embodiment of the invention.

Figure 16A:
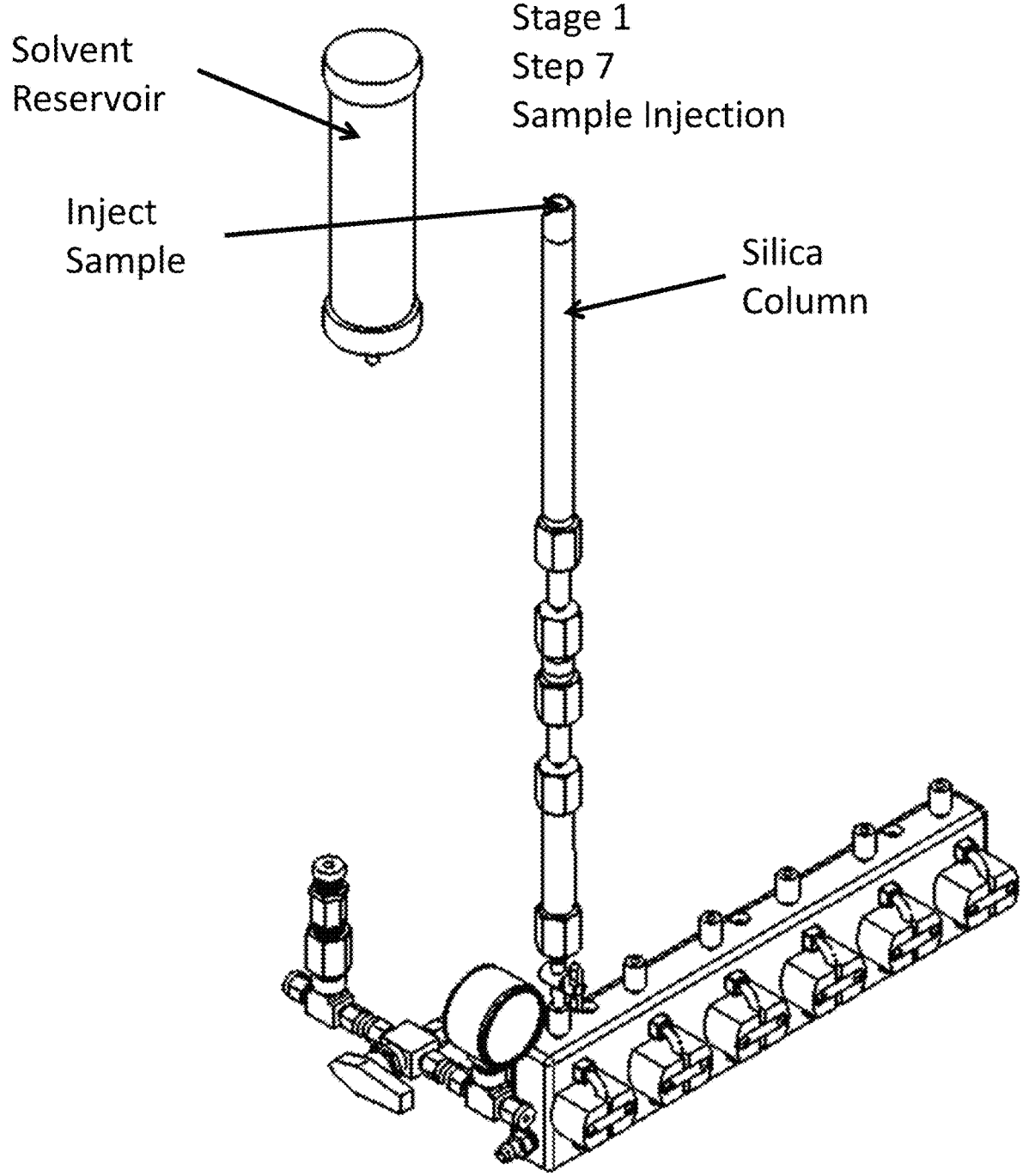
FIG. 16A is a schematic representation of steps for sample injection in accordance with an embodiment of the invention.

FIG. 16A shows the steps for sample injection according to an embodiment of the invention.

FIG. 16B shows introduction of a sample to the system through insertion of a vial including sample to the top or first end of the assay column assembly (24).

Figure 17:
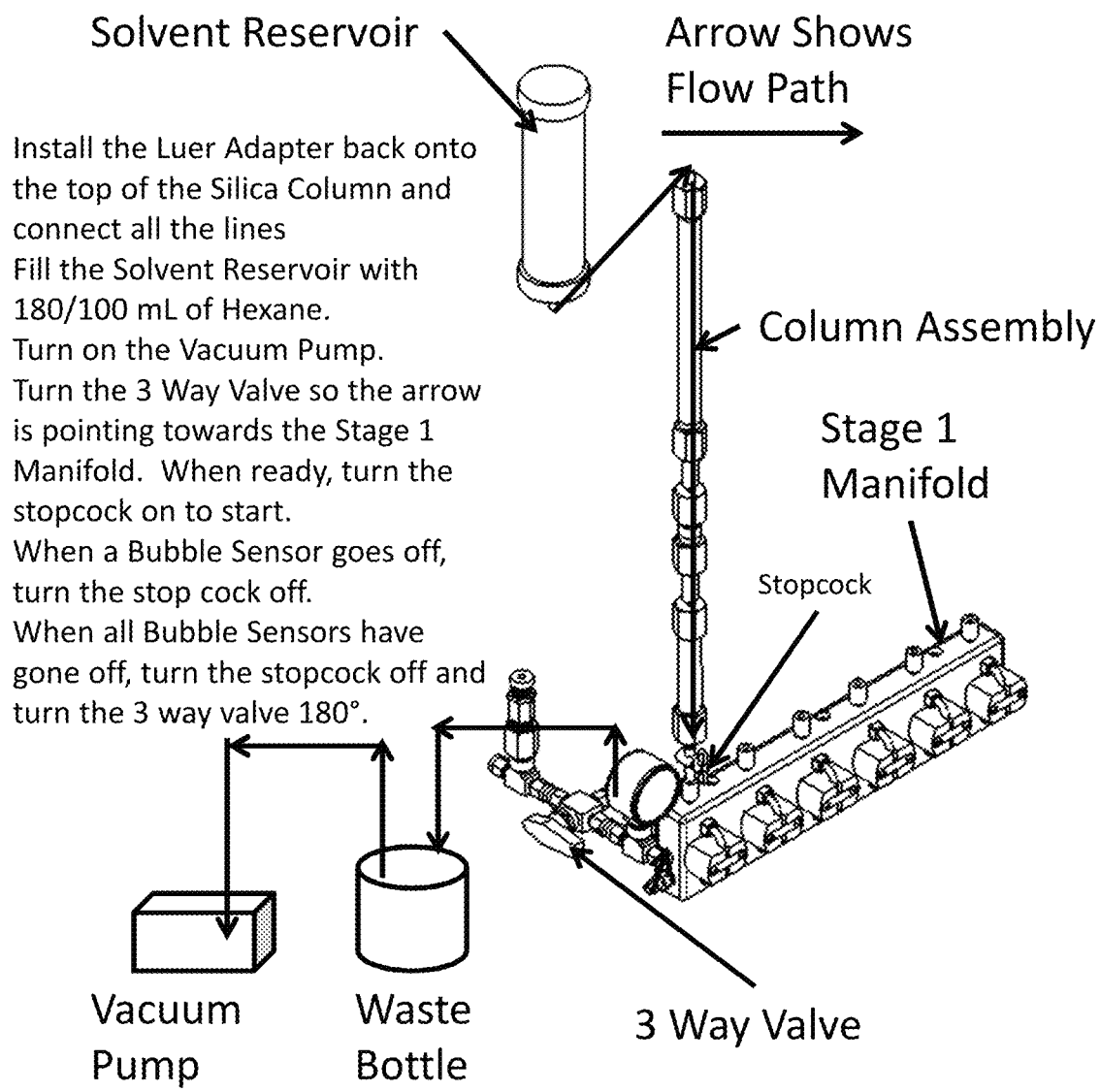
FIG. 17 is a schematic representation of steps for elution of a Stage 1 solvent in accordance with an embodiment of the invention.

FIG. 17 shows the steps for elution of a Stage 1 solvent including hexane according to an embodiment of the invention.

Figure 18:
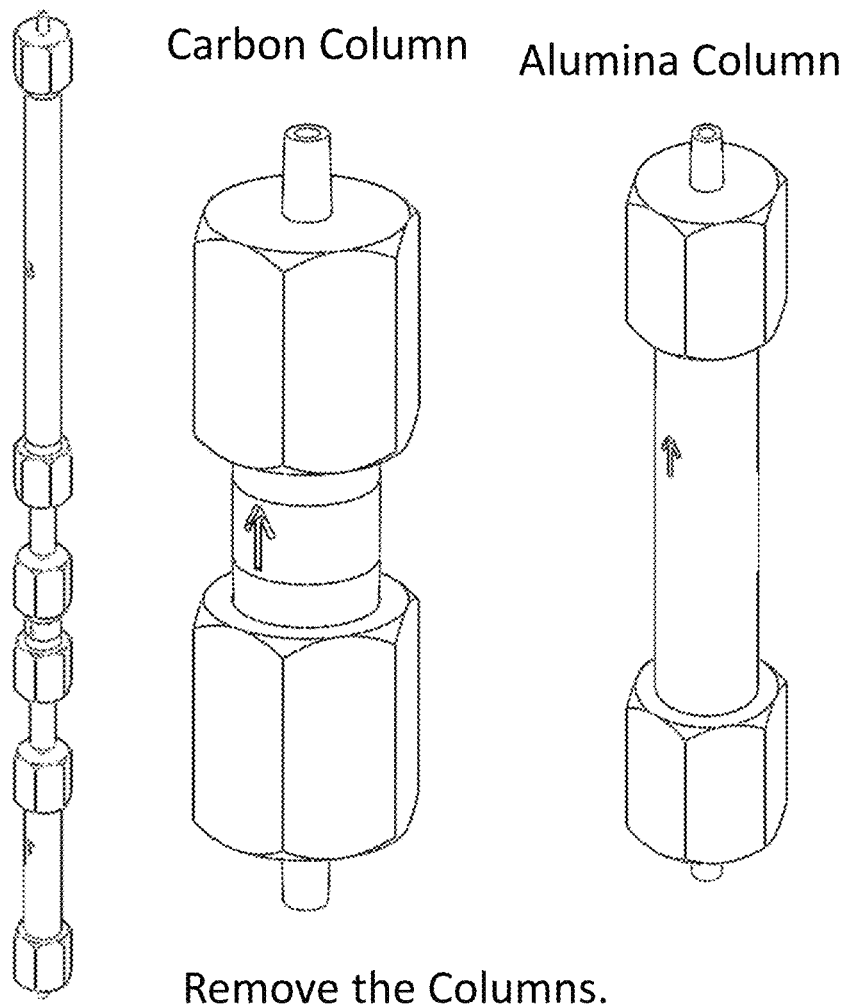
FIG. 18 is a schematic representation of steps for column disassembly from a Stage 1 manifold prior to connection of selected assay columns to a Stage 2 manifold in accordance with an embodiment of the invention.

FIG. 18 shows the steps for column disassembly from the Stage 1 manifold prior to connection of selected carbon and alumina assay columns to the Stage 2 manifold according to an embodiment of the invention.

FIG. 19 shows a system and steps for a Stage 2 of the method of the invention including connection of carbon and alumina assay columns onto the Stage 2 manifold according to an embodiment of the invention. In FIG. 19, the Stage 2 manifold includes at least one stop cock fluidically and reversibly connecting the corresponding assay column to the Stage 2 manifold. The stop cock can be disposable particularly where there is a concern for cross-contamination. Alternatively, the stop cock can be reusable.

FIG. 20 shows a system and steps for a sample elution of Stage 2 of the invention according to an embodiment of the invention.

FIG. 21 shows the steps for a Stage 1 protocol or operational method according to an embodiment of the invention.

FIG. 22 shows the steps for a Stage 2 protocol or operational method according to an embodiment of the invention.

FIG. 23 shows a system and steps for a Stage 2 protocol or operational method including connection of carbon and alumina assay columns onto the Stage 2 manifold according to an embodiment of the invention. In FIG. 23, the stop cock featured in FIG. 19, for example, is replaced with a fitting, such as, for a non-limiting example, a luer lid adapter for fluidically and reversibly connecting the corresponding assay column to the Stage 2 manifold. The luer lid adapter can be disposable particularly where cross contamination is of concern. Alternatively, the luer lid adapter can be reusable.

FIG. 24 shows a system and steps for a sample elution of Stage 2 of the invention according to an embodiment of the invention. FIG. 24 features the luer lid adapter shown in FIG. 23.

Figure 25:
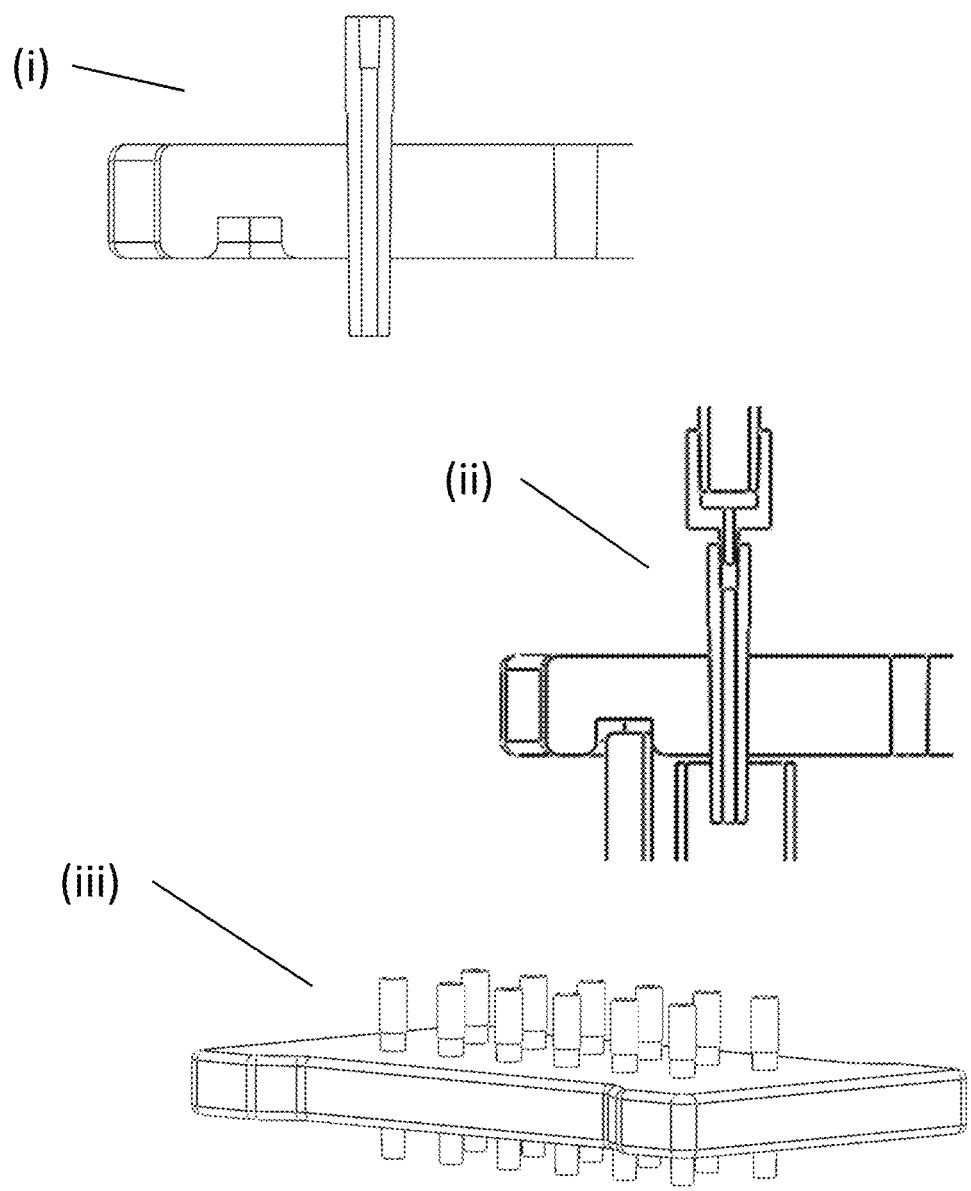
FIG. 25 includes sectional (i, ii) and perspective (iii) views of the luer lid adapter shown in FIGS. 23 and 24 in accordance with an embodiment of the invention.

FIG. 25 shows sectional (i, ii) and perspective (iii) views of the luer lid adapters shown in FIGS. 23 and 24.

Figure 26:
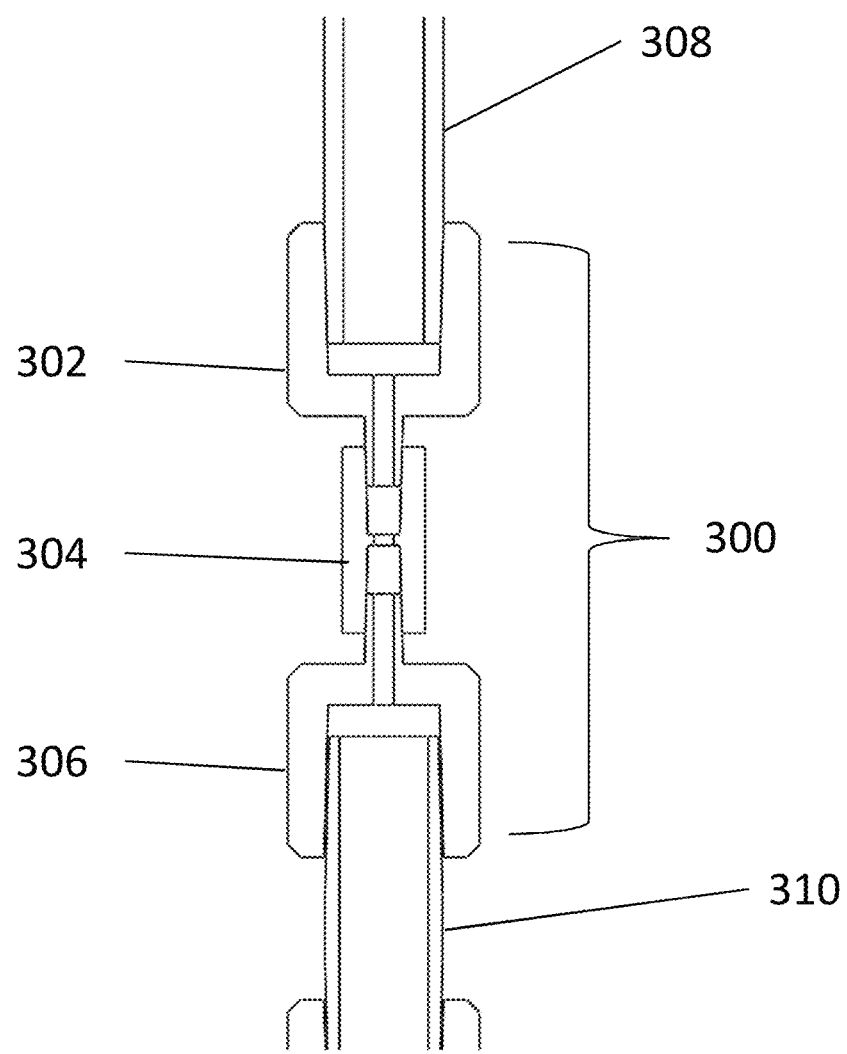
FIG. 26 is a sectional view of an easy connect fitting in accordance with an embodiment of the invention.

FIG. 26 shows a sectional internal view of an easy connect mechanism for fluidic and reversible connection between two assay columns (308) and (310) according to an embodiment of the invention. The easy connection fitting or mechanism (300) includes easy connect fittings (302) and (306) fluidically and reversibly connected to respective assay columns (308) and (310) and further includes easy connect fitting (304) fluidically and reversibly connecting easy connect fitting (302) to easy connect fitting (306). The easy connect fitting (304) acts as a union for fluidically and reversibly connecting the easy connect fitting (302) and the easy connect fitting (306). The easy connect fitting (304) includes a female portion or female union machined in a body of the easy connect fitting (304) at opposing ends. The male portion or male luer of the easy connect fitting (302) fluidically and reversibly connects with the first female portion or female luer of the easy connect fitting (304) and the male portion or male luer of the easy connect fitting (306) fluidically and reversibly connects with the second female portion or female luer of the easy connect fitting (306).

Figure 27:
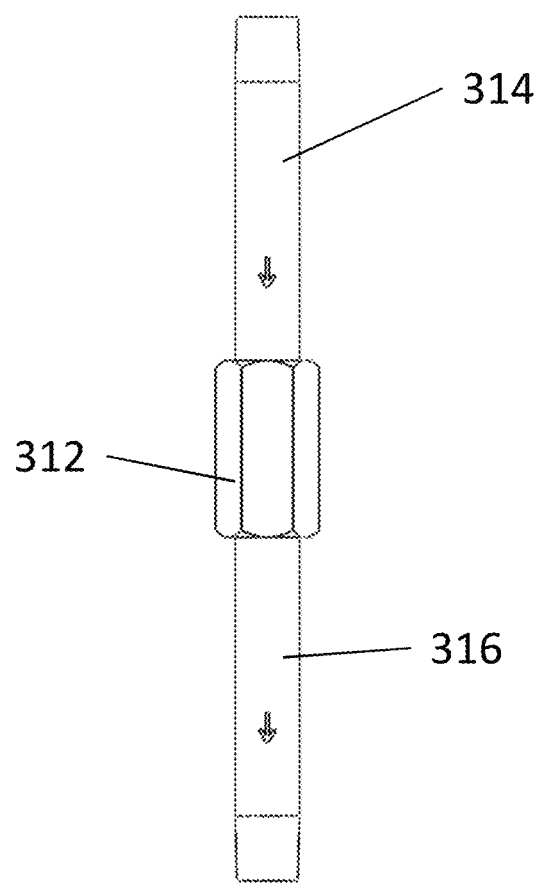
FIG. 27 is an elevation side view of two assay columns connected with a single component easy connect fitting in accordance with an embodiment of the invention.

FIG. 27 shows a schematic external representation of easy connect fitting (312) where two assay columns (314, 316) are fluidically and reversibly connected with a single component easy connect fitting (312).

Figure 28:
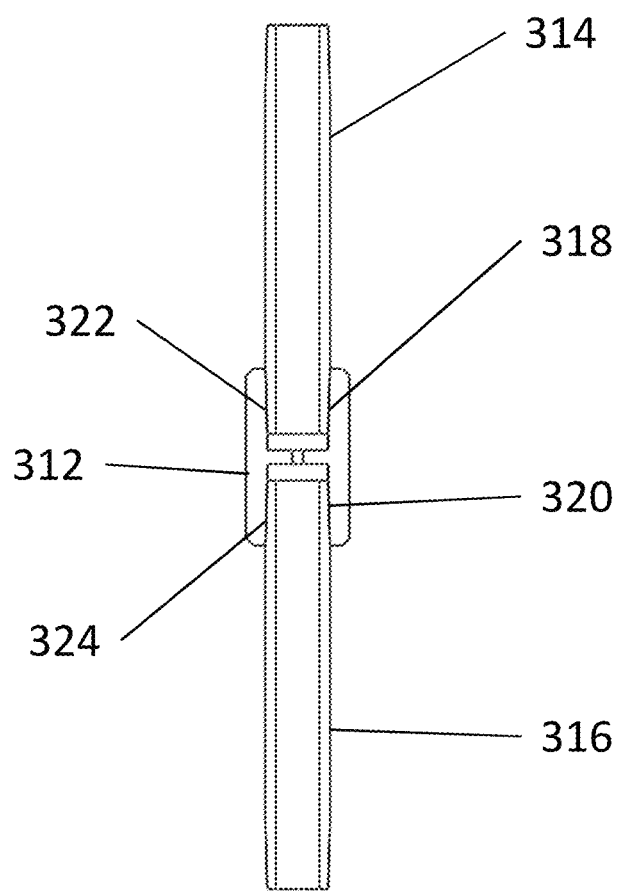
FIG. 28 is a sectional view of a single component easy connect for connecting two assay columns in accordance with an embodiment of the invention.

FIG. 28 shows a sectional view of the single component easy connect fitting (312) described above in the context of FIG. 27 for fluidically and reversibly connecting two assay columns (314) and (316) according to an embodiment of the invention. The single component easy connect fitting (312) includes female portions or female luers (318, 320) machined into a body of the easy connect fitting (312) on opposing ends, each female portion female luer being adapted for fluidically and reversible connecting with a corresponding assay column. Assay column 314 has an end having a male portion or male luer (322) which is tapered and connects fluidically and reversibly with the female portion or female luer (318) of the single component easy connect fitting (312). Assay column 316 has an end having a male portion or male luer (324) which is tapered and connects fluidically and reversibly with the female portion or female luer (320) of the single component easy connect fitting (312).

In different embodiments, the easy connect fittings (302, 304, 306 and 312) can be re-useable, disposable or combinations thereof.

FIGS. 29-58 show the compact vacuum system and method for liquid extraction and purification accordingly to alternative embodiments of the invention including alternative Stage 1 and Stage 2 configurations, alternative Stage 1 solvent and Stage 2 solvent reservoir adapters and holders, a lengthened Stage 1 manifold incorporating a vacuum relief valve, lid incorporation of a manifold vacuum port, a vacuum gauge and a vacuum relief valve, and a new 3-way valve bracket.

Figure 29A:
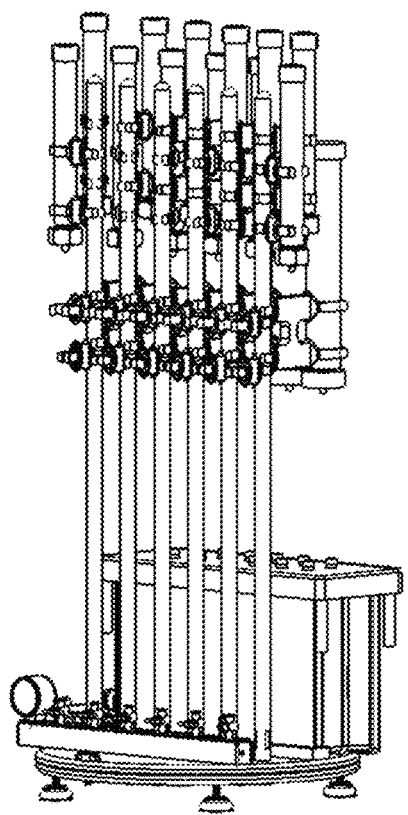
FIGS. 29A and 29B are perspective views of Stage 1 configurations, where assay column assemblies are not yet installed, in accordance with alternative embodiments of the invention.
Figure 29B:
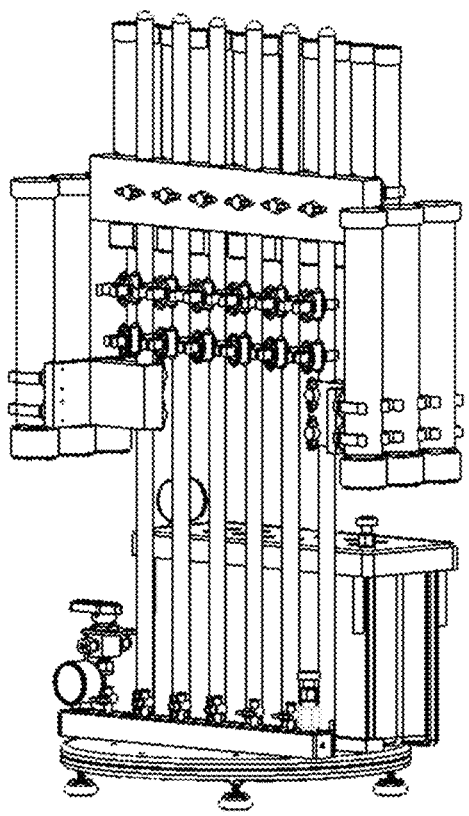
Figure 30A:
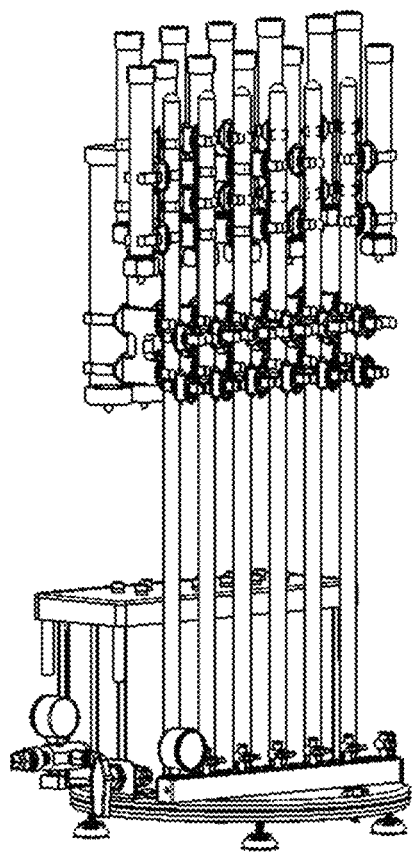
FIGS. 30A and 30B are perspective views of Stage 1 configurations, where assay column assemblies are not yet installed, in accordance with alternative embodiments of the invention.
Figure 30B:
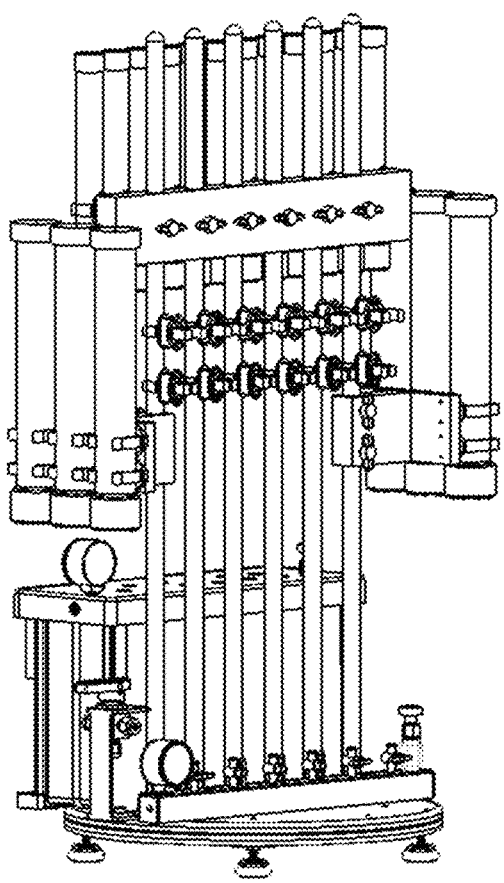

FIGS. 29-30 show overall perspective views of Stage 1 configurations not including assay column assemblies according to alternative embodiments A and B of the invention.

Figure 31A:
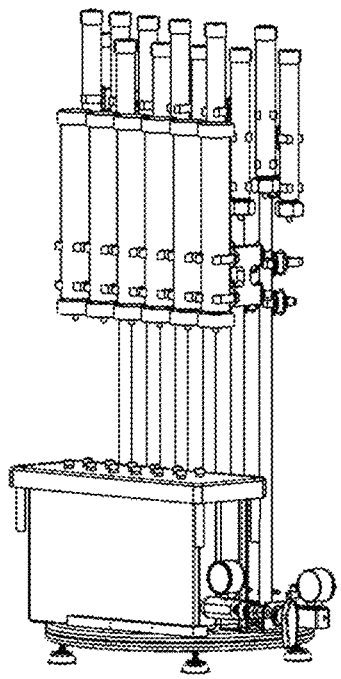
FIGS. 31A and 31B are perspective views of Stage 2 configurations, where assay column assemblies are not yet installed, in accordance with alternative embodiments of the invention.
Figure 31B:
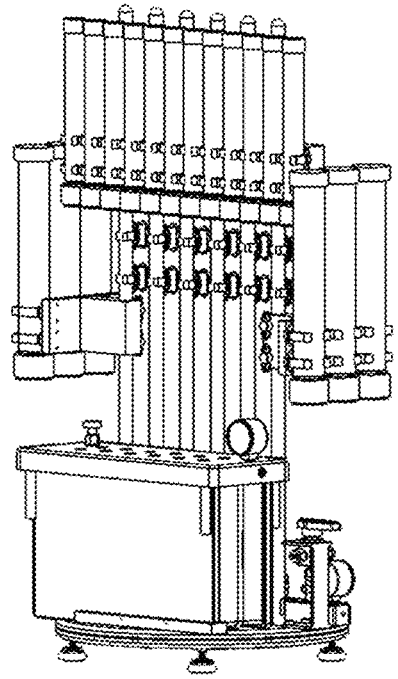
Figure 32A:
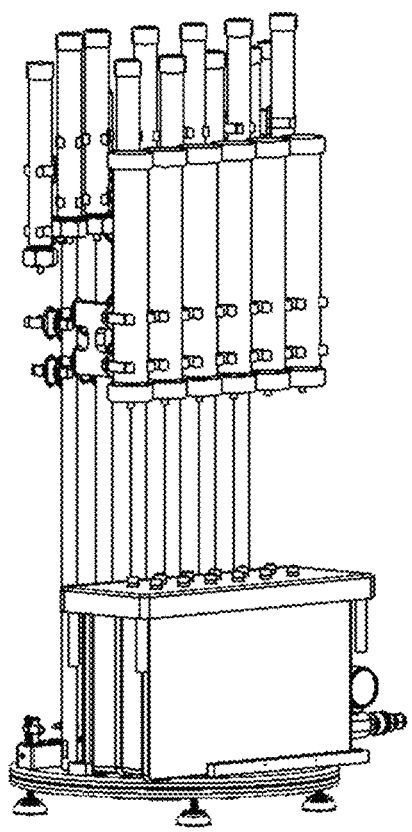
FIGS. 32A and 32B are perspective views of Stage 2 configurations, where assay column assemblies are not yet installed, in accordance with alternative embodiments of the invention.
Figure 32B:
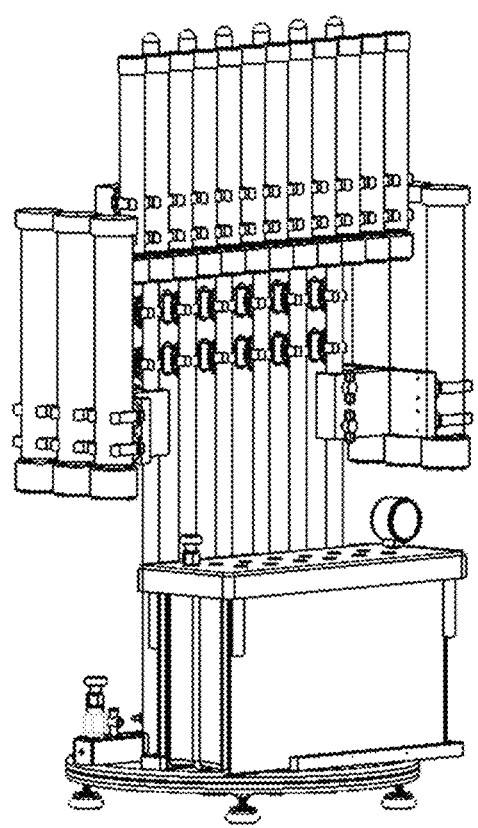

FIGS. 31-32 show overall perspective views of Stage 2 configurations not including assay column assemblies according to alternative embodiments A and B of the invention.

Figure 33A:
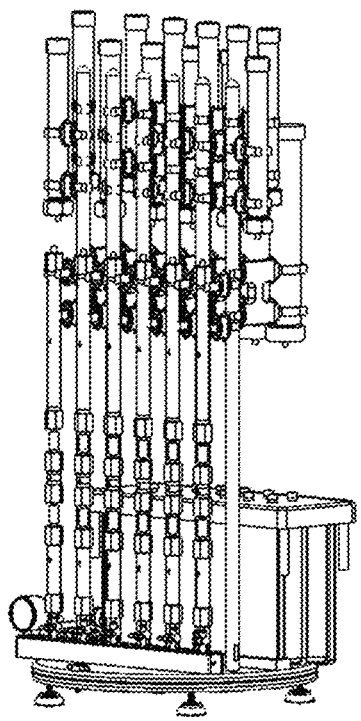
FIGS. 33A and 33B are perspective views of Stage 1 configurations including Stage 1 assay column assemblies, in accordance with alternative embodiments of the invention.
Figure 33B:
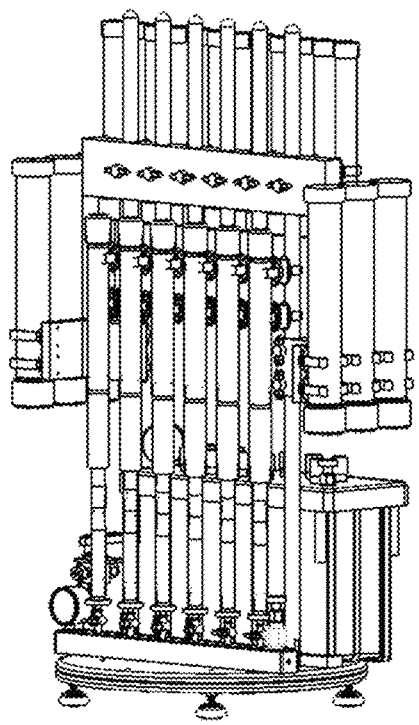

FIG. 33 shows overall perspective views of the Stage 1 configurations including Stage 1 assay column assemblies according to alternative embodiments A and B of the invention. The Stage 1 configurations includes components for a vacuum liquid extraction and purification system which can be used to test a variety of solid and semi-solid samples for the presence of any of a number of trace substances.

Figure 34A:
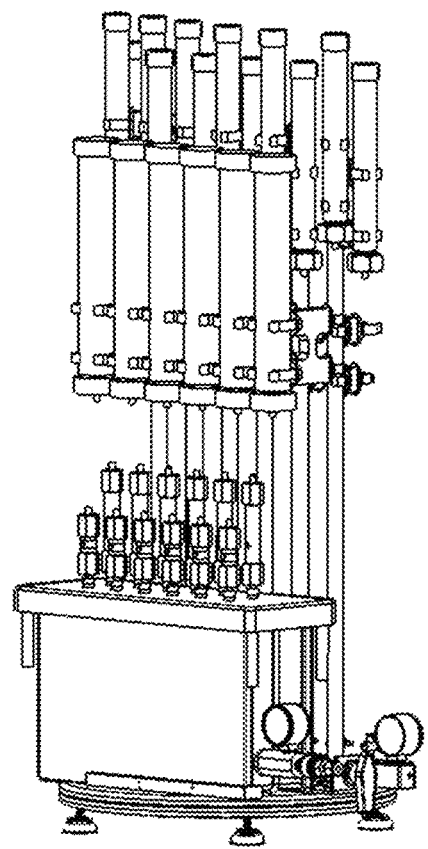
FIGS. 34A and 34B are perspective views of Stage 2 configurations including Stage 2 assay column assemblies, in accordance with alternative embodiments of the invention.
Figure 34B:
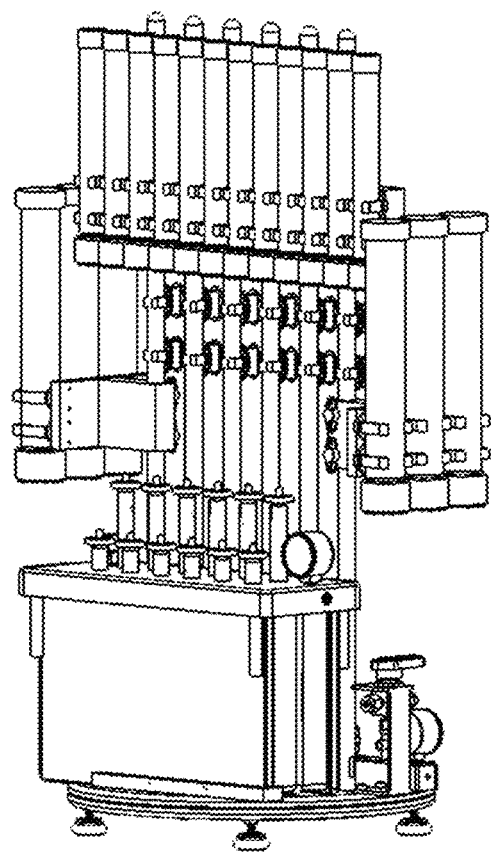

FIG. 34 shows perspective views of Stage 2 configurations including Stage 2 assay column assemblies according to alternative embodiments A and B of the invention.

Figure 35A:
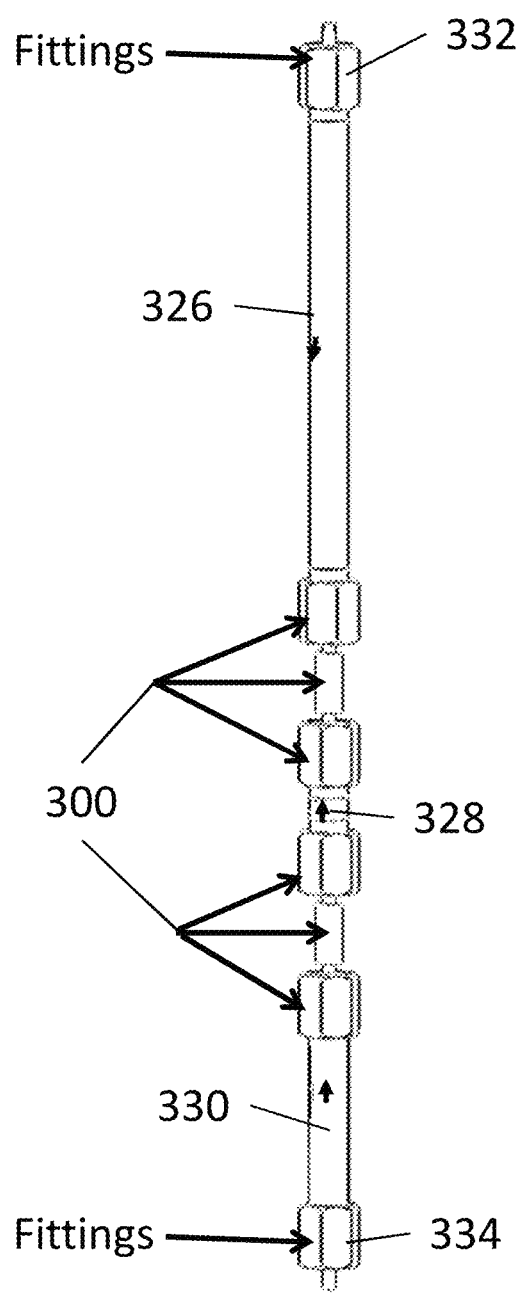
FIGS. 35A, 35B(i) and 35B(ii) are perspective views of Stage 1 column assemblies in accordance with alternative embodiments of the invention.

FIG. 35 shows perspective views of Stage 1 column assemblies, according to alternative embodiments A and B of the invention. Embodiment A is shown including a regularly-sized column. Embodiment B is shown including a jumbo-sized silica column (i) and/or including a regularly-sized silica column (ii). The jumbo-sized column has a larger nominal outside diameter or O.D. and nominal inside diameter or I.D. as compared to a regularly-sized column.

Throughout the application, in non-limiting embodiments, the jumbo-sized column preferably has a nominal O.D. in a range of 0.87 to 0.88 inches and more preferably a nominal O.D. of 0.875 inches, and preferably a nominal I.D. in a range of 0.713 to 0.723 inches and more preferably a nominal I.D. of 0.718 inches. In non-limiting embodiments, the regularly-sized column preferably has a nominal O.D. in a range of 0.535 to 0.545 inches and more preferably a nominal O.D. of 0.540 inches and preferably has a nominal I.D. of 0.364 to 0.375 inches, and more preferably a nominal I.D. of 0.369 inches. Jumbo- or regularly-sized columns are selected depending on the application.

The column assembly of embodiment A is shown with three assay columns (326, 328 and 330) stacked on top of one another. The three assay columns are fluidically and reversibly connected to one another via easy connect fittings (300) as described above in the context of FIG. 26. Thus, each of the easy connect fittings or mechanisms (300) thus includes three easy connect fittings or components, as described above in the context of FIG. 26. Embodiment A has two easy connect fittings for respective fluidic and reversible connection to the solvent reservoir and to the Stage 1 manifold. The easy connect fitting (332) to the solvent reservoir can be similar to the easy connect fitting (162) shown for example in FIG. 7A. The east connect fitting (334) can be similar to the easy connect fitting (190) shown for example in FIG. 9A.

Figure 35B:
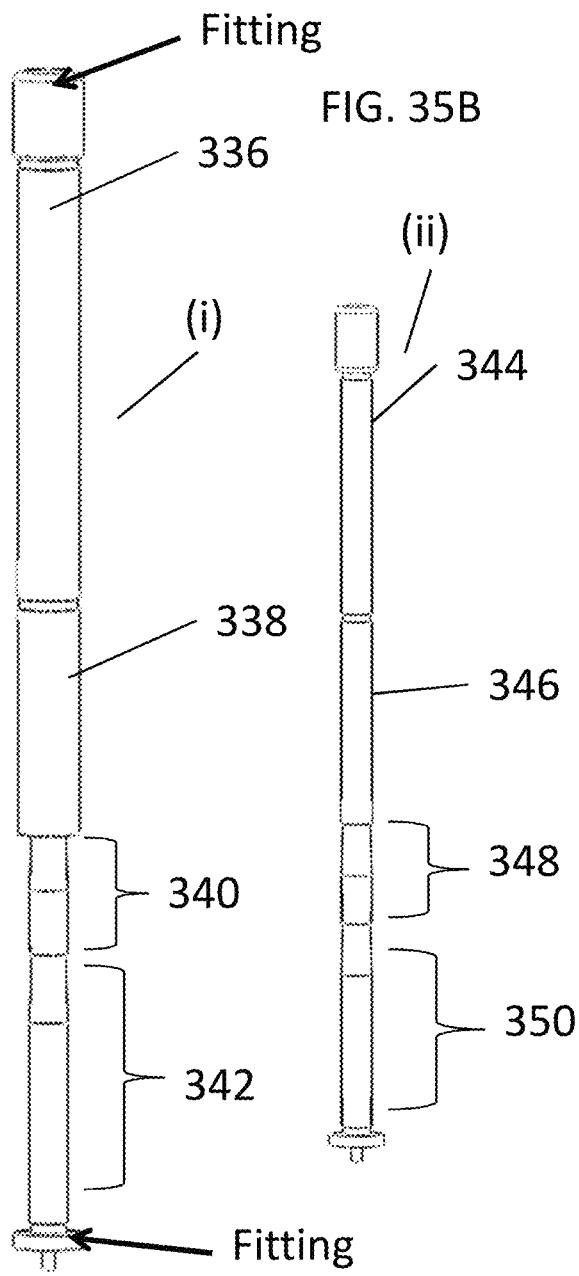

The column assemblies of alternative embodiments B each have two easy connect fittings for fluidic and reversible connection respectively to the solvent reservoir and the Stage 1 manifold. Embodiment B (i) shows four assay columns stacked in series. Each of the columns include a female portion or luer and a male portion or luer machined into the body of the respective assay column. Thus, the columns can be stacked with male portions or luers feeding to female portions or luers for fluidic and reversible connection. Assay column 336 and 338 are shown as jumbo-sized columns, according to non-limiting exemplary embodiments. In exemplary non-limiting embodiments, assay columns 336 and 338 can include respectively silica and basic/neutral material. Assay columns 340 and 342 are shown as regularly-sized assay columns according to non-limiting exemplary embodiments. In non-limiting exemplary embodiments, columns 340 and 342 can include respectively carbon material alumina material. FIG. 35B (ii) shows a similar stackable column assembly as FIG. 35B (i) but having all the assay columns including regularly-sized assay columns, according to an exemplary, non-limiting embodiment.

Figure 36A:
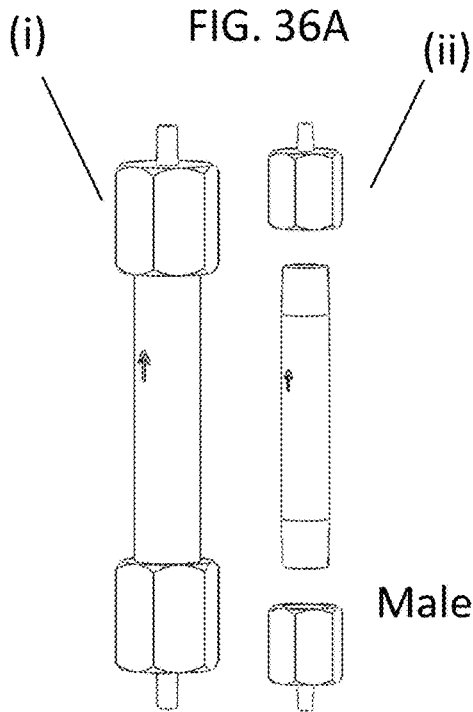
FIG. 36A includes perspective (i) and exploded (ii) views of a column assembly in accordance with alternative embodiments of the invention.
Figure 36B:
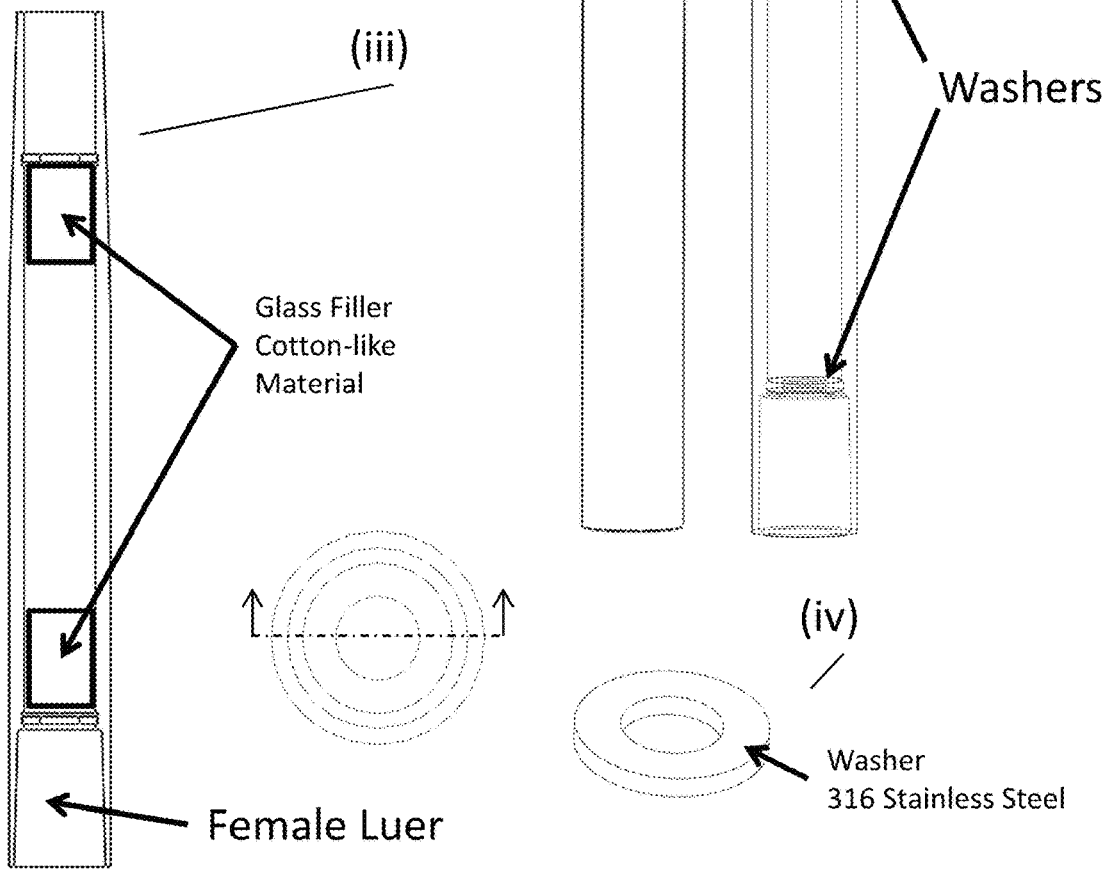
FIG. 36B includes perspective (i) and sectional (i, ii) views of a column assembly and FIG. 36B (iv) a perspective view of a washer in accordance with alternative embodiments of the invention.

FIGS. 36A and 36B shows assay column assemblies, such as, for non-limiting examples, carbon or alumina filled assay columns, according to alternative embodiments A and B of the invention. Embodiment A features assay column assemblies including easy connect fittings disposed on opposing ends of the assay column, as shown in the perspective (i) and exploded (ii) views of FIG. 36A. Embodiment A can include regularly-sized columns or jumbo-sized columns, as necessary for a particular application.

Embodiment B features assay columns having a male portion disposed on one end of the assay columns and a female portion disposed at an opposing end of the assay column, as shown in FIGS. 36B (i, ii iii). The male portion can include a tapering of the column on an exterior surface of the male portion, as shown in FIG. 36B (i). The male portion can also include a male luer disposed in an interior of the male portion, as shown in, for example, FIG. 36B (ii). The female portion can include a female luer disposed in an interior of the female portion, as shown in FIGS. 36B (ii and iii). The customized male and female luers are adapted for connecting the assay columns without additional components. In different variations of embodiment B, a washer is seated within an internal groove disposed at one or both opposing ends of the respective column, as shown, for example, in the sectional view of FIG. 36B (ii). The washers can prevent re-packing of the assay column material. In a non-limiting example(s), the washer(s) are made of stainless steel, such as 316 stainless steel, as shown in FIG. 36B (iv). In alternative embodiments, filter material such as, for a non-limiting example, a glass cotton or wool like filter material, is disposed adjacent one or both washers on the internal column side of the respective washer, as shown in FIG. 36B (iii). The filter material can assist in holding the column packing material particularly when the column is under vacuum. The washers can also provide support for the filter material. Embodiment B can include regularly-sized or jumbo-sized columns. In exemplary non-limiting embodiments, the assay columns shown as embodiment B include carbon or alumina.

Figure 37:
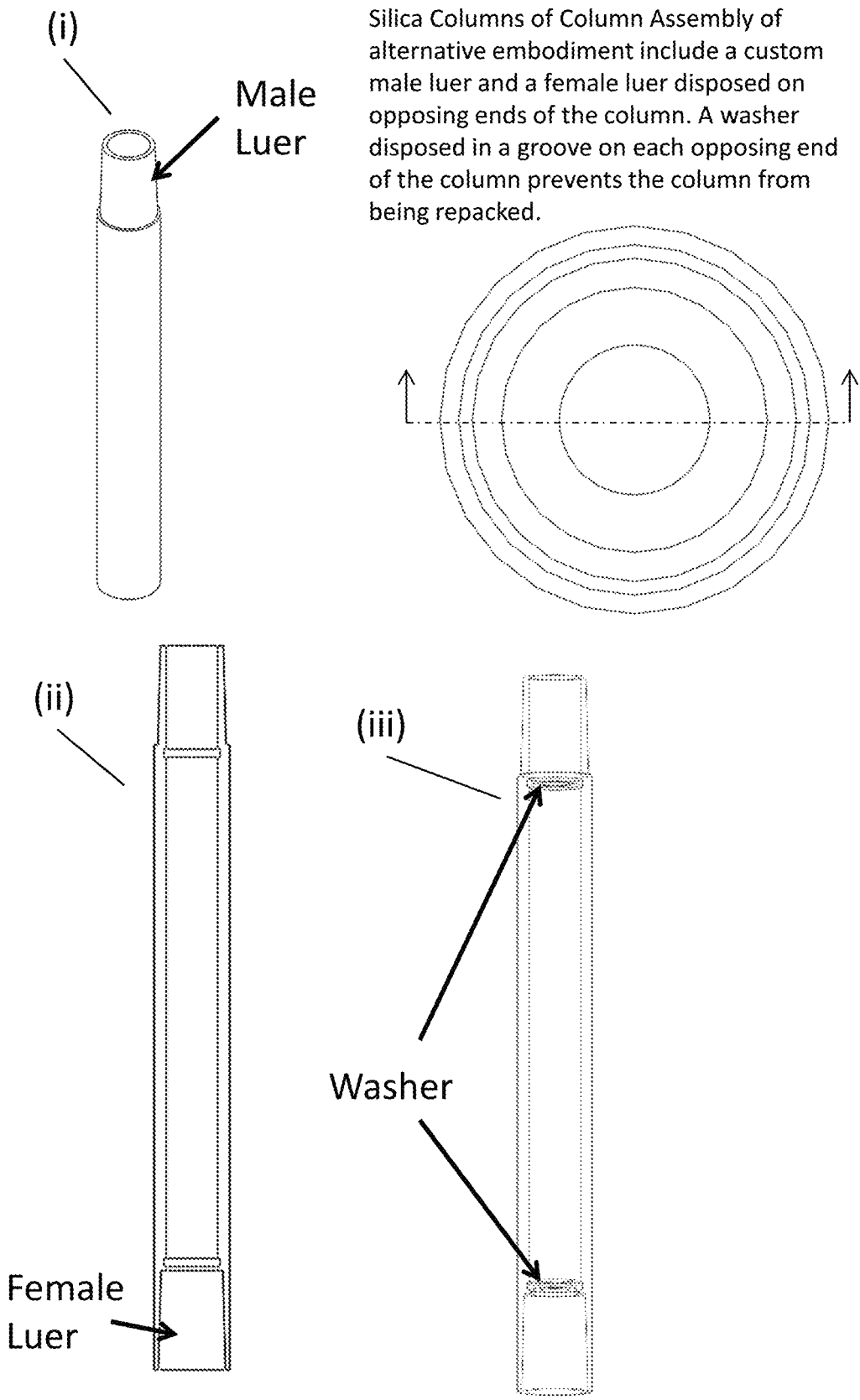
FIG. 37 includes perspective (i) and sectional (ii, iii) views of an assay column assembly in accordance with an embodiment of the invention FIG. 38A and FIG. 38 B are external assembled (FIGS. 38A (i) and 38B (i)), exploded (FIG. 38A (ii)) and sectional (FIG. 38A (ii)) views of jumbo-sized assay columns in accordance with alternative embodiments of the invention.

FIG. 37 shows assay columns according to an alternative embodiment of the invention. This alternative embodiment features the assay column having a custom male luer disposed at one end of the column, as shown in FIG. 37 (*i*) and a custom female luer disposed at the opposing end of the column, as shown in FIG. 37 (*ii*). In alternative embodiments, a washer can be disposed in a groove on at least one and preferably both opposing ends of the assay column, as shown in FIG. 37 (iii), and as discussed above regarding FIG. 36. Such washers can prevent re-packing of the assay column material. In alternative embodiments, filter material such as, for a non-limiting example, a glass cotton or wool like filler material, can be disposed adjacent one or both washers on the internal column side of the respective washer, as discussed above regarding FIG. 36B. The filter material can assist in holding the column packing material particularly when the column is under vacuum. The washers can also provide support for the filter material. The embodiment exemplified in FIG. 37 can include regularly-sized or jumbo-sized columns.

Figure 38A:
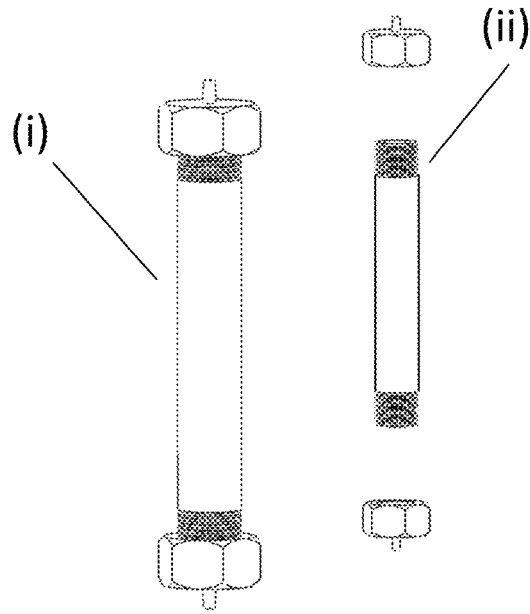
Figure 38B:
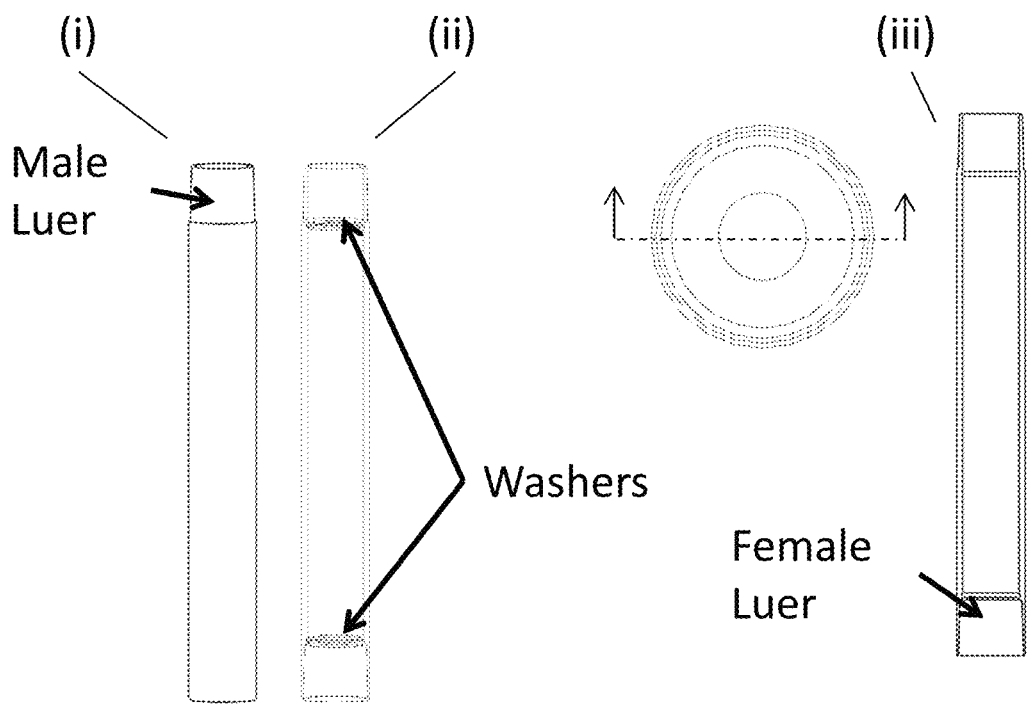

FIG. 38 shows assay column assemblies according to alternative embodiments A and B of the invention. Embodiment A features an assay column having fittings disposed at opposing ends of the column as shown in the perspective (i) and exploded (ii) views of FIG. 38A. Embodiment A can include regularly-sized assay columns or jumbo-sized columns. Embodiment B features an assay column having a male luer and a female luer disposed at opposing ends of the assay column, as shown in the respective perspective (i) and sectional (iii) views of FIG. 38B. Embodiment B can feature a washer disposed in a groove disposed one end and preferably at both opposing ends of the assay column, as shown in the sectional view of FIG. 38B (ii). Such washers can prevent re-packing of the assay column packing material. In alternative embodiments, filler material such as, for a non-limiting example, a glass cotton or wool like filler material, can be disposed adjacent one or both washers on the internal column side of the respective washer, as discussed above regarding FIG. 36B. The filter material can assist in holding the column packing material particularly when the column is under vacuum. The washers can also provide support for the filter material. Embodiment B can include regularly-sized or jumbo-sized assay columns.

Figure 39:
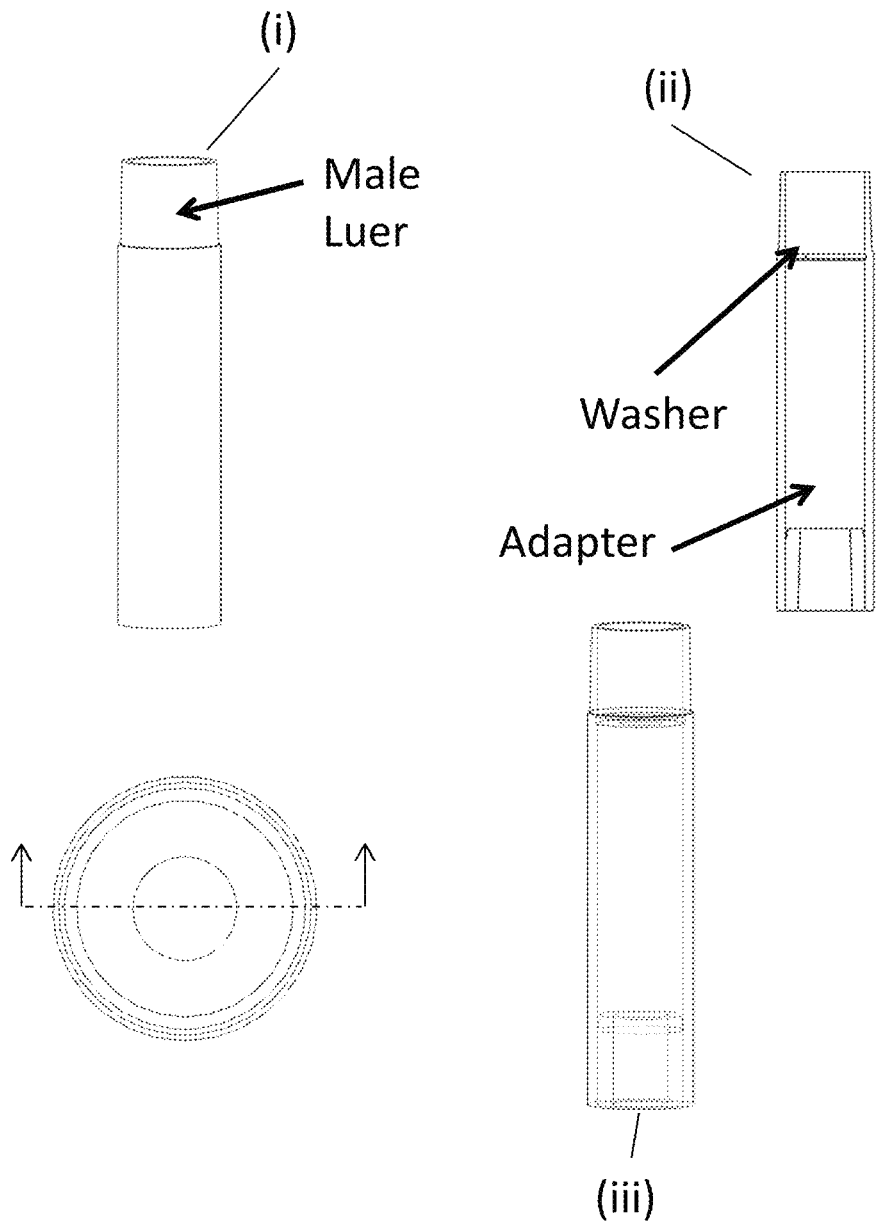
FIG. 39 includes perspective (i) and sectional (ii, iii) views of an assay column in accordance with an embodiment of the invention.

FIG. 39 shows an assay column, such as, for a non-limiting example, neutral or basic silica jumbo-sized assay column, having a male luer disposed at one end of the column and an adapter disposed at the opposing end of the column, according to an alternative embodiment of the invention. The adapter is configured for a press fit fluidic and reversible connection to another column, such as, for a non-limiting example, a carbon column. The neutral or basic silica jumbo-sized column has a groove for seating washer on the male luer end of the column. In different embodiments, the adapter can be used with a regularly-size column.

Figure 40:
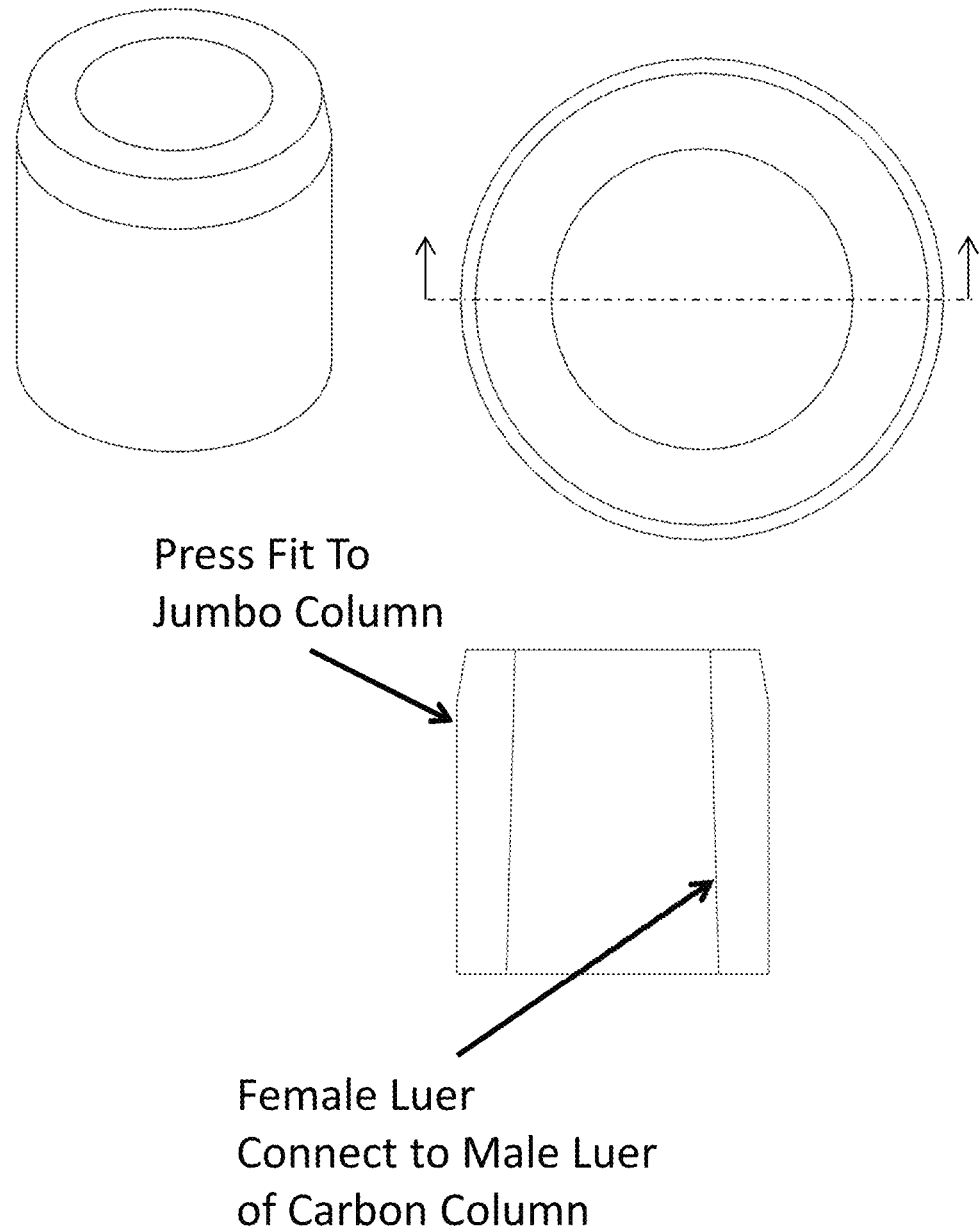
FIG. 40 includes views of an adapter configured for positioning at an end of an assay column in accordance with an embodiment of the invention.

FIG. 40 shows another view of the adapter shown in FIG. 39. The adapter is configured on a first end for a fluidic and reversible press fit into a connecting column, such as, for a non-limiting example, a neutral or basic silica jumbo-sized assay column. The adapter is configured on a second end as a female luer for a fluidic and reversible connection with a male luer of a connecting assay column, such as, for a non-limiting example, a carbon assay column. The adapter can also act as a bottom washer for the connecting assay column, such as the neutral or basic silica jumbo-sized assay column.

Figure 41:
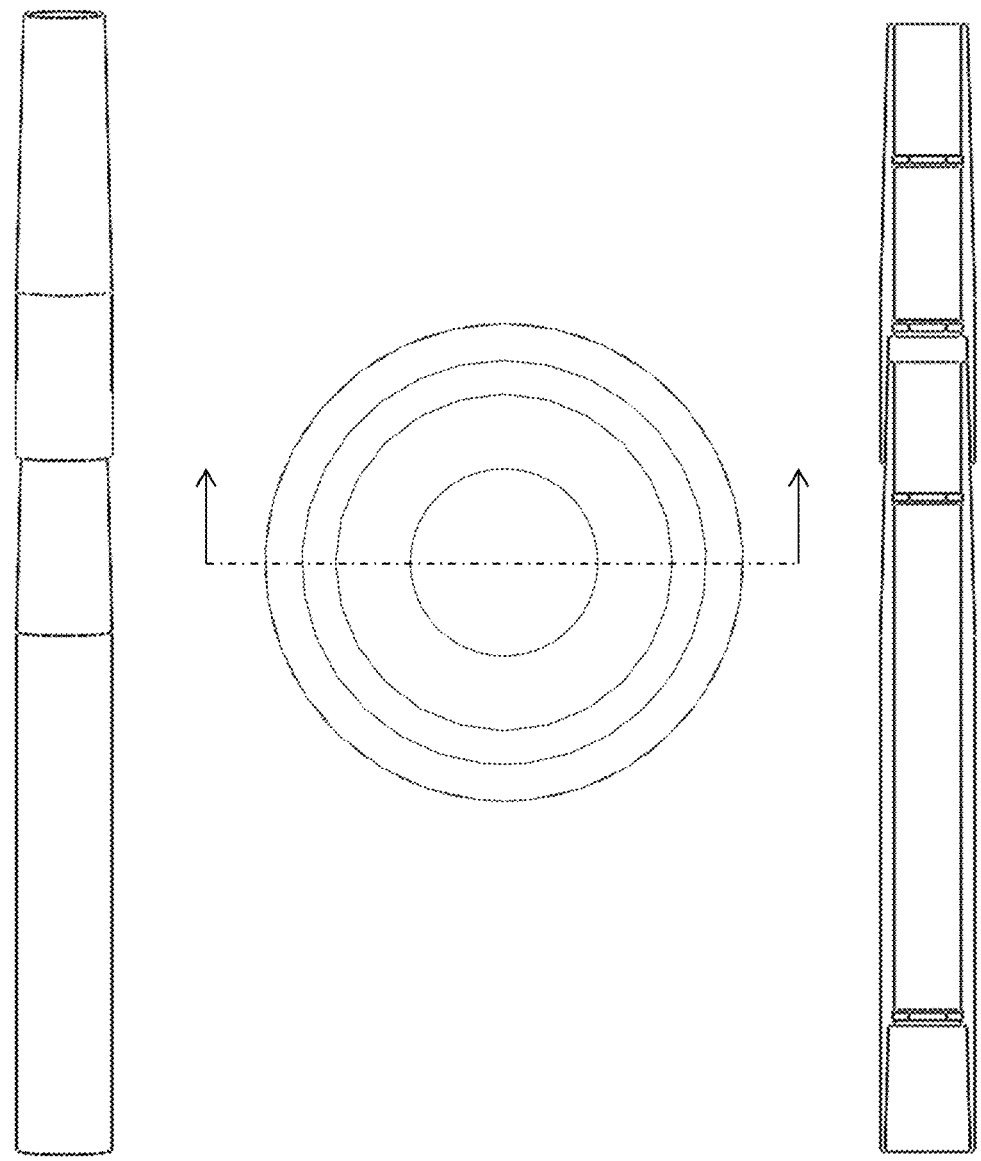
FIG. 41 includes external and sectional side views of interconnecting assay columns, in accordance with an embodiment of the invention.

FIG. 41 shows assay columns fluidically and reversibly connected by the male luer fitting into the female luer, where each of the luers have been machined into their respective column, according to an alternative embodiment of the invention.

Figure 42:
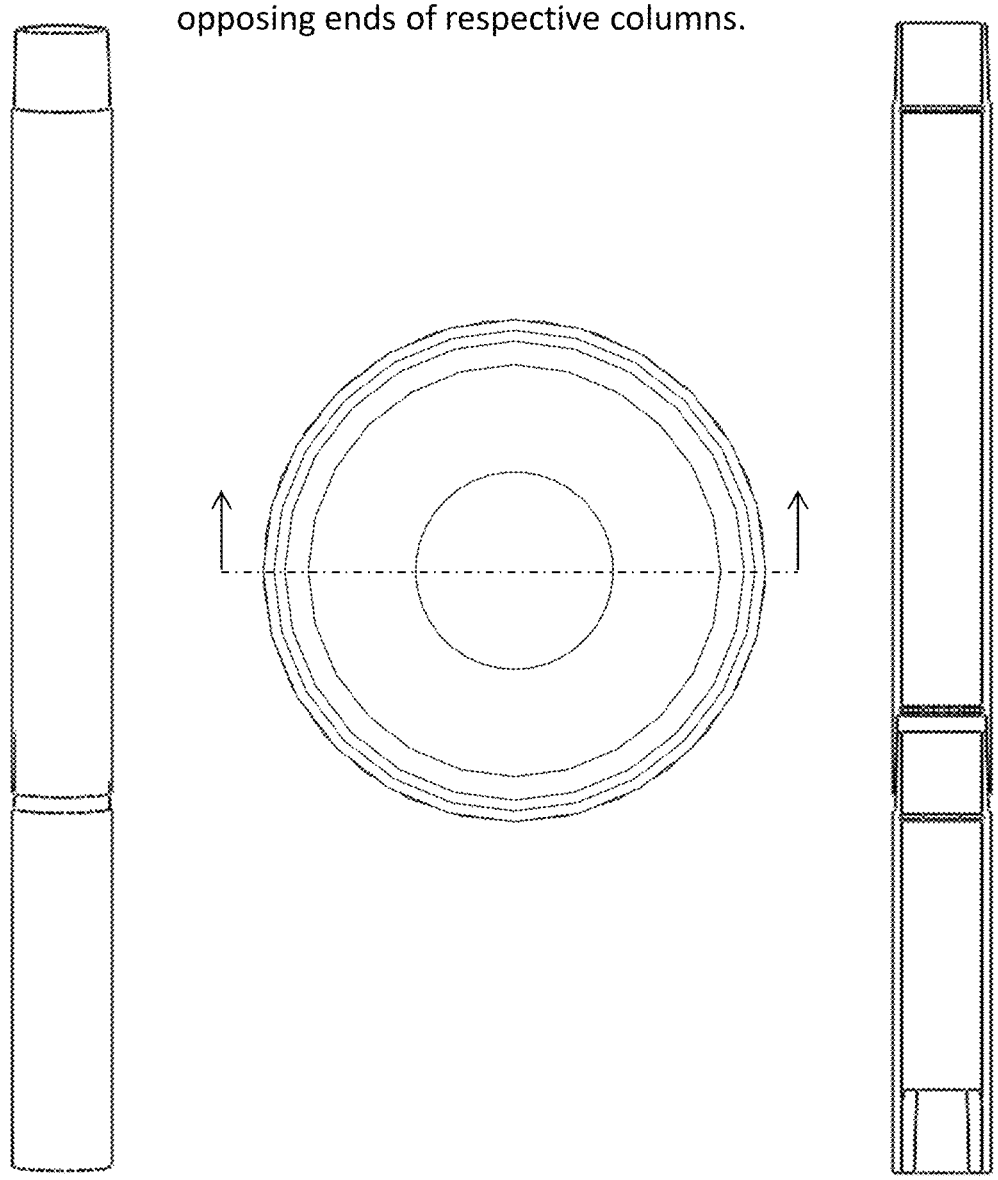
FIG. 42 includes external and sectional side views of interconnecting jumbo-sized assay columns, in accordance with an embodiment of the invention.

FIG. 42 shows jumbo-sized assay columns fluidically and reversibly connected by the male luer fitting into the female luer, where each of the luers have been machined into their respective column, according to an alternative embodiment of the invention.

Figure 43:
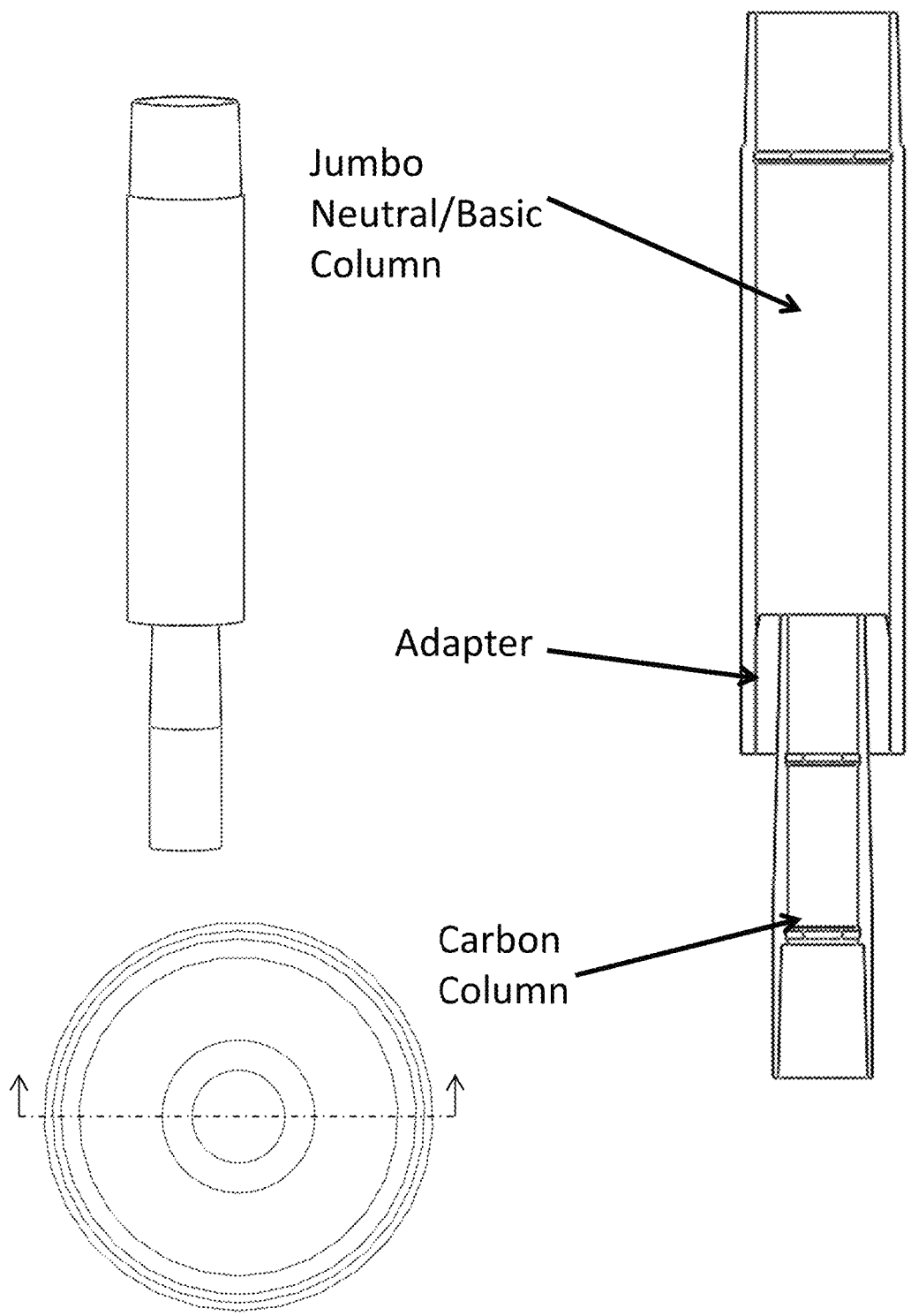
FIG. 43 includes external and sectional side views of interconnecting jumbo-sized assay columns, in accordance with an embodiment of the invention.

FIG. 43 shows a sectional view of an assay column assembly including an assay column, such as for a non-limiting example, a neutral or basic jumbo-sized assay column, having a male luer at one end and an adapter at the opposing end being connected to a male luer of a connecting column, such as, for a non-limiting example, a carbon column, according to an alternative embodiment of the invention.

Figure 44:
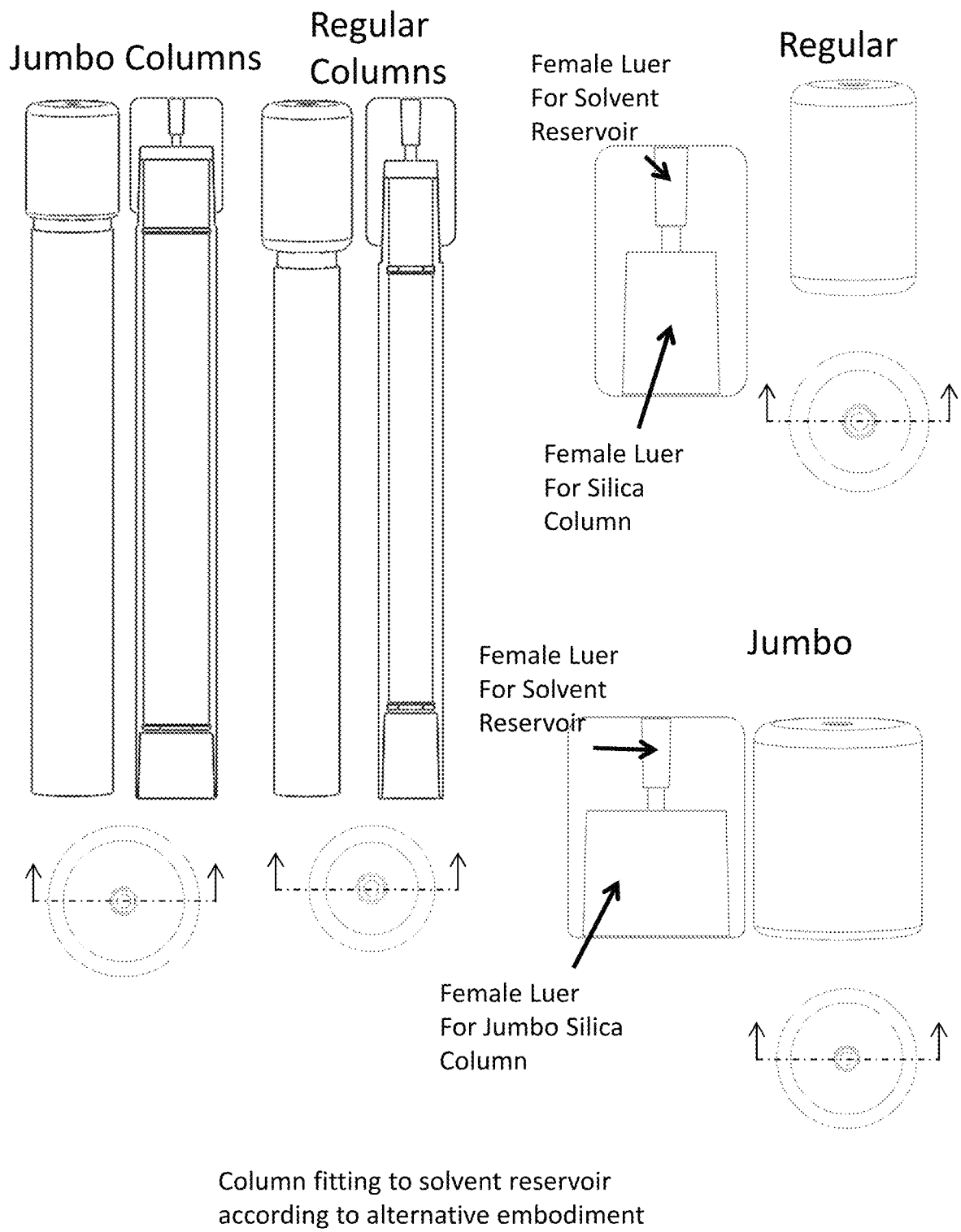
FIG. 44 includes external and sectional views of assay column to solvent reservoir fittings, in accordance with alternative embodiments of the invention.

FIG. 44 shows an assay column fitting to a solvent reservoir, according to an alternative embodiment of the invention. The solvent reservoir has a female luer. The connecting column, such as, for non-limiting examples, a regularly-sized silica column or a jumbo-sized silica column, has a female luer. Each of the solvent reservoir female luer and the connecting column female luer can be reversibly fitted into a male luer thereby providing fluidic flow between the solvent reservoir and the connecting column.

Figure 45:
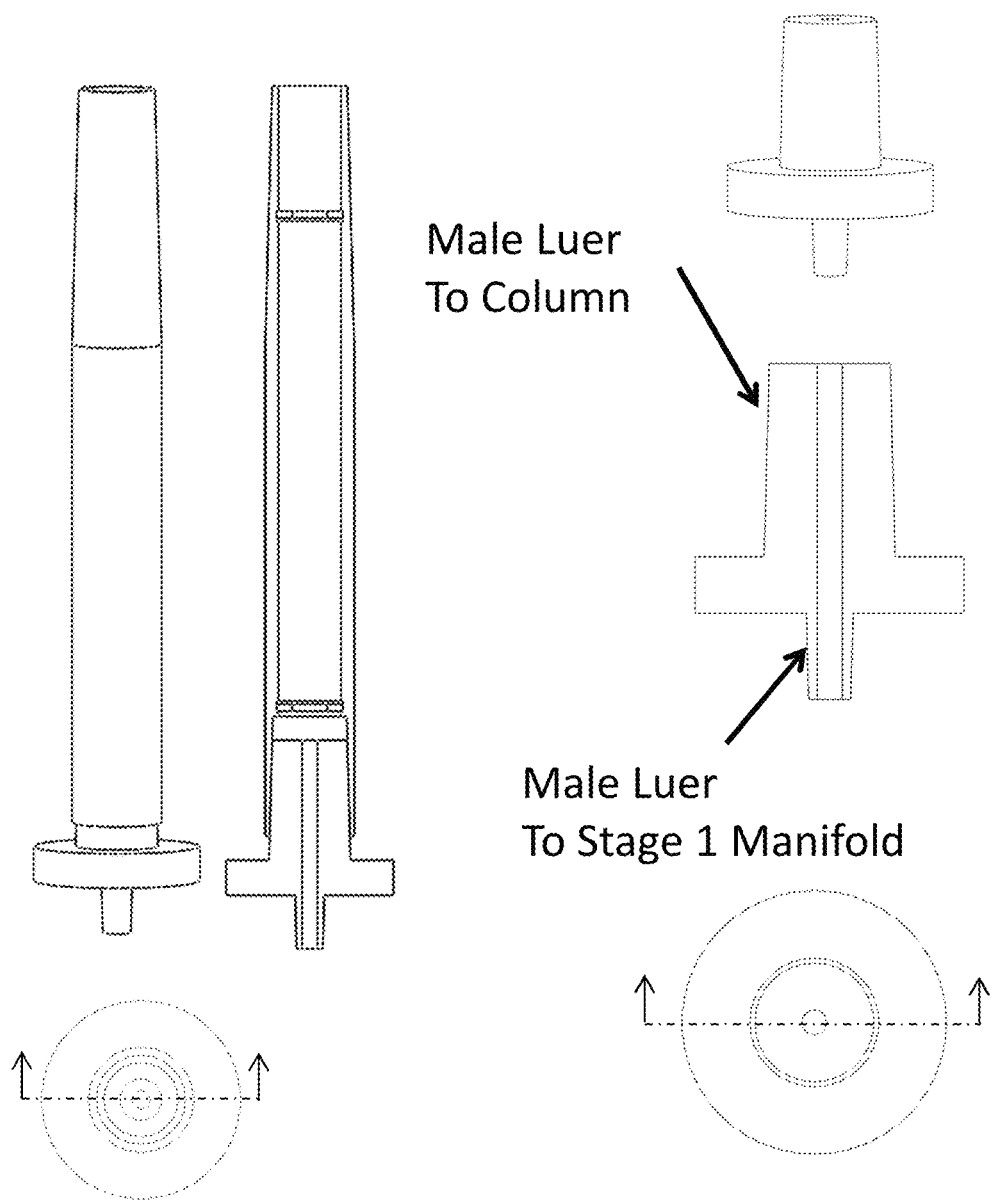
FIG. 45 includes external and sectional views of an assay column to Stage 1 Manifold fitting, in accordance with an embodiment of the invention.

FIG. 45 shows the column fitting for reversibly connecting an assay column to the Stage 1 manifold, according to an alternative embodiment of the invention. The column fitting is equipped with a male luer passing through the column fitting which permits fluidic flow upon installation of the column fitting for connection of the assay column to the Stage 1 manifold.

Figure 46A:
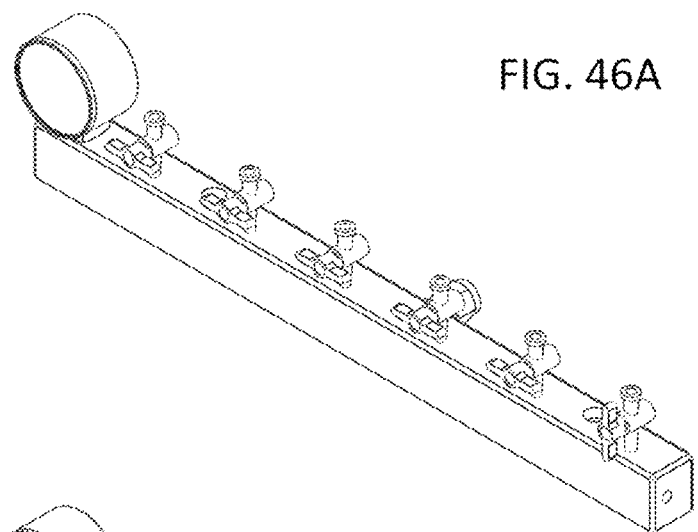
FIGS. 46A and 46B are perspective views of Stage 1 Manifolds, in accordance with alternative embodiments of the invention.
Figure 46B:
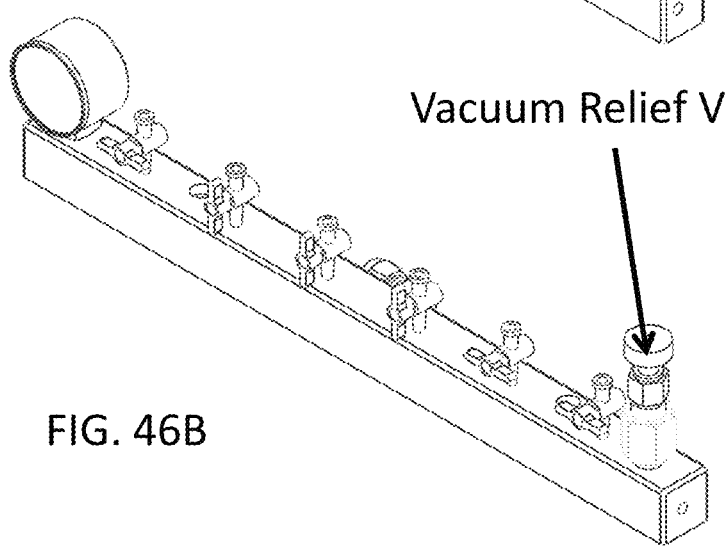

FIG. 46 shows the Stage 1 manifold, according to an embodiment A and an alternative embodiment B of the invention. In contrast with embodiment A, the alternative embodiment B Stage 1 Manifold additionally includes a vacuum relief valve. The vacuum relief valve allows the user or operator to adjust the vacuum during the operation of a Stage 1 protocol to maintain optimal flow through the Stage 1 configuration.

FIG. 47 shows a Stage 1 or large solvent reservoir having an adapter including a bottom male luer, according to an embodiment A of the invention, as compared to a Stage 1 or large solvent reservoir adapter having a flat bottom port sized to receive tubing, according to an alternative embodiment B of the invention. In a preferred embodiment, the flat bottom port has a ¼-28 bottom port for secure attachment of tubing.

FIG. 48 shows a Stage 2 or small solvent reservoir having an adapter including a male luer, according to an embodiment A of the invention, as compared to a Stage 2 or small solvent reservoir having an adapter including a flat bottom port sized to receive tubing, according to an alternative embodiment B of the invention. In a preferred embodiment, the flat bottom port has a ¼-28 bottom port.

FIG. 49 shows a large reservoir holder having one or more large reservoir attachments or clips and one or more turn table rod attachments or clips, according to an embodiment A of the invention. FIG. 49 also shows a large reservoir holder having one or more large reservoir holding attachments or clips affixed to a bracket having a pass-through hole for a turn table rod, according to an alternative embodiment B of the invention. The large reservoir holder can be moved in a vertical direction up and down the turn table rod and tightened in place with one or more thumb screws passing through one or more corresponding thumb screw holes. The bracket can also be rotated in a horizontal plane for optimal user access.

Figure 50:
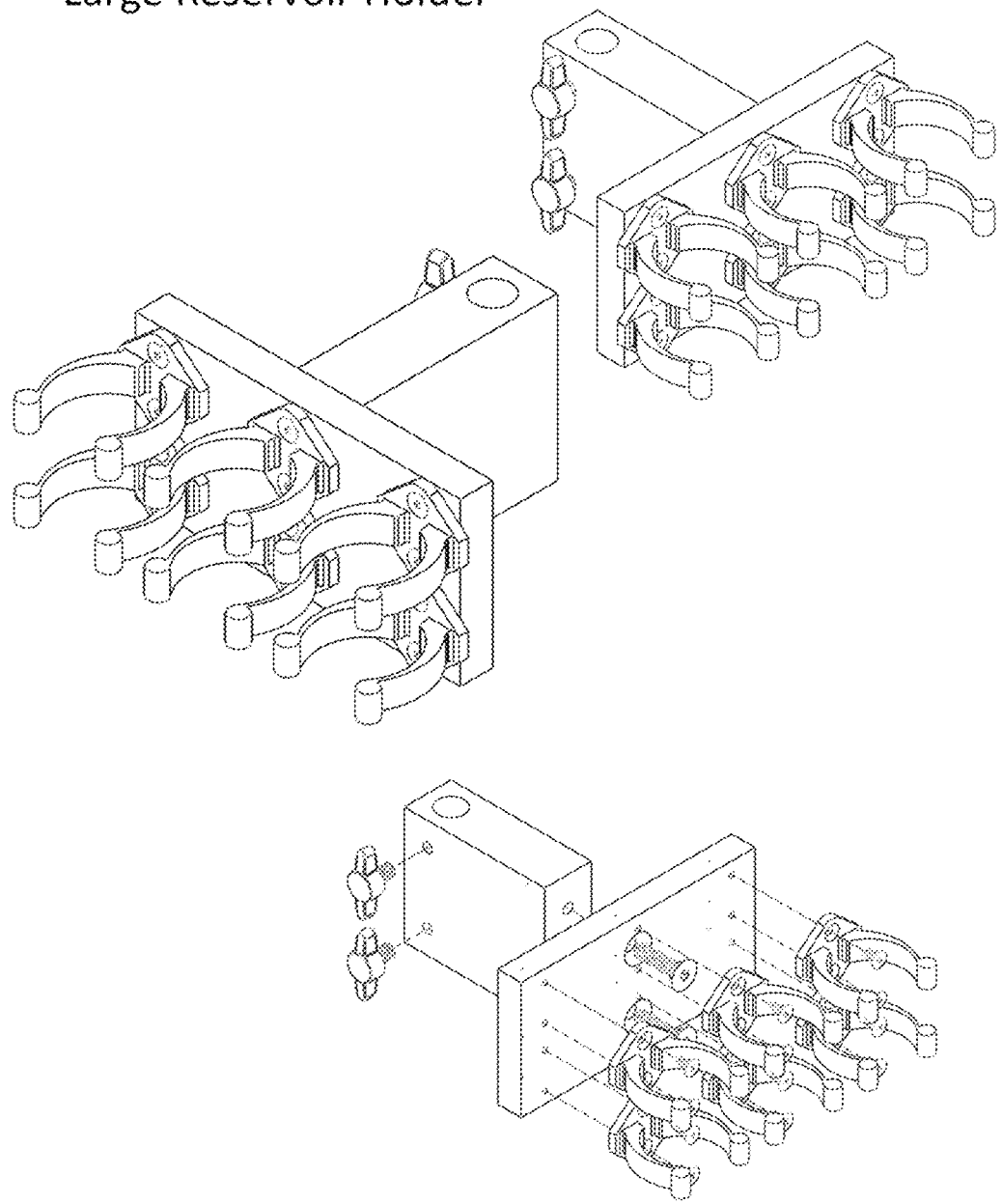
FIG. 50 includes non-exploded and exploded views of large reservoir holders, in accordance with an embodiment of the invention.

FIG. 50 shows non-exploded and exploded views of the large reservoir holder, according to alternative embodiments of the invention.

FIG. 51 shows a small reservoir holder having one or more small reservoir attachments or clips and one or more turn table rod attachments or clips, according to an embodiment A of the invention. FIG. 51 also shows a small reservoir holder having one or more small reservoir attachments or clips affixed to a bracket having one or more pass through holes for one or more corresponding turn table rods, according to an alternative embodiment B of the invention. The small reservoir holder can be moved in a vertical direction up and down the one or more corresponding turn table rods and tightened in place with one or more thumb screws passing through one or more corresponding thumb screw holes.

Figure 52:
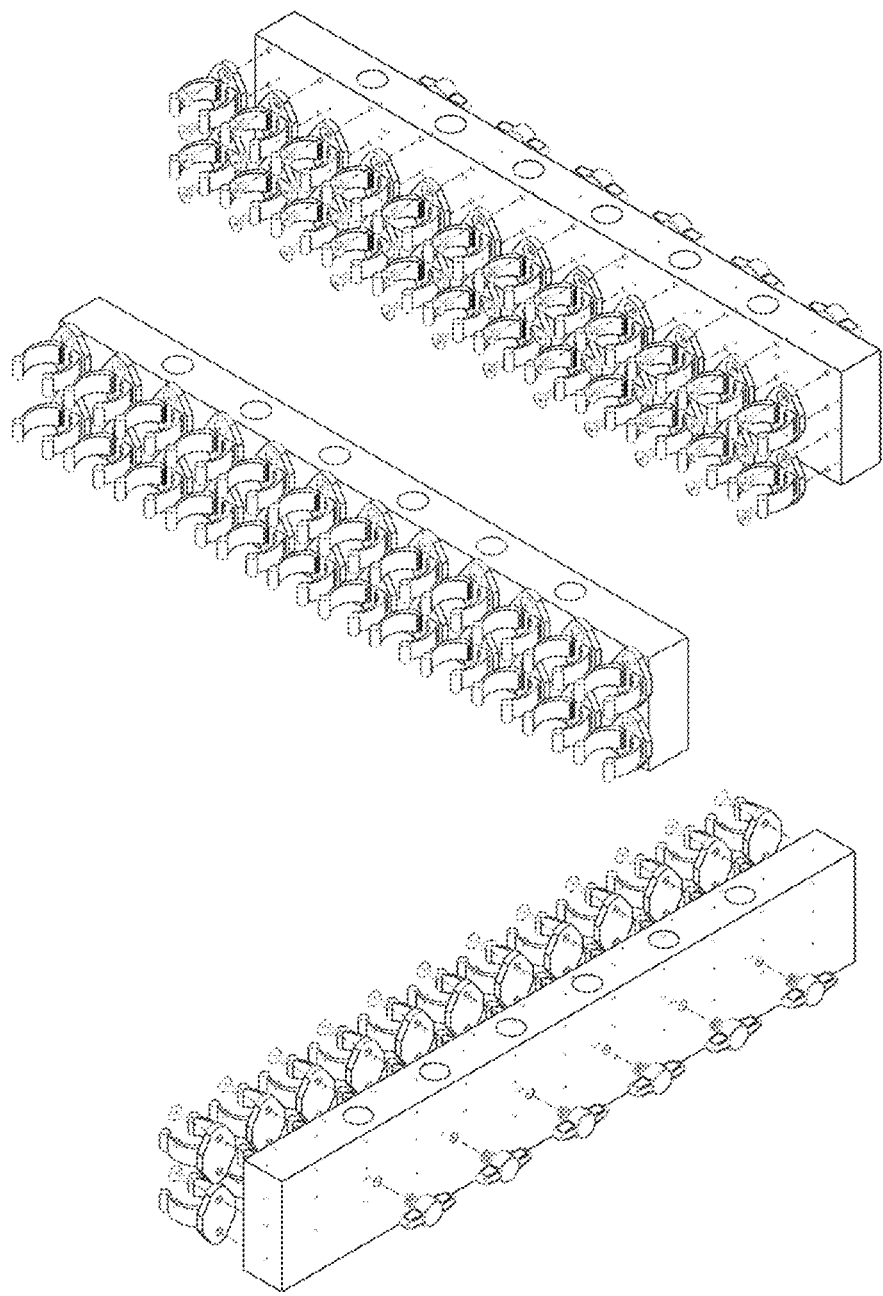
FIG. 52 shows non-exploded and exploded views of small reservoir holders, in accordance with an embodiment of the invention.

FIG. 52 shows non-exploded and exploded views of the small reservoir holder, according to alternative embodiments of the invention.

Figure 53A:
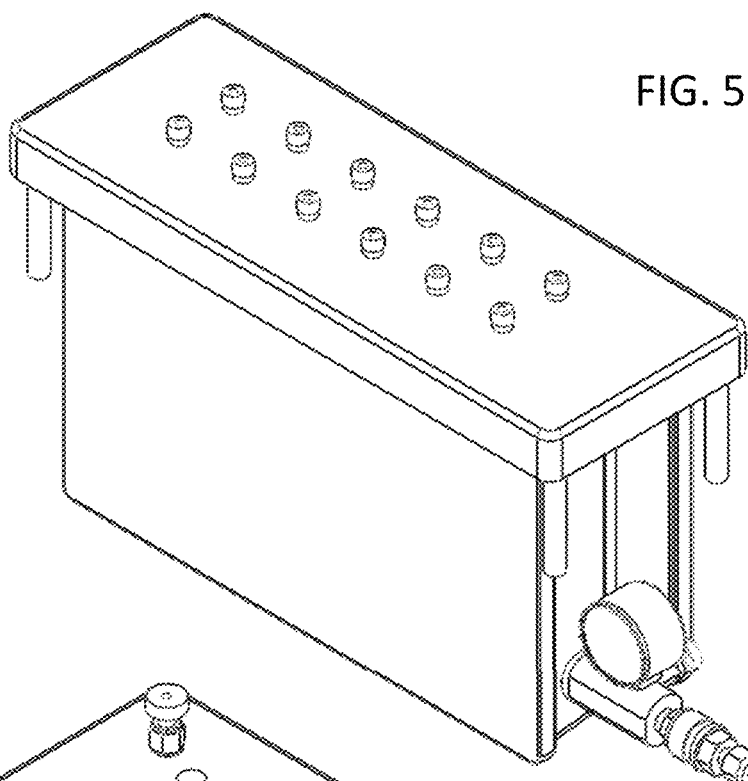
FIGS. 53A and 53B are perspective views of Stage 2 Manifolds, in accordance with alternative embodiments of the invention.
Figure 53B:
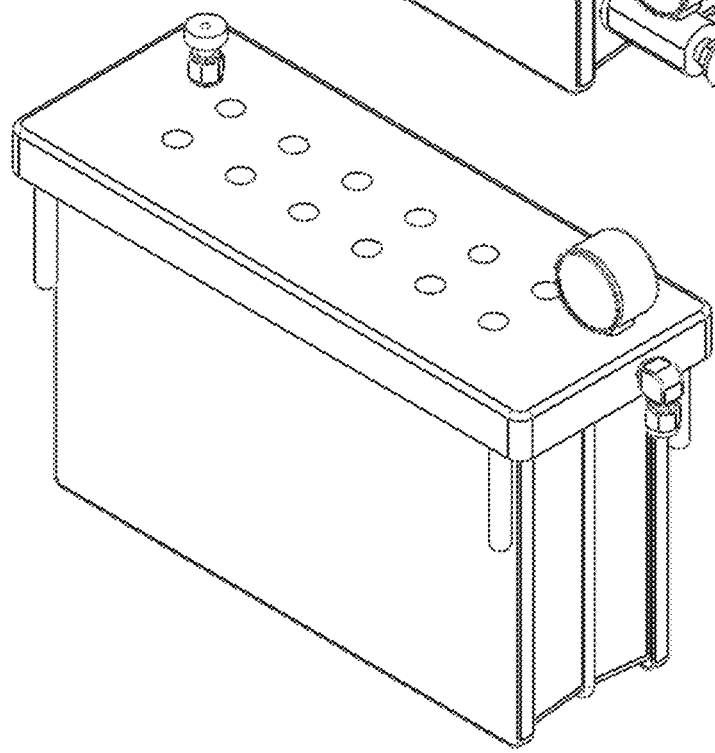

FIG. 53 shows a perspective view of the Stage 2 manifold according to an embodiment A of the invention compared to a perspective view of the Stage 2 manifold according to an alternative embodiment B of the invention. In embodiment A, a vacuum line adapter is positioned to a side or shorter length of the Stage 2 manifold and connects the Stage 2 manifold to a fitting for a 3-way valve. A vacuum gauge and vacuum relief valve are also connected to the vacuum line adapter. In embodiment B, a vacuum relief valve and a vacuum gauge are separately disposed on a lid of the Stage 2 manifold. The three-way valve fitting is disposed on the side or shorter length of the Stage 2 Manifold.

Figure 54A:
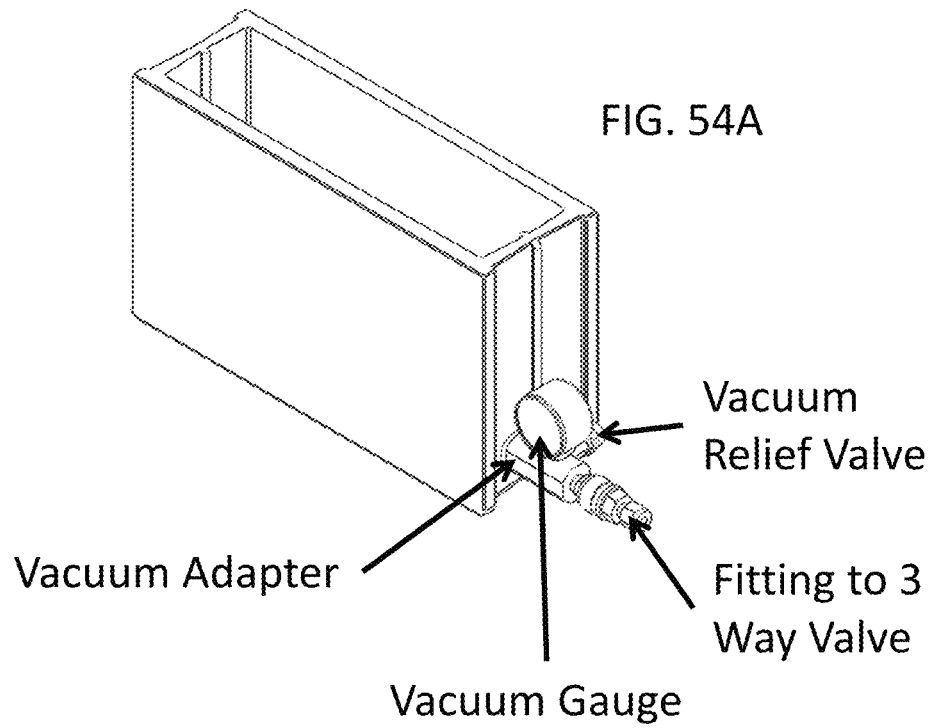
FIGS. 54A and 54B are perspective views of Stage 2 Manifold chambers, in accordance with alternative embodiments of the invention.
Figure 54B:
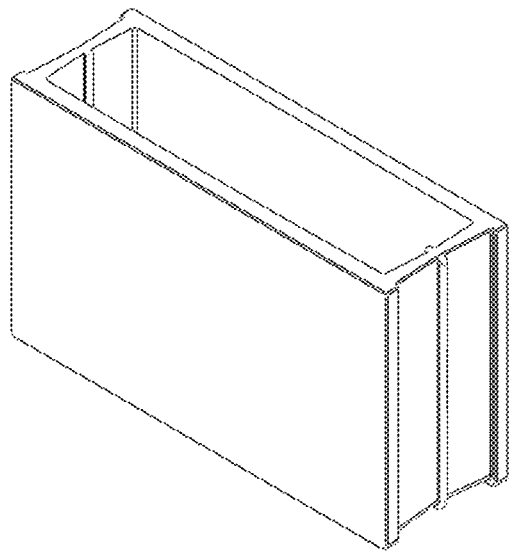

FIG. 54 shows a perspective view of the Stage 2 manifold, according to an embodiment A of the invention, compared to a perspective view of the Stage 2 manifold, according to an alternative embodiment B of the invention. In the embodiment A, the Stage 2 chamber has an opening for a vacuum adapter allowing fluid flow through the wall of the chamber for connection outside the chamber to a three-way valve fitting, a vacuum relief valve and a vacuum gauge. In the alternative embodiment B, the Stage 2 chamber does not have the opening for the vacuum adapter.

Figure 55A:
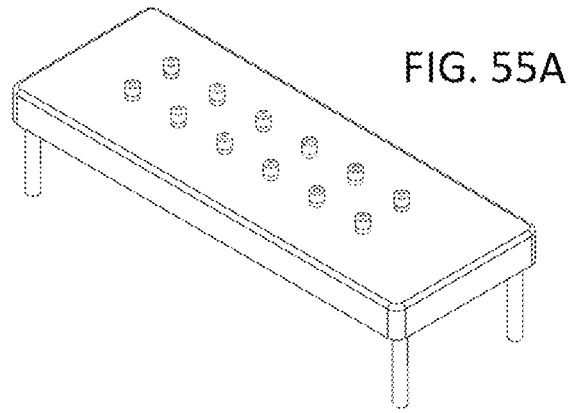
FIGS. 55A and 55B are perspective views of Stage 2 Manifold lids, in accordance with alternative embodiments of the invention.
Figure 55B:
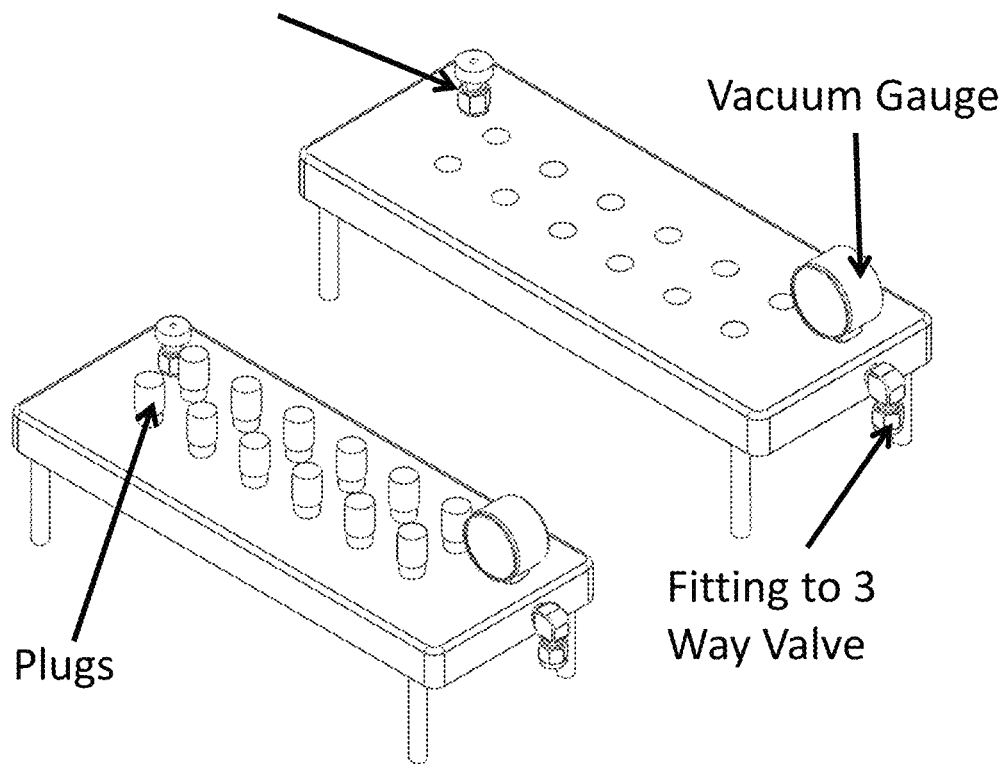

FIG. 55 shows the Stage 2 manifold lid according to an embodiment A of the invention compared to the Stage 2 manifold Lid according to an alternative embodiment B of the invention. In the embodiment A, the Stage 2 manifold Lid has one or more female luers for receiving the male luers of corresponding assay columns. In the alternative embodiment B, the Stage 2 manifold Lid has one or more holes or openings for receiving the assay columns. A vacuum relief valve, vacuum gauge and a three-way valve fitting are disposed on the Stage 2 manifold Lid thereby reducing and/or preventing any contamination or leakage from the Stage 2 manifold Chamber. The Stage 2 Manifold Lid also includes plugs for sealing the holes or openings in the lid when the respective holes or openings are column free.

Figure 56:
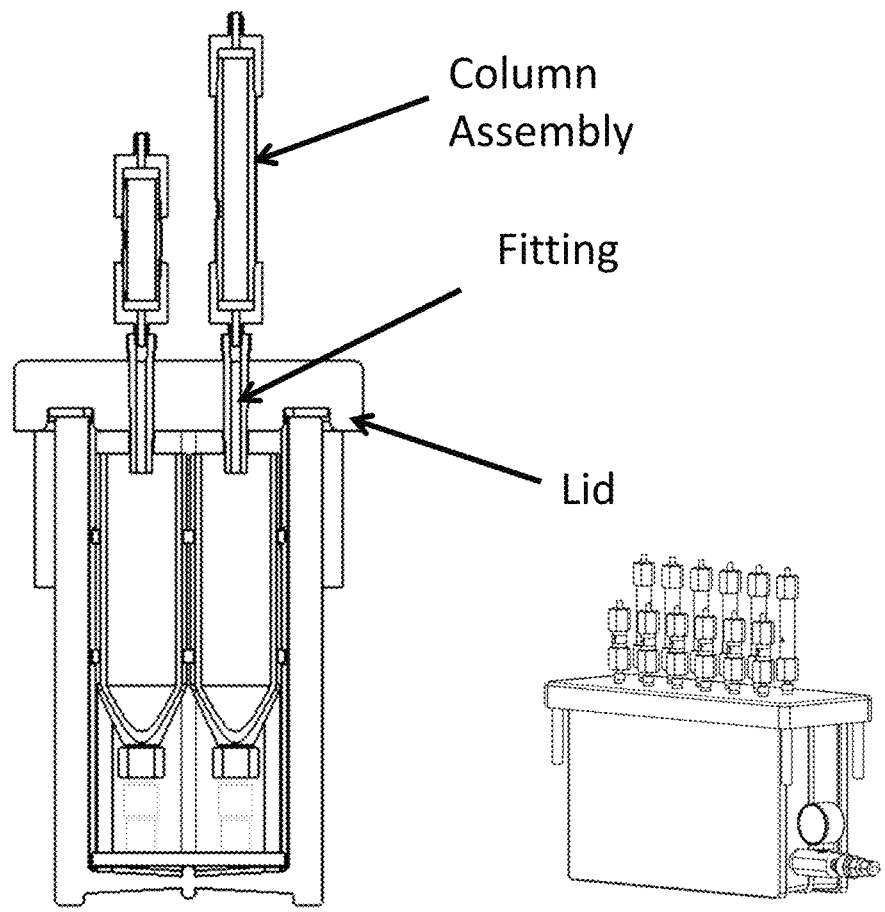
FIG. 56 includes views of Stage 2 Manifolds including fittings for column connection to Stage 2 Manifold lid, in accordance with an embodiment of the invention.
Figure 57:
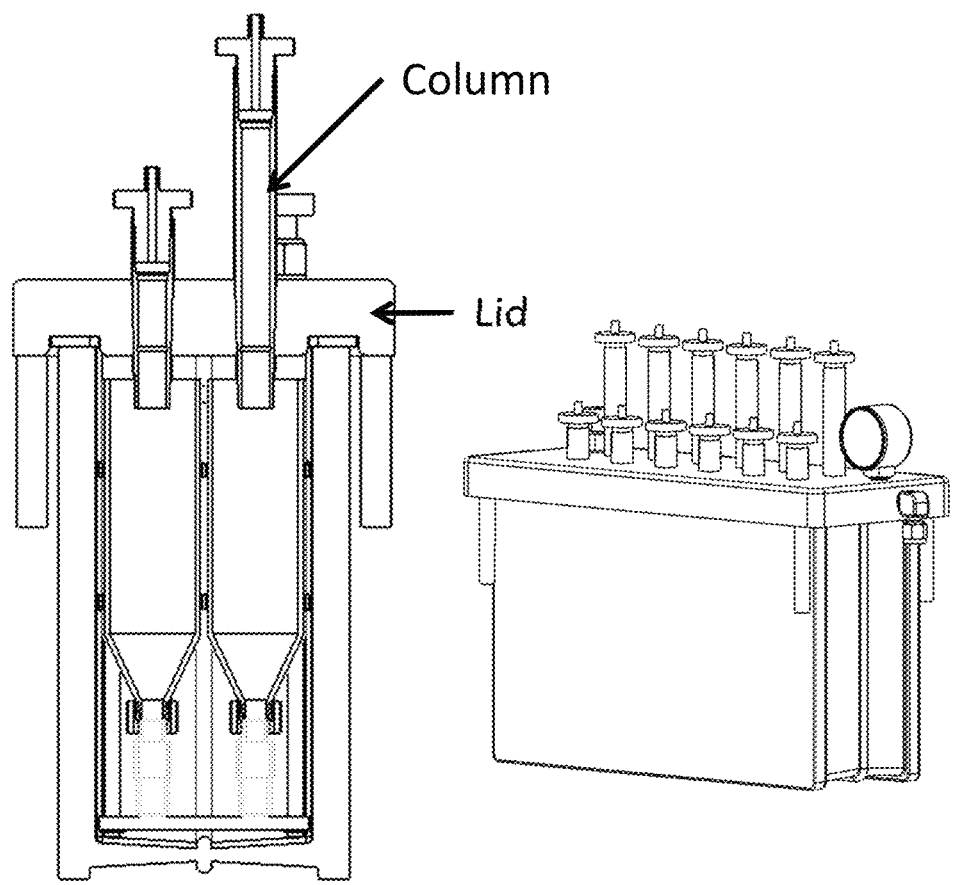
FIG. 57 includes views of Stage 2 Manifolds configured for direct column connection to a Stage 2 Manifold lid, in accordance with an embodiment of the invention.

FIG. 56 shows the Stage 2 manifold luers for connecting to the assay columns according to an embodiment A of the invention. In comparison, FIG. 57 shows the male luers of the columns inserted directly into the holes or openings of the Stage 2 manifold lid without the need of additional luers or fittings according to an alternative embodiment B of the invention.

FIG. 58 shows a three-way valve bracket being disposed on top surface of the rotational plate where the trunk or stem of the valve is disposed in the same plane as the rotational plate, according to an embodiment A of the invention. FIG. 58 also shows an alternative embodiment B of the invention where a three-way valve bracket is disposed on the top surface of the rotational plate but the bracket is configured such that the three-way valve is elevated to a select height above the rotational plate for easier access. The trunk or stem of three-way valve is disposed at a right angle relative to the rotational plate again and the lever is disposed in the same plane as the rotational plate, again for easier access for the user.

According to another aspect, the vacuum system and methods of the invention feature purification of and extraction of a substance from a fluid sample. In a preferred embodiment, the extraction includes SPE. In other preferred embodiments, the fluid samples include water, milk, blood and/or serum.

Figure 59:
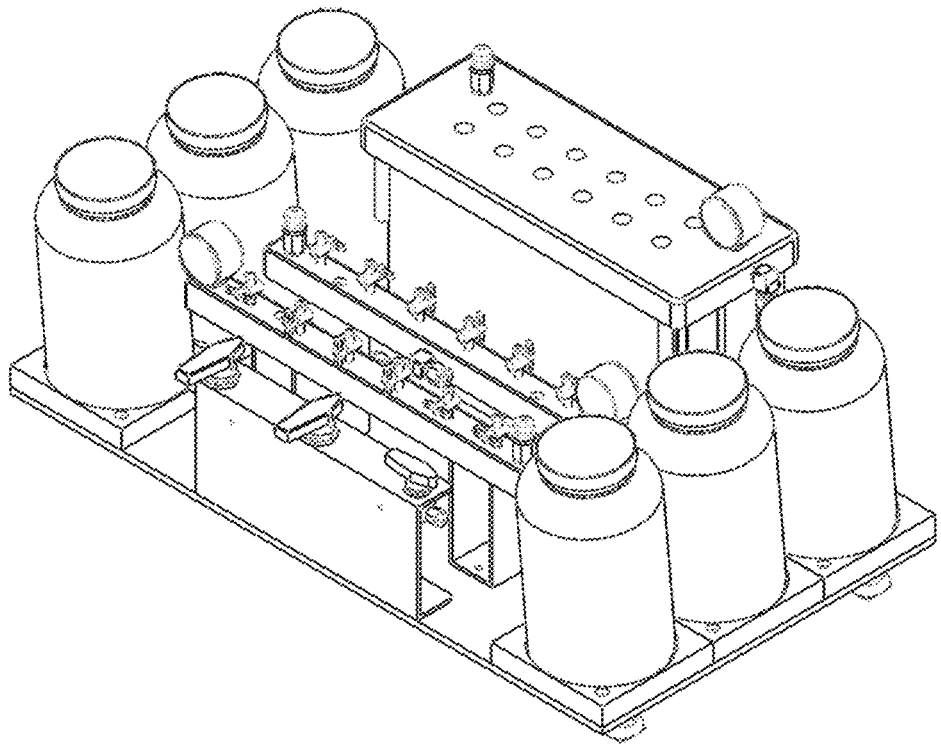
FIG. 59 is a schematic of a perspective view of a Solids Phase Extraction system, in accordance with an embodiment of the invention.

FIG. 59 shows a perspective view of a SPE fluid sample processing system according to one embodiment of the invention.

Figure 60:
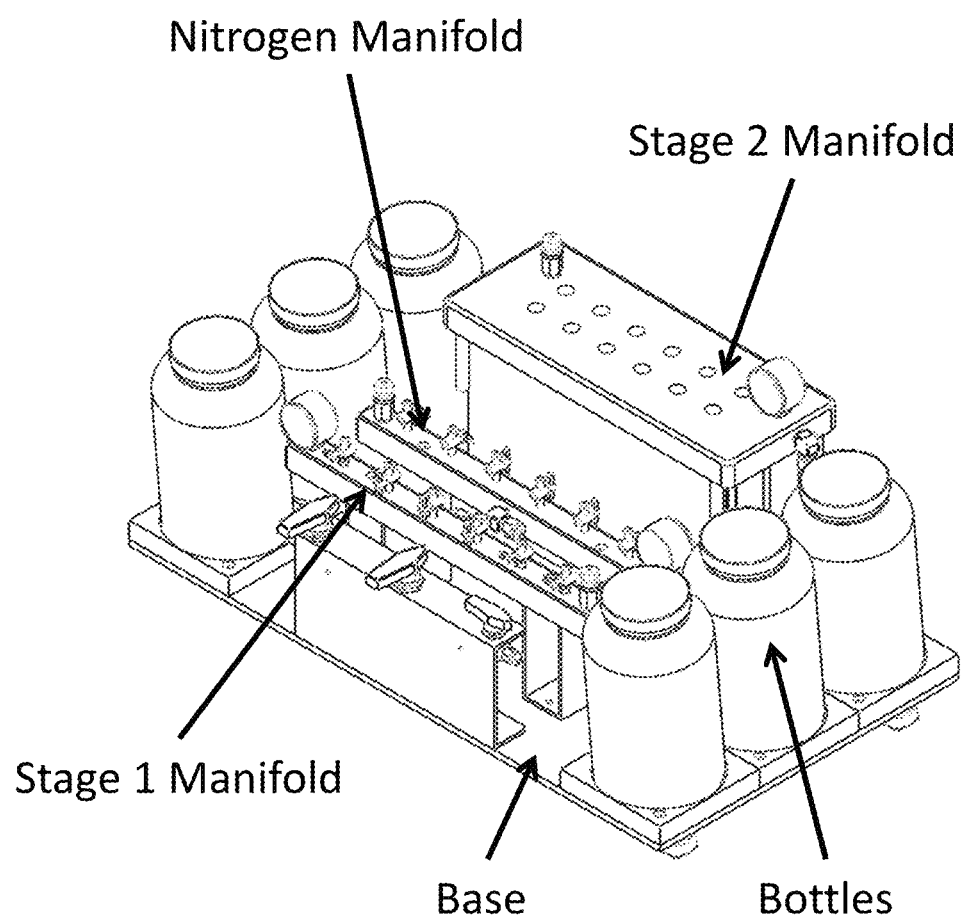
FIG. 60 is a schematic of a perspective view of a Solids Phase Extraction system, in accordance with an embodiment of the invention.

FIG. 60 shows a perspective view a SPE fluid sample processing system including a Stage 1 Manifold, a drying gas manifold, where the drying gas is nitrogen, for a non-limiting example, and a Stage 2 manifold.

Figure 61:
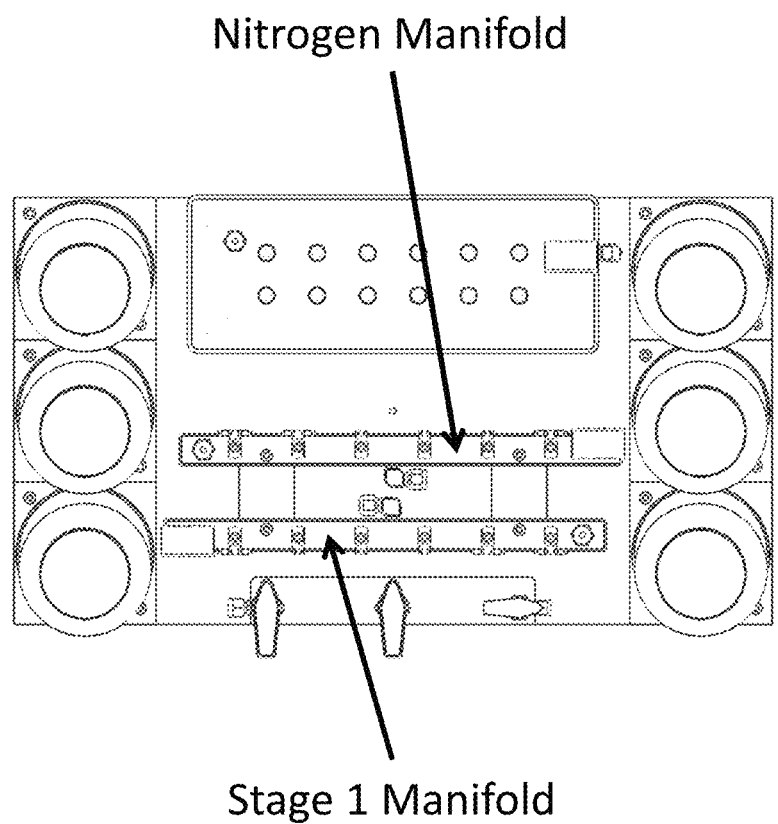
FIG. 61 is a schematic of a top view of a Solids Phase Extraction system, in accordance with an embodiment of the invention.

FIG. 61 shows a top view of the SPE fluid processing system including a Stage 1 manifold, a drying Gas, such as, for a non-limiting example, a Nitrogen Manifold, and a Stage 2 manifold.

Figure 62:
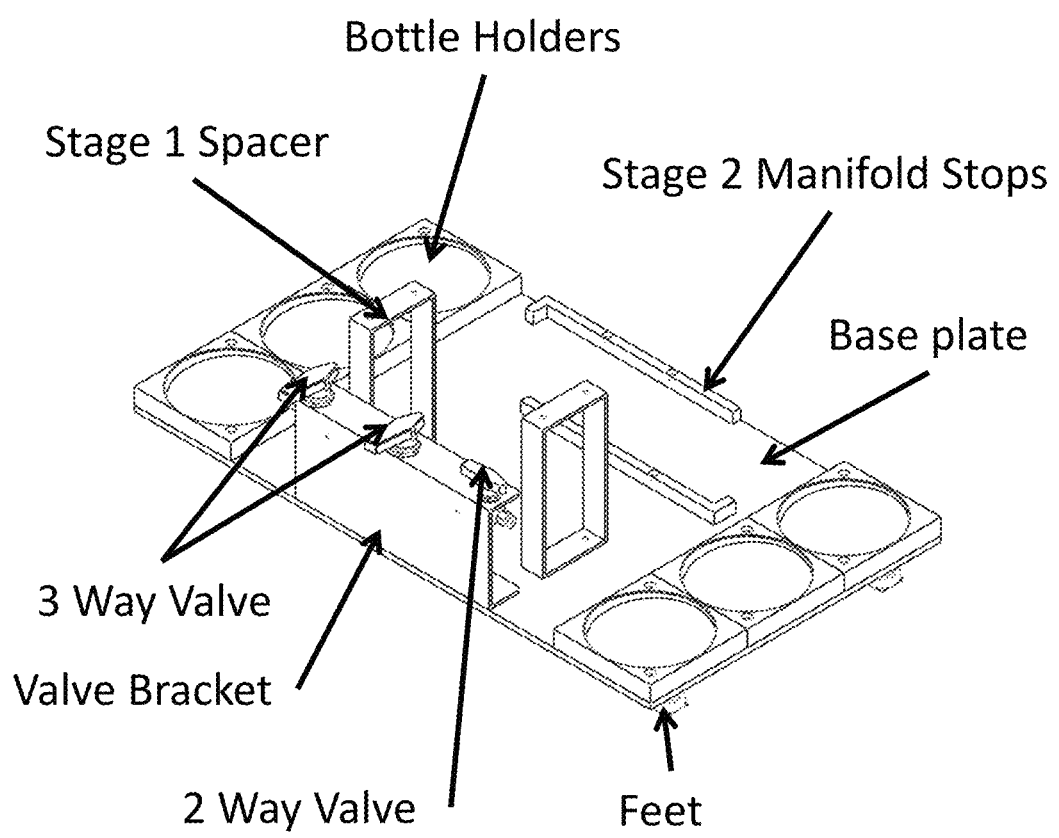
FIG. 62 is a schematic of a base plate of a Solids Phase Extraction system, in accordance with an embodiment of the invention.

FIG. 62 shows a perspective view of the SPE fluid processing system without the Manifolds but including baseplate with the Stage 1 Manifold Spacer, the Stage 2 Manifold Stops, the valve bracket including two three-way valves and a two-way valve, bottle holders and feet or positioning devices for the baseplate.

FIG. 63 shows the Stage 1 Manifold and Drying Gas, such as, for a non-limiting example, a Nitrogen Manifold of the SPE fluid processing system of the invention. Each Manifold includes a vacuum or pressure gauge, a vacuum or pressure relief valve or regulator, one or more fittings each with a stop cock for controlled fluidic connection to a corresponding assay column, and a fitting for a valve connection.

Figure 64:
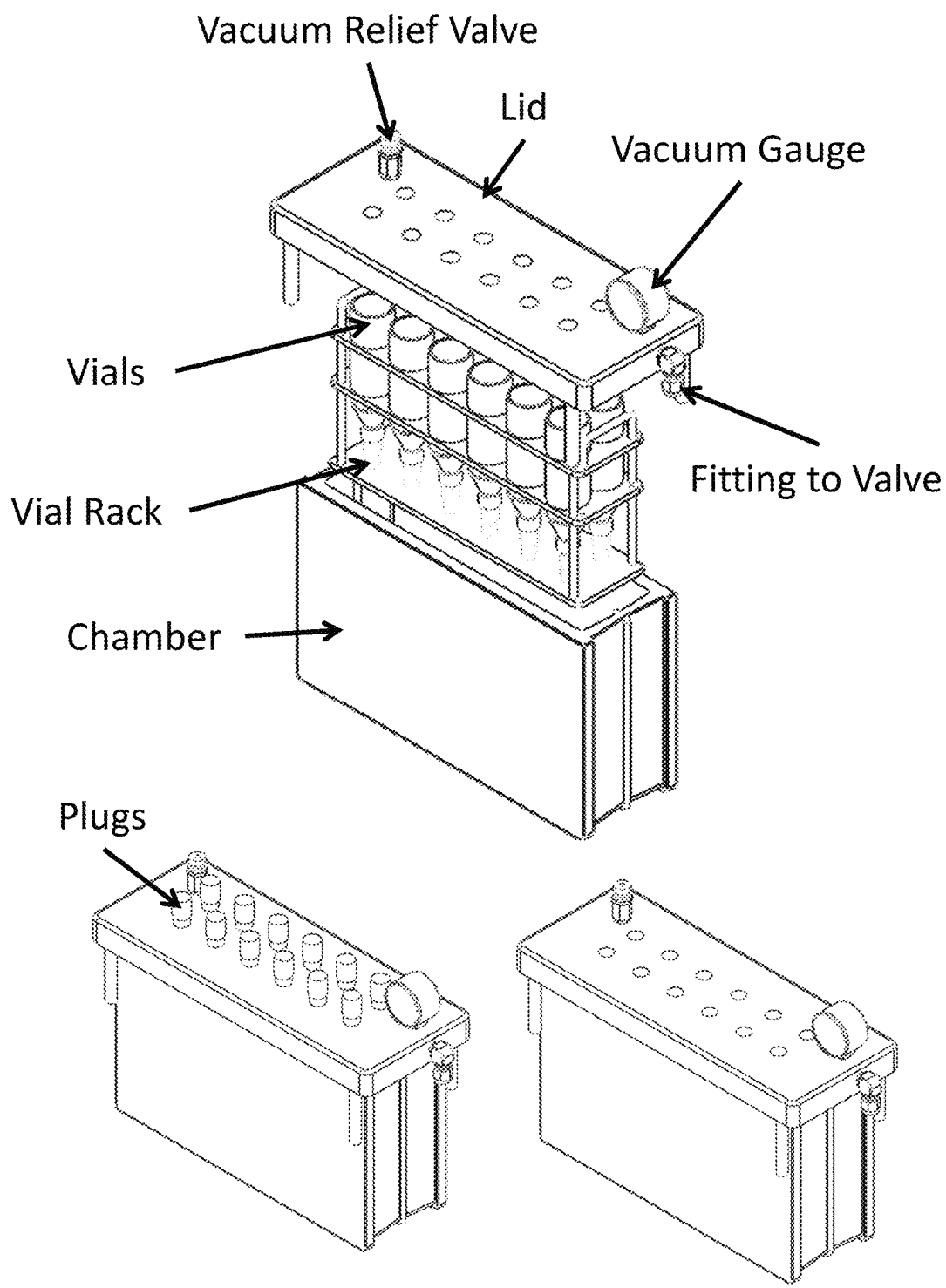
FIG. 64 includes schematics of Stage 2 Manifolds for a Solids Phase Extraction system, in accordance with an embodiment of the invention.

FIG. 64 shows the Stage 2 manifold. The Stage 2 manifold of the SPE fluid processing system is similar to the Stage 2 manifold described above for the liquid extraction and purification system of the invention. In one exemplary embodiment, the Stage 2 manifold lid can include the vacuum relief valve separately disposed on the lid of the Stage 2 manifold chamber, and a valve fitting is disposed on the side or shorter length of the chamber. A vial rack holding one or more vials can be disposed within the chamber.

Figure 65:
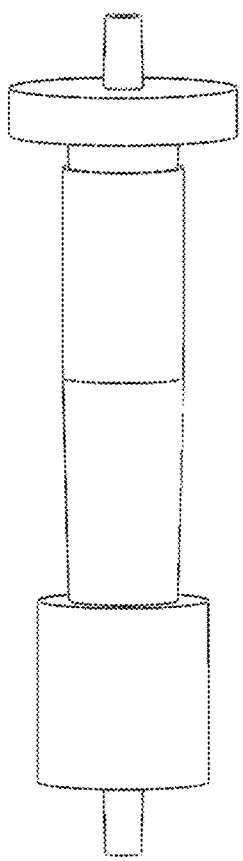
FIG. 65 is a schematic of an assay column for a Solids Phase Extraction system, in accordance with an embodiment of the invention.

FIG. 65 shows a non-limiting example of an assay column having fittings at opposing ends for connecting respectively to the Stage 1 Manifold and to a bottle in the SPE fluid processing system.

Figure 66:
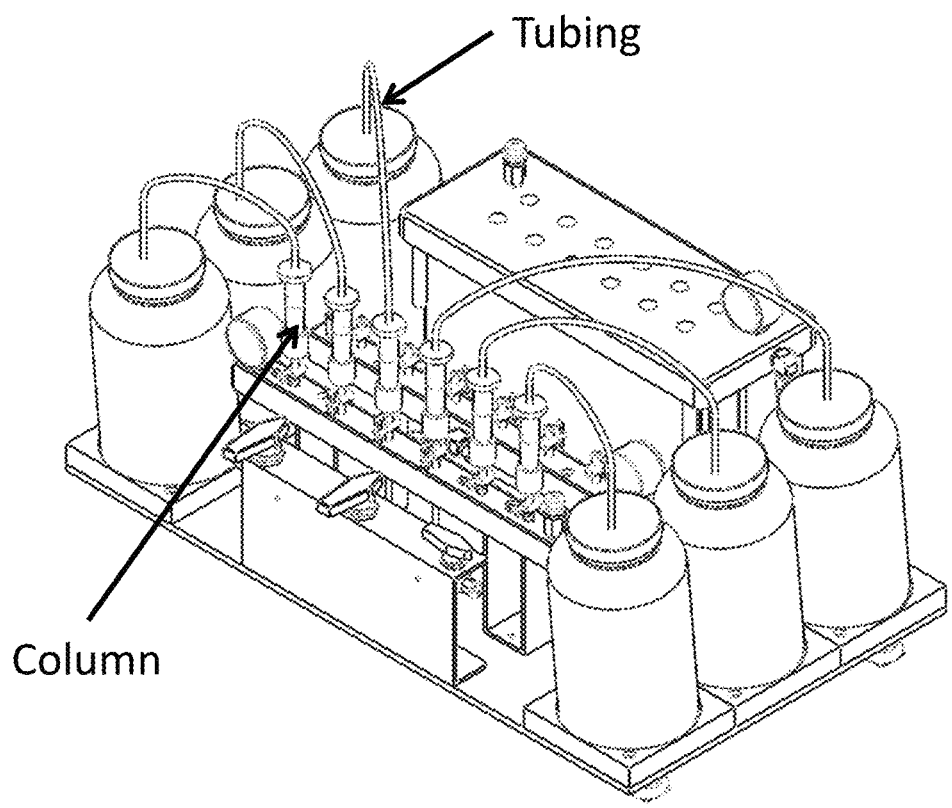
FIG. 66 is a schematic of a Solids Phase Extraction system during Stage 1 column installation and connection, in accordance with an embodiment of the invention.

FIG. 66 shows the Stage 1 configuration of the SPE fluid processing system of the invention. One or more assay columns are fluidically and reversibly connected to a Stage 1 manifold. The Stage 1 manifold is plumbed sequentially to a stage 1 and 2 three-way valve, a three-way waste valve, a waste receptacle including an organic waste receptacle and an aqueous waster receptacle, and a vacuum pump. During a Stage 1 column conditioning step, the at least one assay column is conditioned during a preliminary step. A solvent such as, an organic solvent, is inserted into the at least one assay column and is drawn through the column with vacuum to condition and/or remove any contaminants which may be present in the column. The organic waste is diverted using the three-way waste valve and collected in the organic waste receptacle. During a stage 1 sample loading step, one or more sample fluid containers such as bottles containing a sample fluid are fluidically and reversibly connected via sample fluid container tubing or other connecting device to the one or more corresponding assay columns which are fluidically and reversibly connected to the Stage 1 manifold. During Stage 1 sample loading, the vacuum is applied to draw sample fluid into the one or more corresponding assay columns and the aqueous waste which exits the column is collected in the waste receptacle include the aqueous waster receptacle. The vacuum is then turned off, and the sample container tubing is disconnected.

Figure 67:
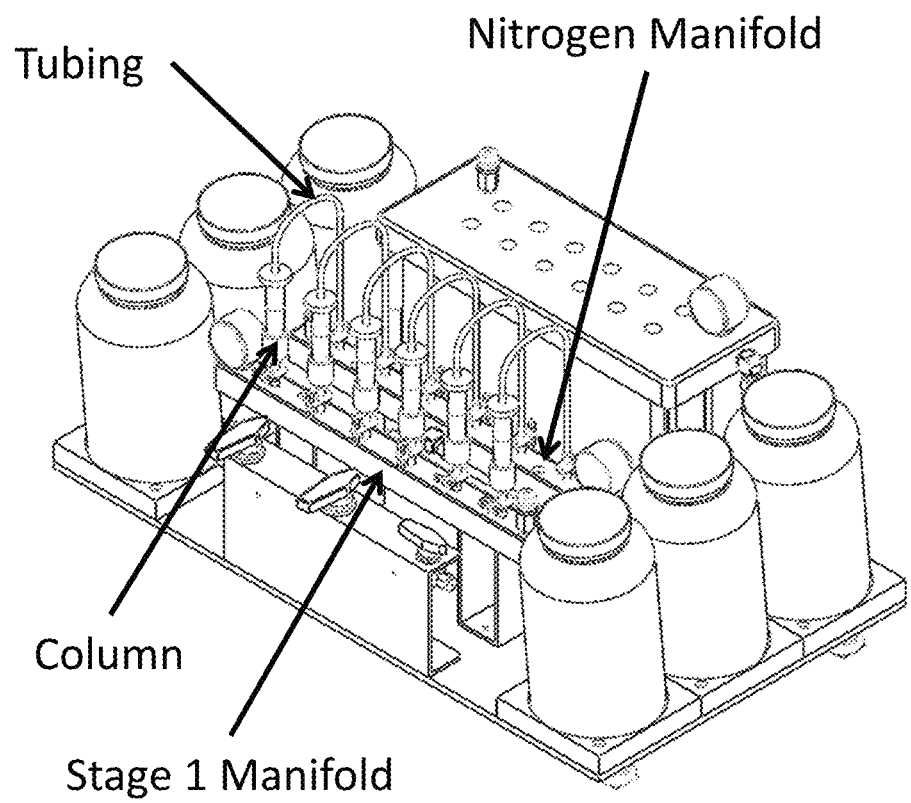
FIG. 67 is a schematic of a Solids Phase Extraction system during Stage 1 column drying, in accordance with an embodiment of the invention.

FIG. 67 shows the next step of Stage 1 drying. Drying can be accomplished with ambient air according to a non-limiting exemplary embodiment. Alternatively, drying tubing or other connecting device can be used to fluidically and reversibly connect the one or more assay columns, or in alternative embodiments to the drying gas manifold. In a non-limiting exemplary embodiment, the drying gas is nitrogen. Vacuum is again turned on to draw the drying gas through the one or more assay columns for drying. After drying, the drying gas and the vacuum can be shut off and the drying tubing is disconnected from the one or more assay columns.

Figure 68:
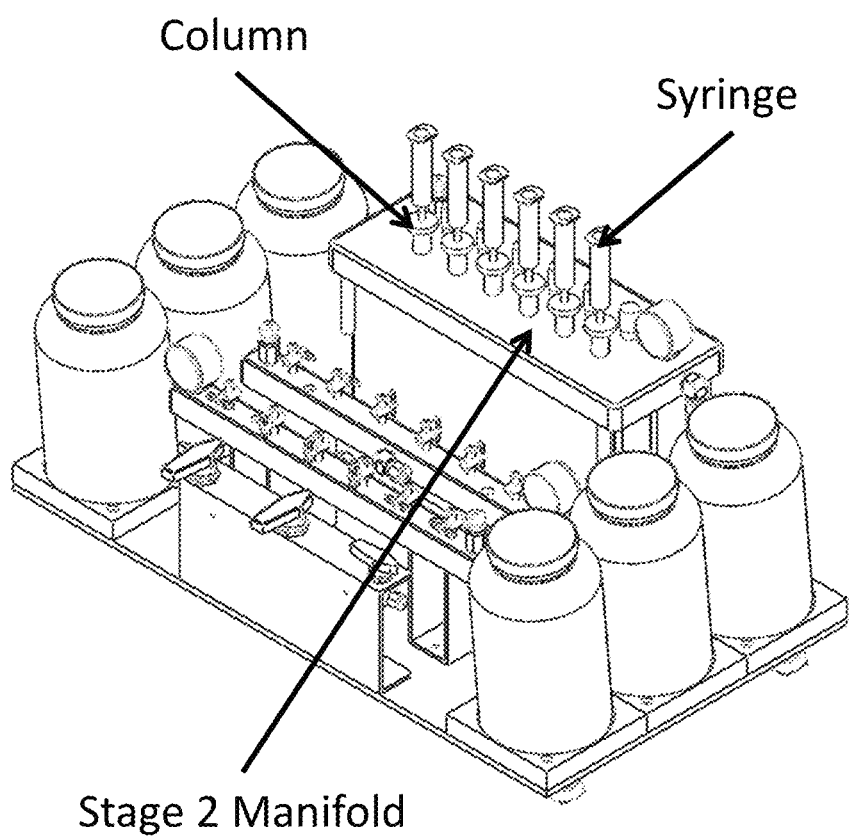
FIG. 68 is a schematic of a Solids Phase Extraction system during Stage 2 sample elution, in accordance with an embodiment of the invention.

FIG. 68 shows the next step of Stage 2 sample elution of the SPE fluid processing system. A first end of each of the one or more assay columns is disconnected from the Stage 1 manifold and the same first end is fluidically and reversibly connected to the Stage 2 manifold. One or more solvent reservoirs are fluidically and reversibly connected to corresponding one or assay columns. Vacuum is applied and solvent is passed through the one or more assay columns for elution of the analyte substance and collected in corresponding one or more elution fluid containers, such as, for non-limiting examples, one or more elution vials included in the Stage 2 Chamber.

Figure 69A:
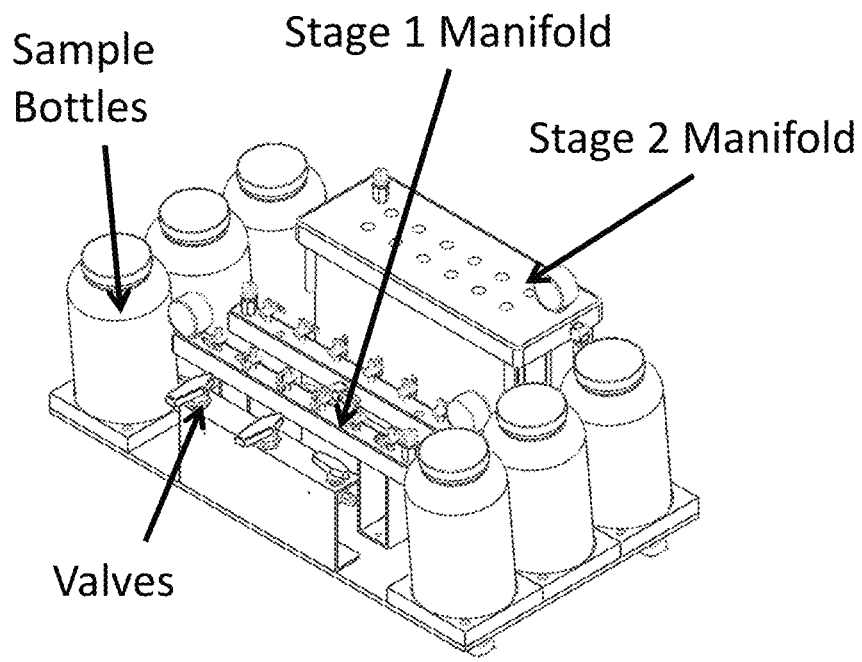
FIGS. 69A and 69B are respective schematics of Solids Phase Extraction systems, in accordance with alternative embodiments of the invention.
Figure 69B:
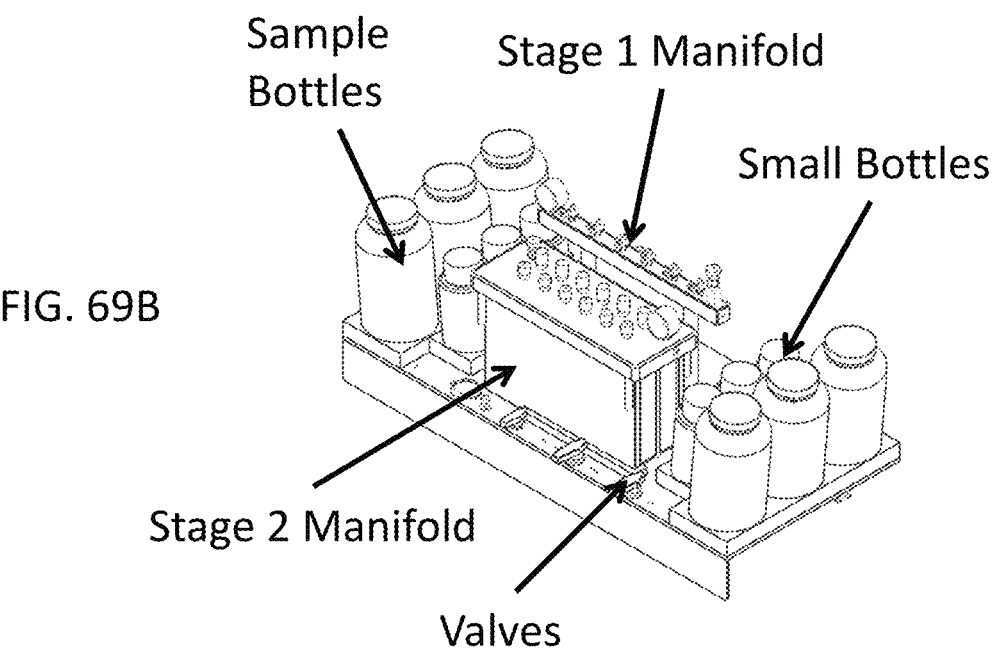

FIG. 69 shows an alternative embodiment B of the SPE fluid processing system in comparison with the embodiment A described above in FIG. 60. In the alternative embodiment B, one or more additional bottles or other fluid containers are positioned on the base plate next to or otherwise proximate to corresponding sample fluid containers. These additional fluid containers can be differently or similarly sized as compared to the sample fluid containers. The additional fluid containers can be used to provide washing or flushing fluids which can be then used to wash down and/or flush out any contaminants and/or remaining sample fluid contained in the sample fluid containers. FIG. 69 shows these additional fluid containers as, for a non-limiting example, smaller bottles as compared to the sample bottles. Embodiment B includes valves being disposed on or the base plate and proximate to the Stage 2 Manifold as compared to embodiment A where valves are disposed on a plate raised above level of the base plate and proximate to the Stage 1 Manifold. These valves are described further below. During operation washing tubing or another connecting device are used to fluidically and reversibly connect the one or more assay columns or the one or more sample fluid containers to the washing fluid containers. A vacuum can be applied for drawing the washing fluid from the washing fluid containers into the sample fluid containers or through the one or more assay columns for washing or flushing the respective sample fluid containers or the assay columns. In alternative embodiments, the drying gas can be used to push the washing fluid from the washing fluid containers to the sample fluid containers or the assay columns.

Figure 70A:
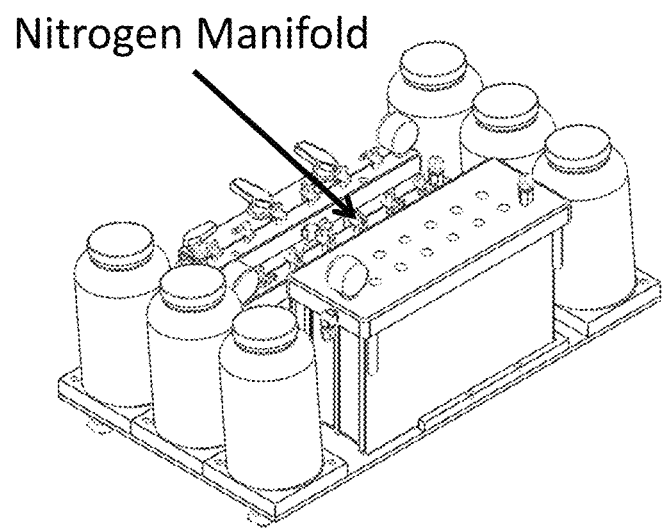
FIGS. 70A and 70B are respective schematics of Drying Gas or Nitrogen Manifolds for Solids Phase Extraction systems, in accordance with alternative embodiments of the invention.
Figure 70B:
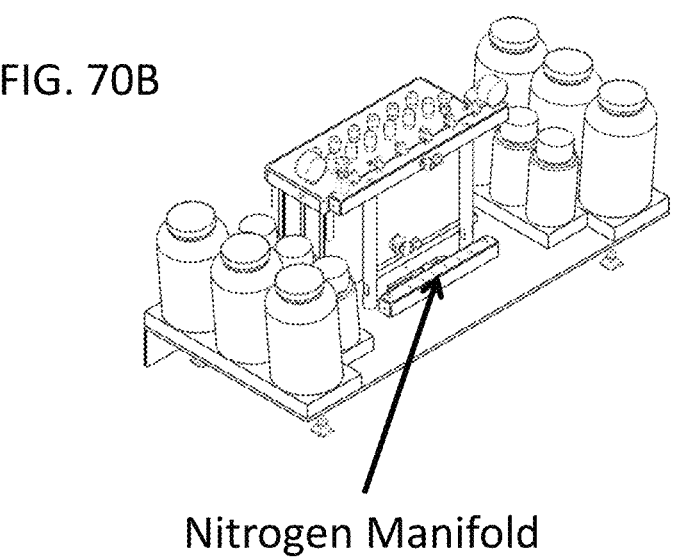

FIG. 70 further shows an alternative embodiment B of the SPE fluid processing system in comparison with the embodiment A described above in FIG. 60. FIG. 70 shows the embodiment B Nitrogen or other Drying Gas Manifold being disposed on or proximate to the base plate in comparison with embodiment A which shows the Drying Gas such as Nitrogen Manifold being disposed on a plate and raised above the level of the base plate.

Figure 71A:
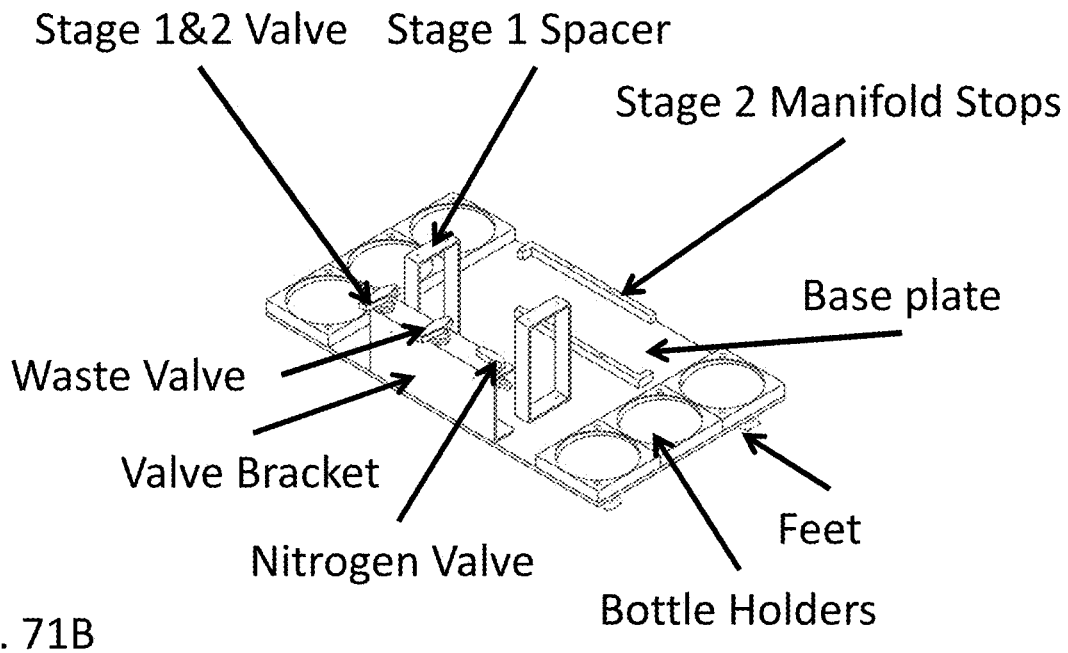
FIGS. 71A and 71B are respective schematics of base plates for Solids Phase Extraction systems, in accordance with alternative embodiments of the invention.
Figure 71B:
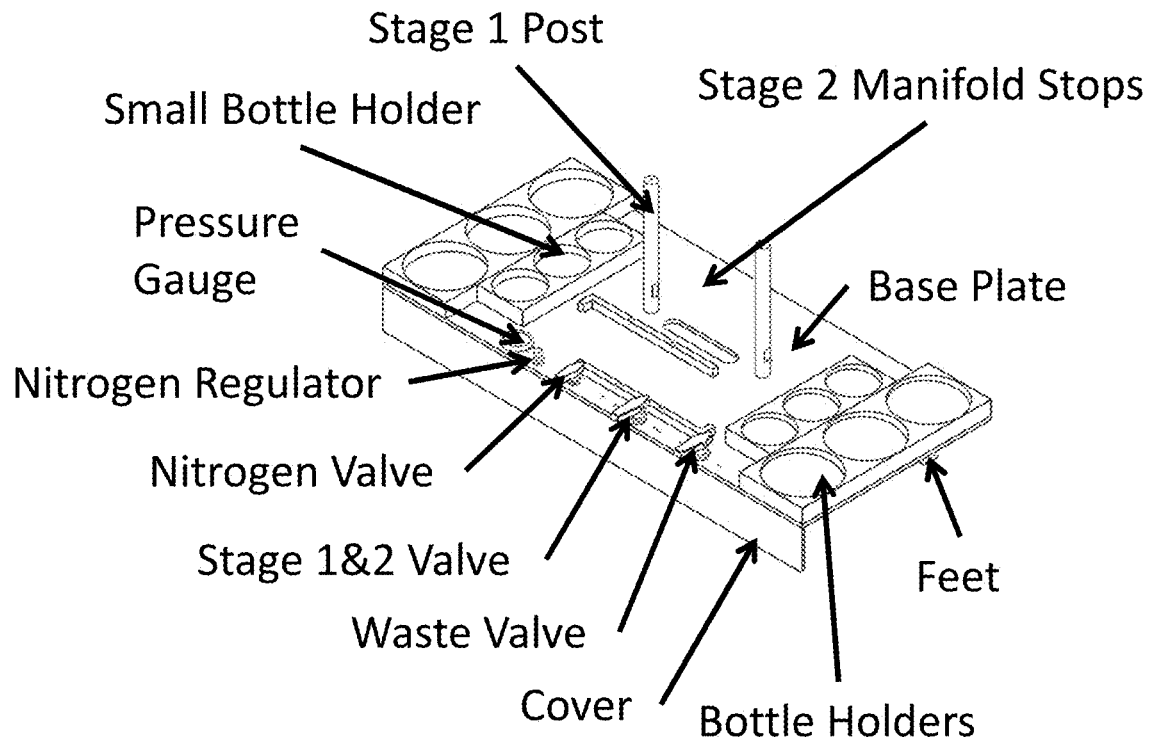

FIG. 71 shows the base plate of an alternative embodiment B of the SPE fluid processing system in comparison with the base plate of embodiment A described above in FIG. 62. The embodiment B base plate includes bottle holders for both sample fluid containers and washing or flushing fluid containers. A pressure gauge connecting device and a nitrogen or other drying gas regulator connecting device are disposed on the base plate of embodiment B. Valves including a drying gas or Nitrogen valve, a Stage 1&2 valve, and a waste valve, are disposed at an edge of the base plate and proximate to a first Stage 2 Manifold stop. A second Stage 2 Manifold stop is positioned towards a center of the base pate. The base plate has a cover for elevating the entire base plate from the surface upon which the base plate is positioned. The base plate also includes positioning feet. The base plate includes Stage 1 posts for positioning the Stage 1 Manifold. In contrast, embodiment A includes holders only for the sample bottles. Embodiment A includes similar valves disposed on a bracket and raised above the level of the base plate, as discussed above. The valve bracket is positioned proximate to Stage 1 Manifold Spacers. Embodiment A includes Stage 2 Manifold Stops positioned centrally and at the edge of the base plate. Embodiment A includes positioning feet for positioning the SPE fluid processing system based plate on a surface.

Figure 72A:
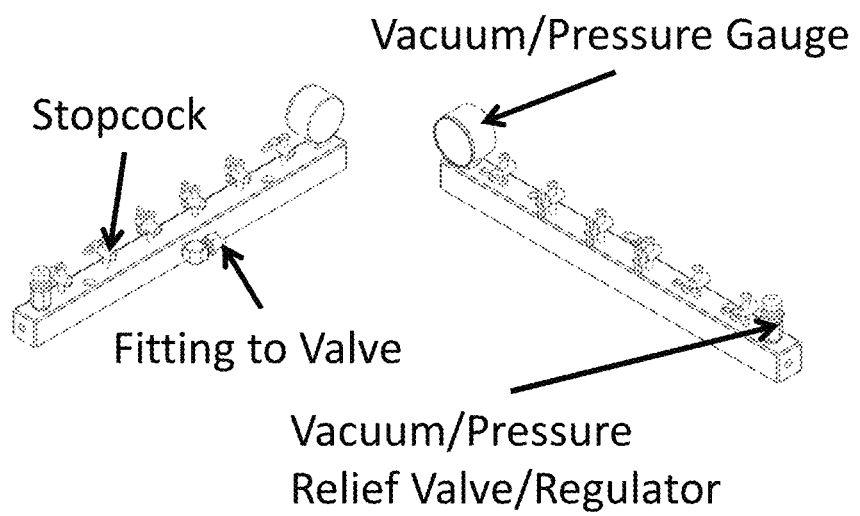
FIGS. 72A and 72B are respective schematics of Stage 1 or Drying Gas or Nitrogen Manifolds for Solids Phase Extraction systems, in accordance with alternative embodiments of the invention.
Figure 72B:
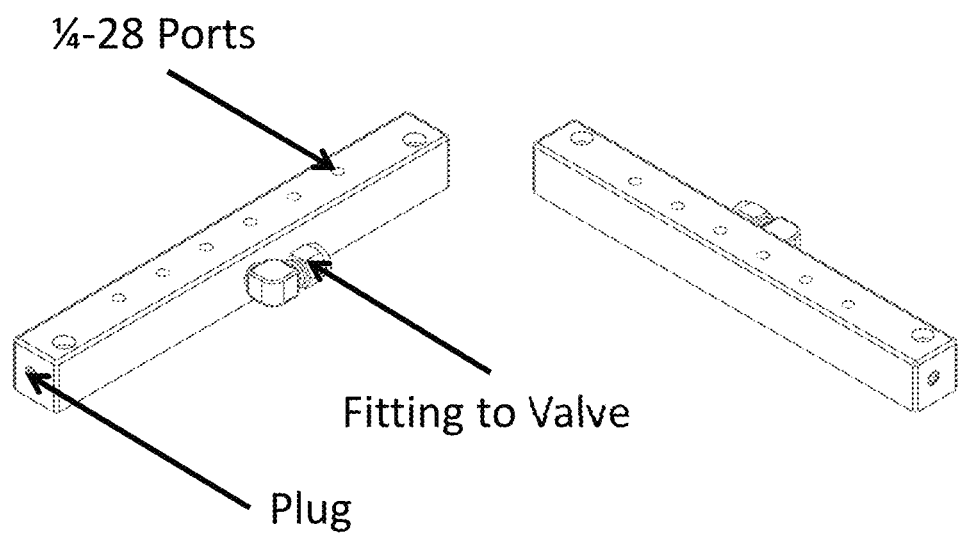

FIG. 72 shows the Drying Gas or Nitrogen Manifold of an alternative embodiment B in comparison with the Drying Gas or Nitrogen Manifold of embodiment A as described above in the context of FIG. 63. Embodiment B includes ports such as, for a non-limiting example, ¼-28 ports in lieu of the stop cocks shown in embodiment A. In contrast to embodiment A, the drying gas manifold of embodiment B does not include the gauge or regulator. The gauge or regulator can be disposed instead on the drying gas or nitrogen manifold lid, thereby minimizing and leaks related to such components. The drying gas manifold of embodiment A includes at least one hole covering device such as a plug on at least one end of the manifold. The drying gas manifold also includes a fitting for a Stage 1& 2 three-way valve.

Figure 73:
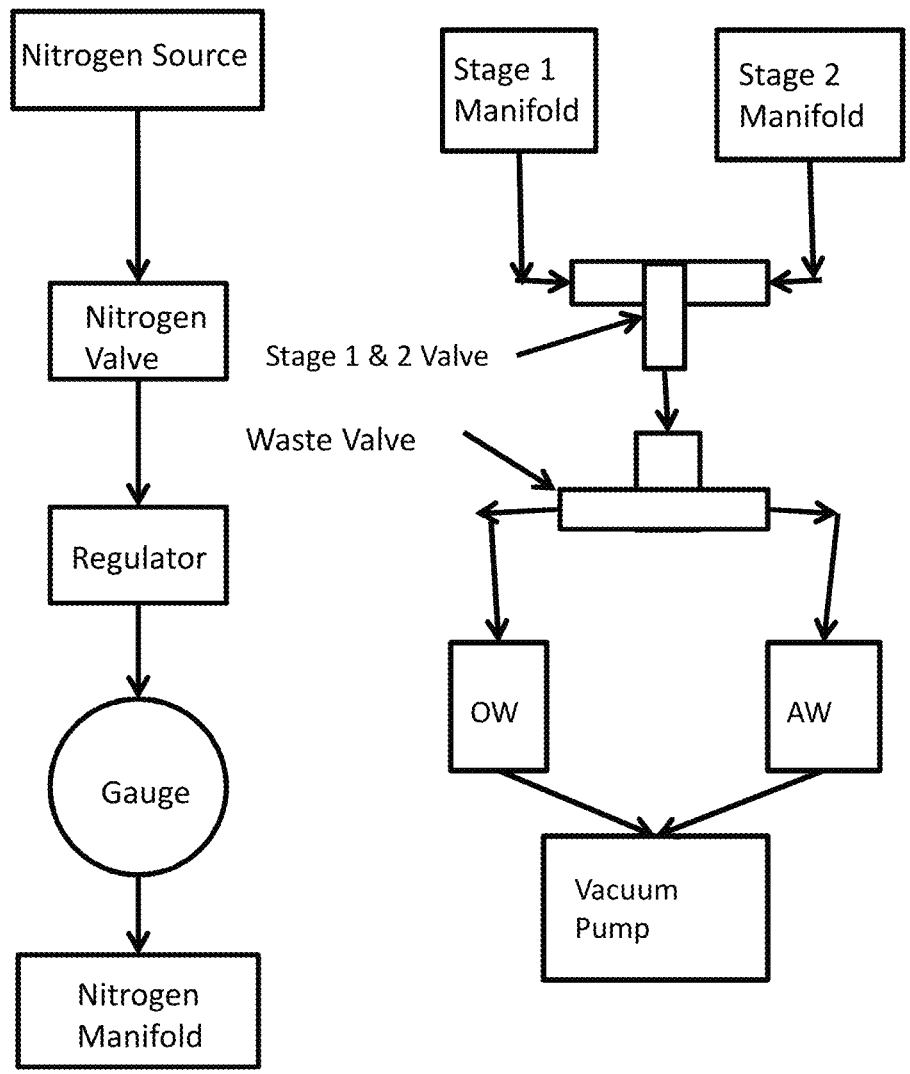
FIG. 73 is a schematic showing plumbing from the Drying Gas or Nitrogen source to the respective manifold, and from the Stage 1 and Stage 2 Manifolds for a Solids Phase Extraction systems, in accordance an embodiment of the invention.

FIG. 73 provides a schematic plumbing diagram for a SPE fluid processing system of the invention according to one embodiment. A drying gas, such as, for a non-limiting example, nitrogen, is sequentially connected in line with a drying gas or nitrogen valve, a drying gas or nitrogen regulator, a drying gas or nitrogen gauge, and the drying gas or nitrogen manifold. The Stage 1 Manifold and the Stage 2 Manifold are each connected to a three-way valve, also known as a Stage 1& 2 valve, which in turn is sequentially connected in line to a waste valve. The waste valve is a three-way valve for alternately directing organic waste to an organic waste receiving receptacle and for directing aqueous waste to an aqueous waste receiving receptacle. Each waste receptacle is connected in line to the vacuum pump.

FIGS. 74-85 show further embodiments of for the systems and methods discussed above in the context of FIGS. 1-58.

Figure 74A:
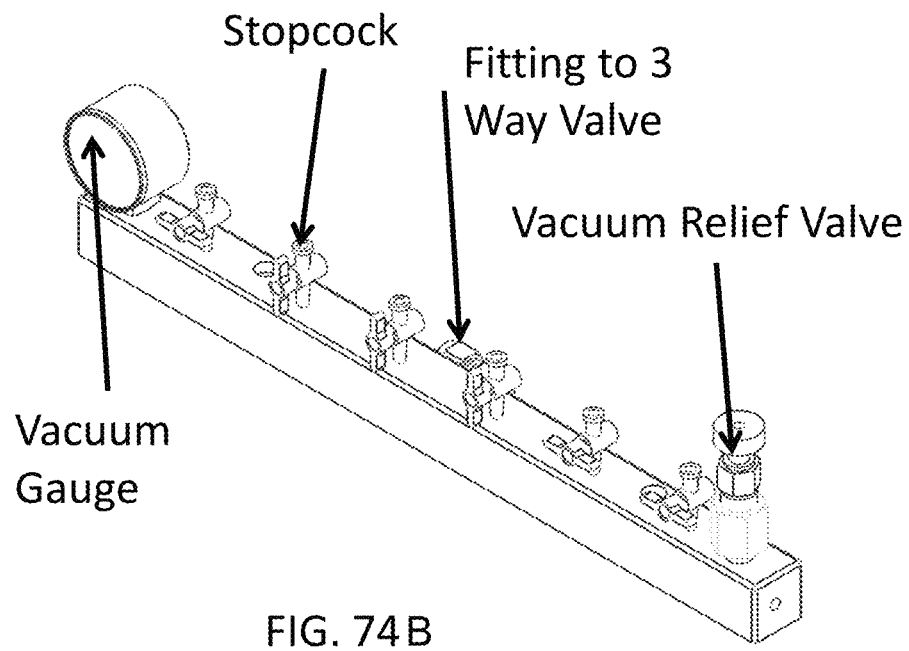
FIGS. 74A and 74B are schematics of Stage 1 Manifolds, in accordance with alternative embodiments of the invention.
Figure 74B:
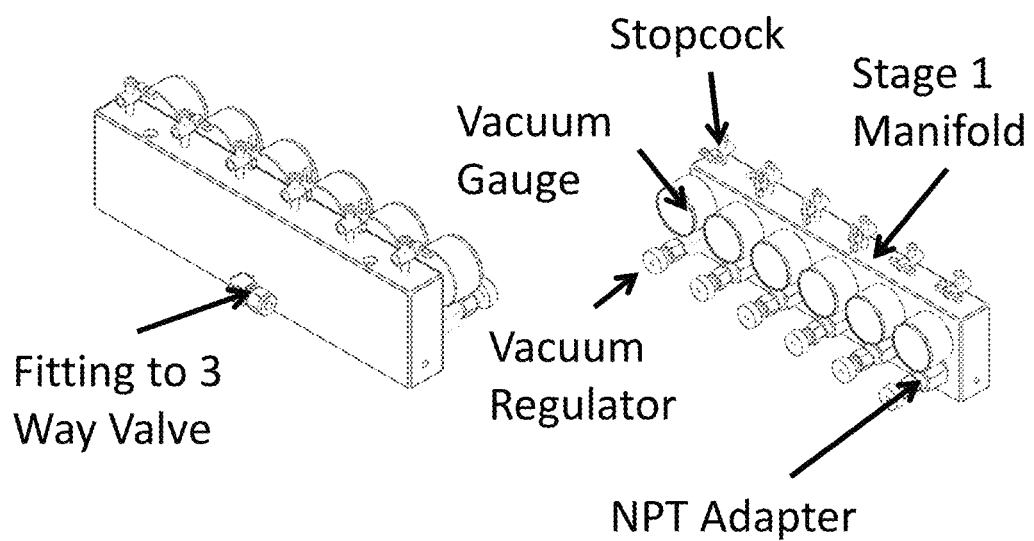

FIG. 74A shows Stage 1 Manifold control in comparison with a Stage 1 Manifold control according to an embodiment A previously shown in FIG. 46. The Stage 1 Manifold according to FIG. 74A includes a single vacuum relief valve to allow the user or operator to adjust the vacuum during the operation of Stage 1 for maintaining optimal fluid flow. In FIG. 74B, a vacuum gauge and vacuum regulator are provided for each assay column. A standardized fitting such as, for a non-limiting example, a national pipe taper or NPT adapter can be used to fluidically connect each vacuum regulator to the Stage 1 Manifold.

Figure 75A:
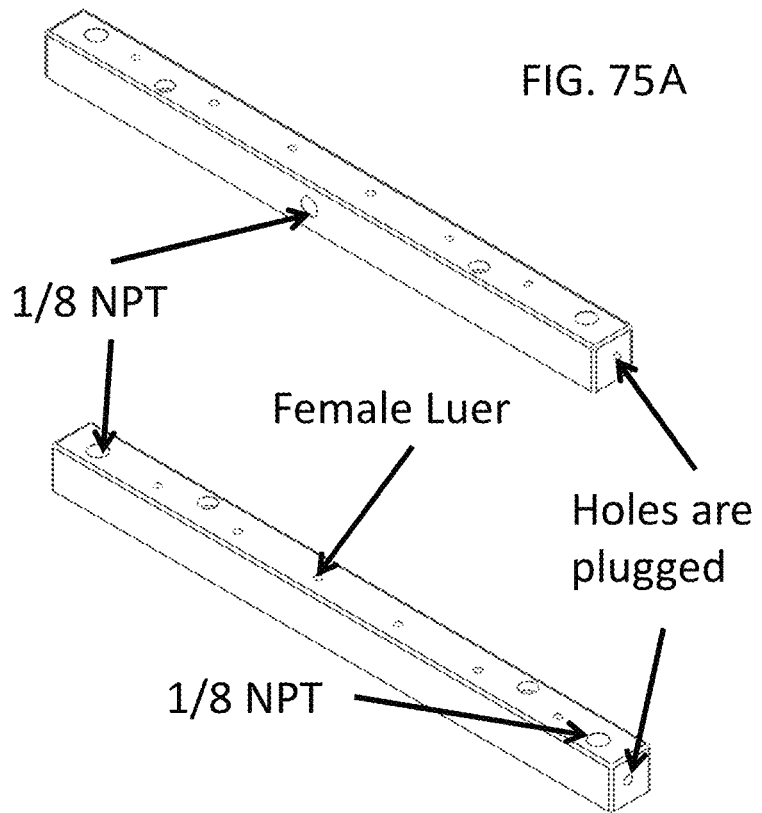
FIGS. 75A and 75B schematics of Stage 1 Manifolds, in accordance with alternative embodiments of the invention.
Figure 75B:
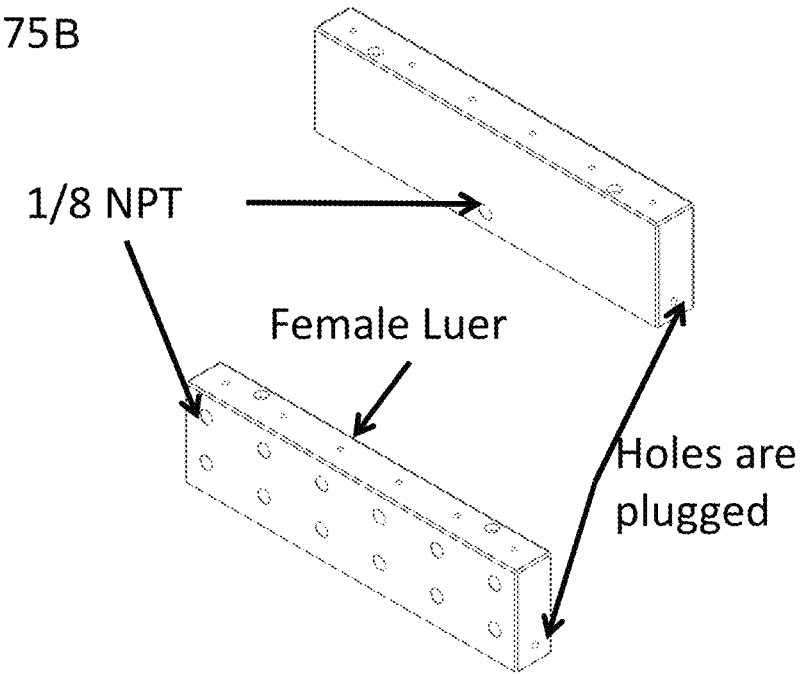

FIGS. 75A and 75B show two Stage 1 Manifold embodiments corresponding to the respective embodiments shown in FIGS. 74A and 74B. Both Stage 1 Manifolds can include one or more female luers for connecting with one or more corresponding assay columns either directly or indirectly via one or more corresponding stop cocks. Both embodiments can include at least one opening on at least one end of the Stage 1 Manifold for reversibly sealing with a sealing device such as, for a non-limiting example, a reversible sealing plug. FIG. 75A includes three openings having, for a non-limiting example, a ⅛ NPT for connecting respectively with a three-way valve fitting, a vacuum gauge and a vacuum relief valve with the Stage 1 Manifold. FIG. 75B shows a similar opening having, for a non-limiting example, a ⅛ NTP for connecting the Stage 1 Manifold with a three-way valve fitting. FIG. 75B includes a plurality of openings each having, as non-limiting example a ⅛ NPT for fluidically connecting the Stage 1 Manifold with a vacuum gauge or an adapter and vacuum regulator and a corresponding assay column. The configuration of FIG. 75B thereby provides individual control of each of the assay columns.

Figure 76:
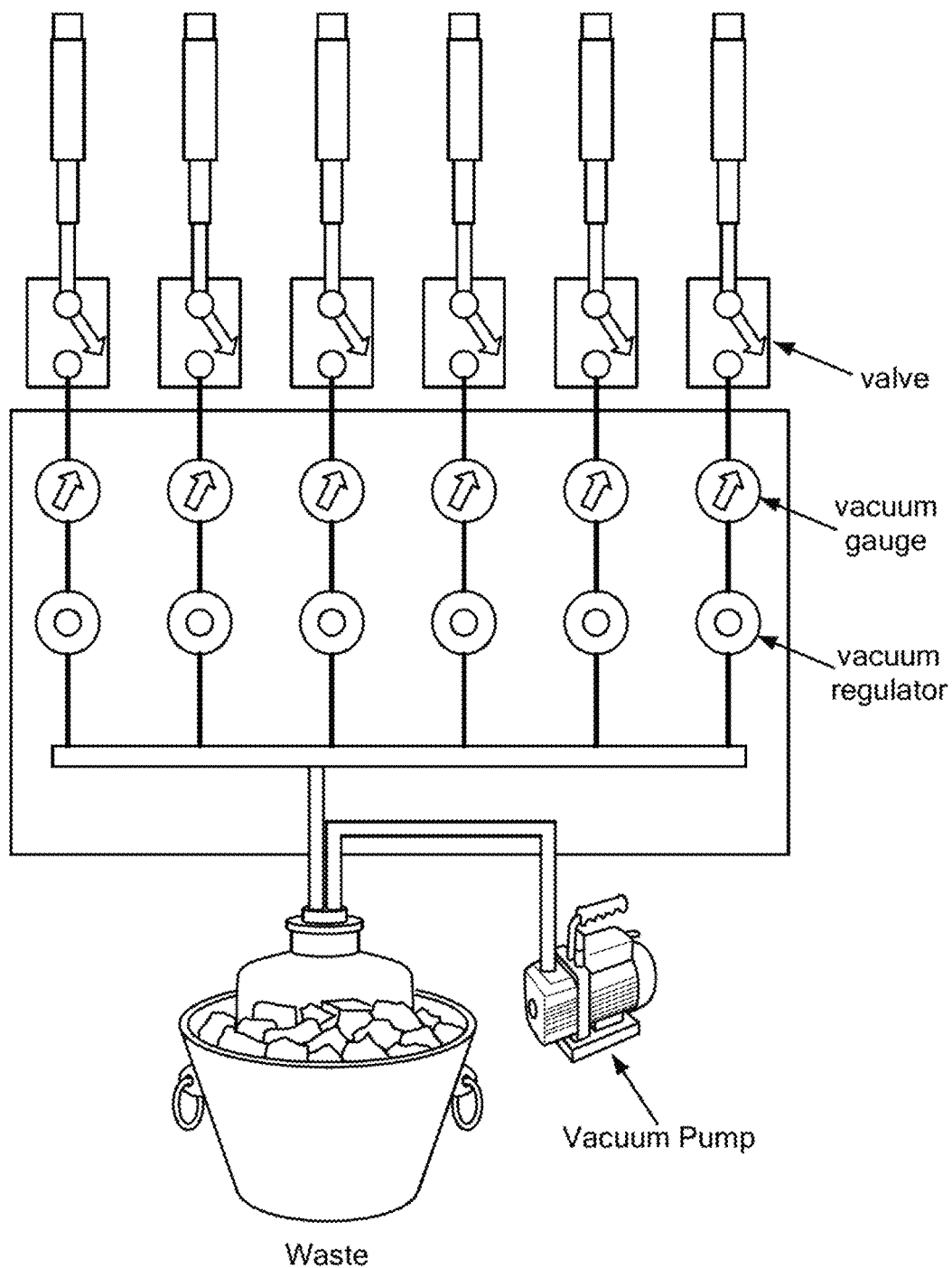
FIG. 76 is a schematic of plumbing lines from a Manifold to a vacuum pump, in accordance with an embodiment of the invention.

FIG. 76 shows a Stage 1 flow diagram including a Stage 1 Manifold having individual vacuum control for each individual assay column as described above and shown in FIGS. 74B and 75B. Fluid from each of the assay columns is drawn by vacuum sequentially in line through a valve, such as, for a non-limiting example, a stopcock, a vacuum gauge, a vacuum regulator into a common exit manifold line where it flows into a waste receptacle which is turn is plumbed to the vacuum pump.

Figure 77A:
FIGS. 77A, 77B and 77C are schematics of stackable assay columns, in accordance with alternative embodiments of the invention.
Figure 77B:
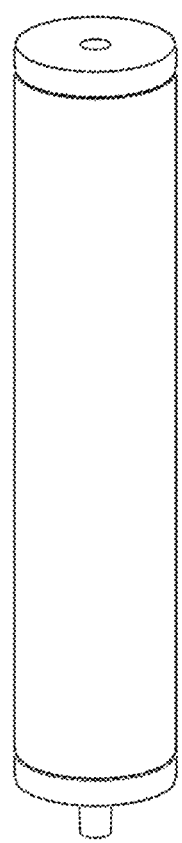
Figure 77C:

FIG. 77 shows different embodiments of the stackable assay columns used in the systems and methods of the invention. Embodiments shown in FIGS. 77A and 77B feature respectively a regularly-sized assay column and a jumbo-sized column. Embodiment shown in FIG. 77C features two stacked columns as described further below.

Figure 78:
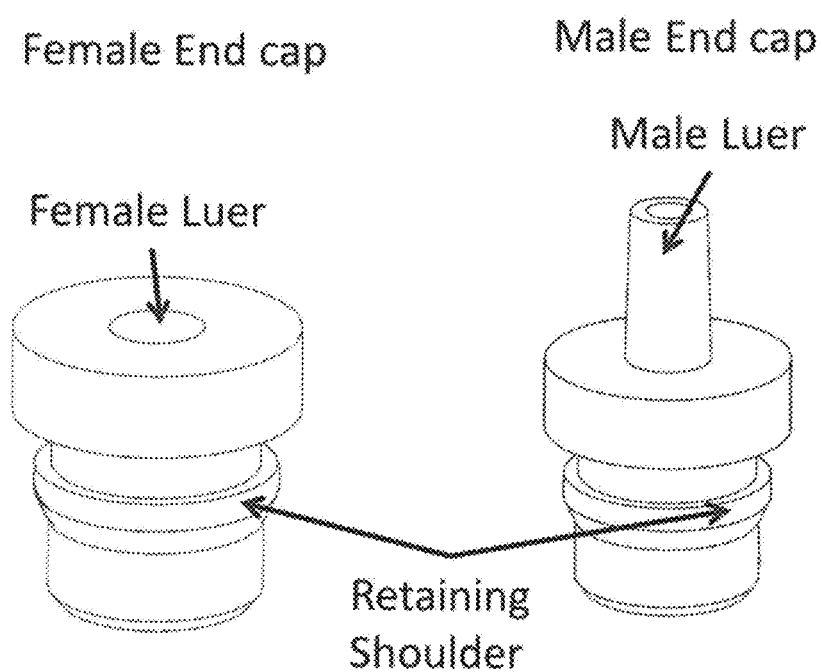
FIG. 78 is a schematic of female and male end caps for a regularly-sized assay column, in accordance with an embodiment of the invention.

FIG. 78 shows female and male end caps for regularly-sized assay columns according to different embodiments of the invention. Both end caps include a retaining shoulder. The female end cap includes a female luer. The male end cap includes a male luer.

Figure 79:
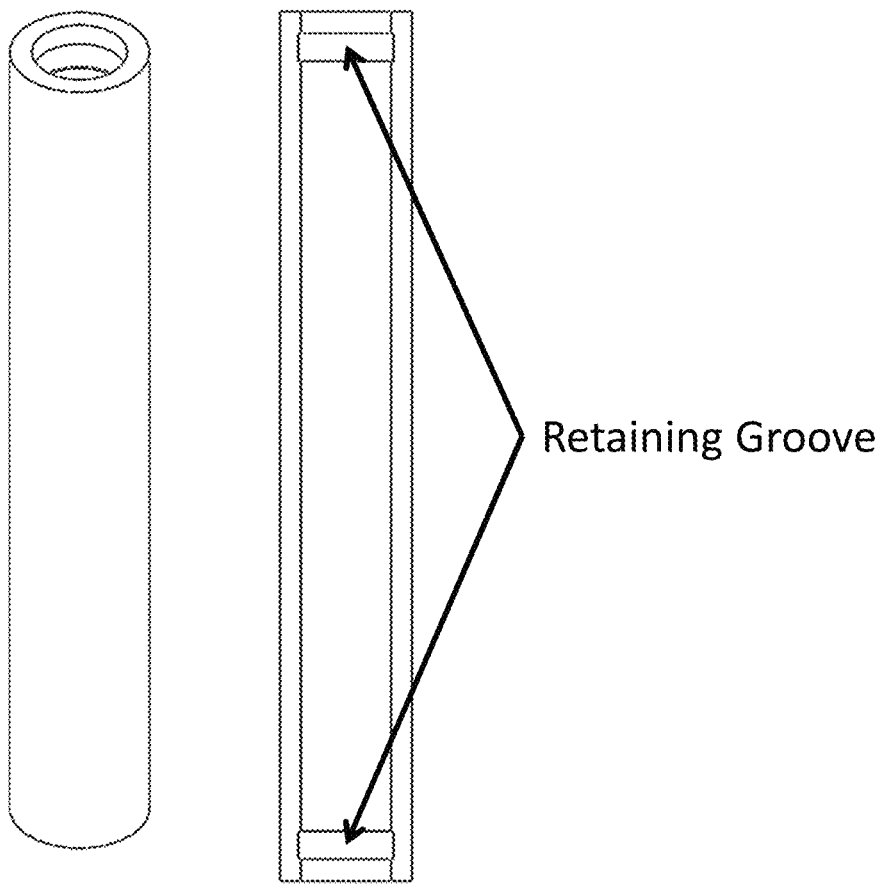
FIG. 79 is a schematic of perspective and sectional views of a stackable regularly-sized assay column including end caps, in accordance with an embodiment of the invention.

FIG. 79 shows a regularly-sized assay column including a retaining groove disposed within at least one and preferably opposing ends of the column. The retaining shoulder of the endcaps featured in FIG. 79 can be positioned to sit within the regaining groove. Notably, the length of the assay columns will vary depending upon the type of assay column.

Figure 81:
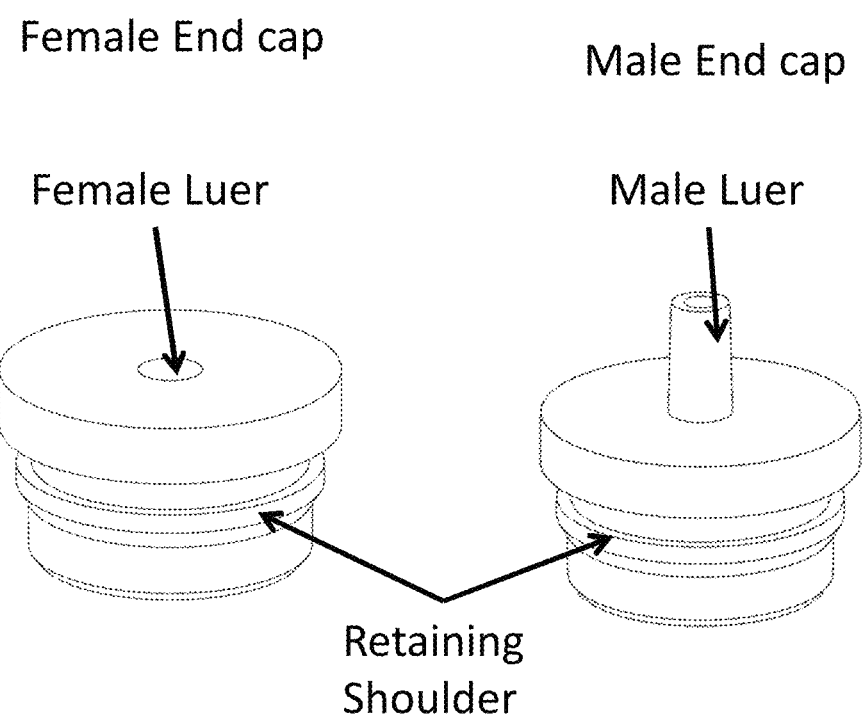
FIG. 81 is a schematic of female and male endcaps for a jumbo-sized assay column, in accordance with an embodiment of the invention.

FIG. 80 shows that when the retaining shoulder featured in FIG. 78 sits within the retaining groove featured in FIG. 79, the combination of the retaining shoulder sitting within the retaining groove holds the end cap in place. The interference between the retaining shoulder and the retaining groove creates a seal. FIG. 81 shows female and male end caps for jumbo-sized assay columns according to different embodiments of the invention. Both end caps include a retaining shoulder. The female end cap includes a female luer. The male end cap includes a male luer.

Figure 82:
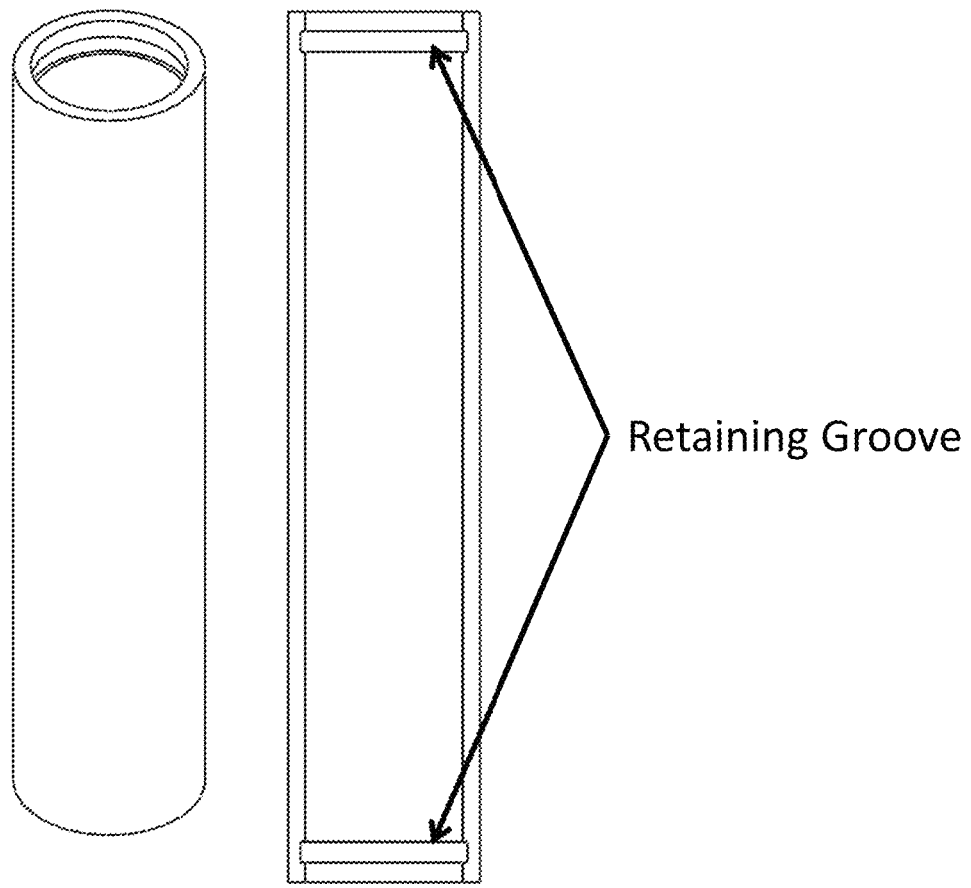
FIG. 82 is a schematic of external perspective and sectional views of a stackable jumbo-sized assay column including end caps, in accordance with an embodiment of the invention.

FIG. 82 shows a jumbo-sized assay column including a retaining groove disposed within at least one and preferably opposing ends of the column. The retaining shoulder of the endcaps featured in FIG. 81 can be positioned to sit within the regaining groove. Notably, the length of the assay columns will vary depending upon the type of assay column.

FIGS. 83A, 83B, and 83C are schematics of sectional views of respective assay column end caps for a jumbo-sized assay column, in accordance with an embodiment of the invention. FIGS. 83A, 83B, and 83C show that when the retaining shoulder featured in FIG. 82 sits within the retaining groove featured in FIG. 79, the combination of the retaining shoulder sitting within the retaining groove holds the end cap in place. The interference between the retaining shoulder and the retaining groove creates a seal. FIG. 84 shows side A and sectional B views of the assay column as shown in previous FIG. 41. FIG. 84 also shows comparatively perspective C and sectional D views of an assay column including opposing end caps each including a retaining shoulder sitting in a retaining groove as described above and shown in, for example, FIGS. 80 and 83.

FIG. 85 shows perspective A and sectional B views, and a perspective, sectional view C of an assay column as shown in the embodiments of previous FIG. 37. FIG. 85 comparatively shows a perspective D and sectional side view E of an assay column including the opposing end caps each including a retaining shoulder sitting in a retaining groove as described above and shown in, for example, FIGS. 80 and 83.

The number of assay columns for inter-connection in the assay column assemblies of the present invention can vary according to the application, as necessary. The assay column assemblies of the present invention can include a number of assay columns for inter-connection in a range of 1 to 20 columns, and preferably in a range of 1 to 10 columns, and more preferably in a range of 1 to 5 columns, and most preferably in a range of 1 to 3 columns.

Figure 86:
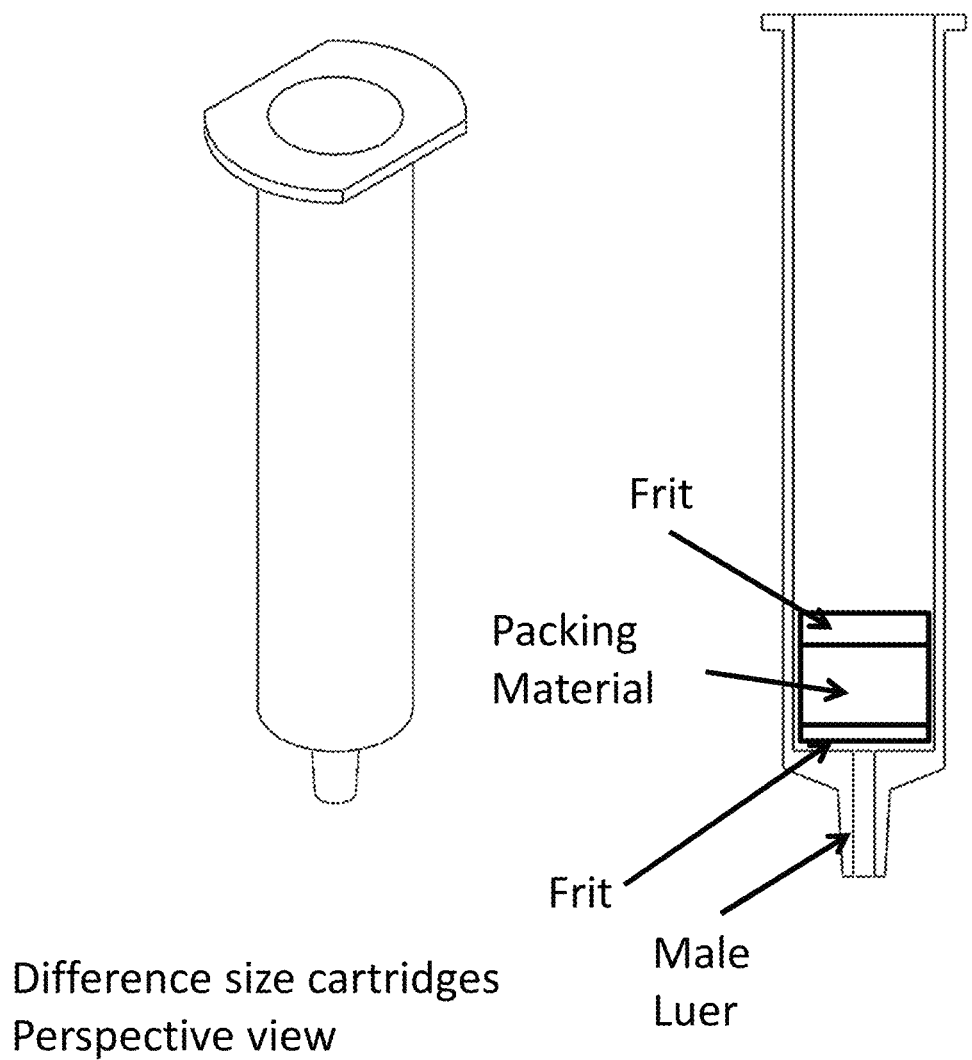
FIG. 86 includes perspective and sectional views of assay cartridges, in accordance with an embodiment of the invention.
Figure 88:
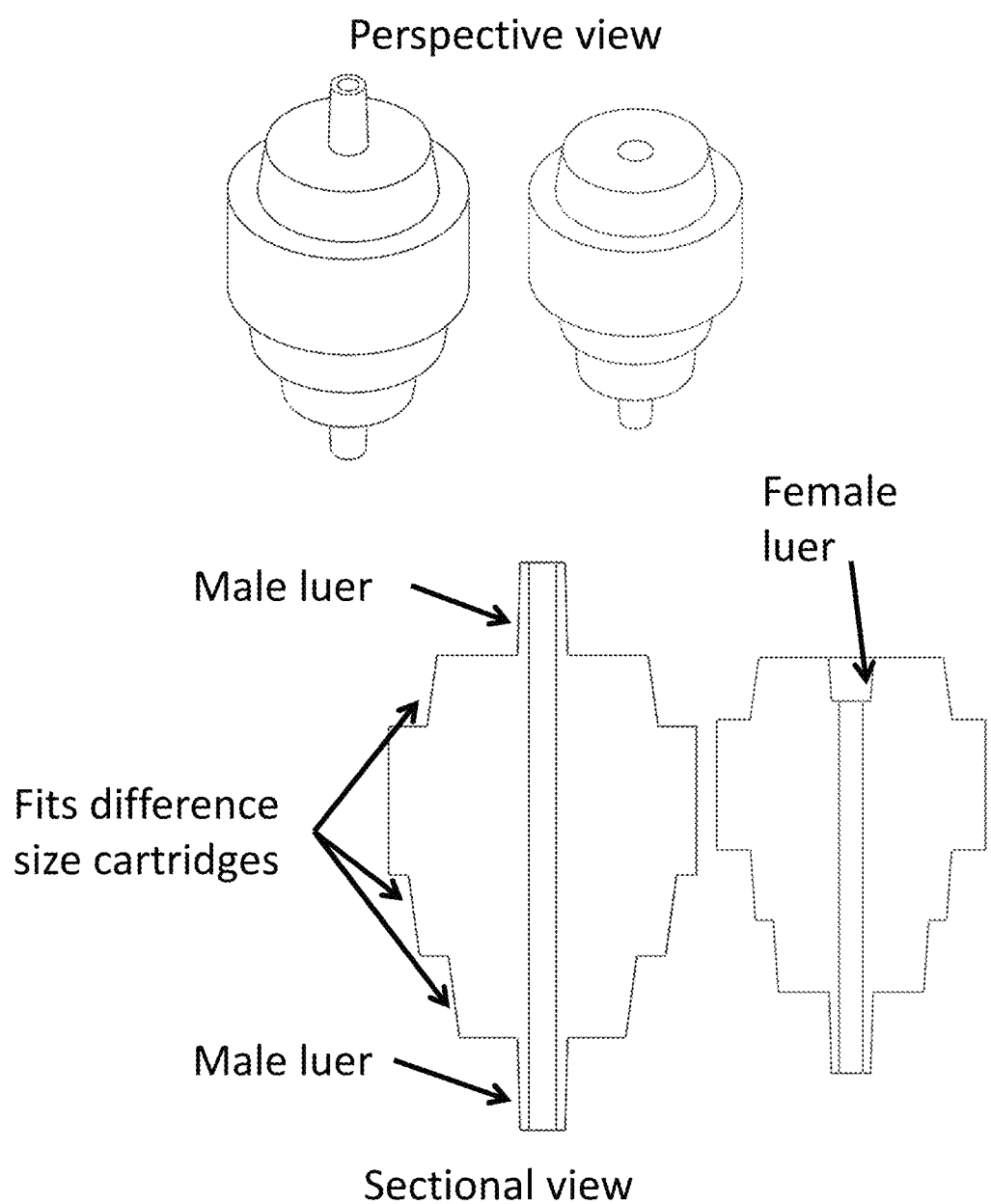
FIG. 88 includes perspective and sectional views of assay cartridge fittings in accordance and embodiments of the invention.
Figure 89:
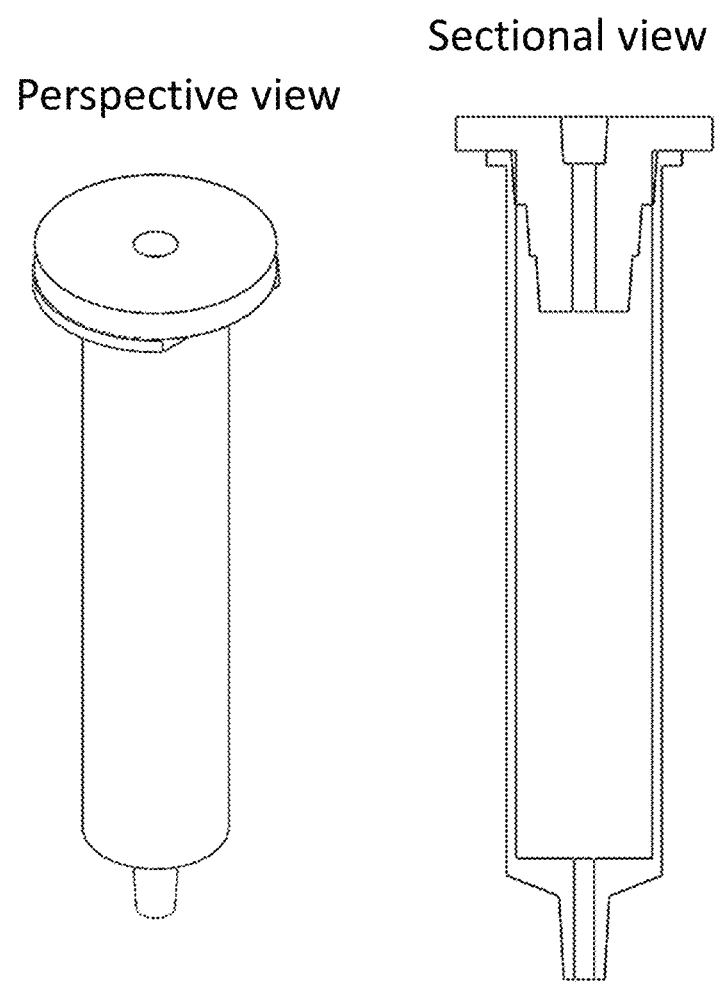
FIG. 89 includes perspective and sectional views of an assay cartridge including a fitting in accordance with an embodiment of the invention.

In alternative embodiments, assay cartridges, as shown in perspective and sectional views of FIG. 86 can be used in lieu of assay columns in the invention. Such assay cartridge can include assay packing material and a frit disposed at each opposing end of the column for holding the packing material. In non-limiting exemplary embodiments, the assay cartridges include a female portion or barrel of a syringe. Such an assay cartridge can include a Luer lock at a first end of the assay cartridge. Such assay cartridges can employ easy connect fittings or adapters as shown in FIGS. 87-91.

It will be apparent to those skilled in the art that modifications to and variations of the disclosed system and methods are possible without departing from the inventive concepts disclosed herein, and therefore the invention should not be viewed as limited except to the full scope and spirit of the invention and claims.

What is claimed is:

1. A vacuum system for purification of and extraction of at least one substance from a liquid sample comprising:
    a rotatable base for rotation between at least a first position and a second position;
    at least one assay column assembly having at least a first assay column and at least one second assay column;
    at least one Stage 1 solvent reservoir and having at least one easy connect fitting configured for fluidic and reversible connection to the first assay column;
    at least one Stage 1 manifold mounted on a Stage 1 portion of the rotatable base and having at least one easy connect fitting configured for fluidic and reversible connection with the second assay column; at least one Stage 2 reservoir and having at least one easy connect fitting configured for fluidic and reversible connection with the second assay column;
    at least one Stage 2 manifold mounted on a Stage 2 portion of the rotatable base and having at least one easy connect fitting configured for fluidic and reversible connection with the second assay column;
    wherein the first assay column has an easy connect fitting disposed at a first entry which is configured for fluidic and reversible connection to the easy connect fitting of the Stage 1 solvent reservoir;
    wherein the first assay column has an easy connect fitting disposed at a first exit opposing the first entry of the first assay column which is configured for fluidic and reversible connection to the second assay column;
    wherein the second assay column has an easy connect fitting disposed at a first entry of the second assay column which is configured for fluidic and reversible selective alternate connection with the first assay column and the Stage 2 manifold;
    wherein the second assay column has an easy connect fitting disposed at a first exit opposing the first entry of the first assay column which configured for fluidic and reversible selective alternate connection with the Stage 1 manifold and the Stage 2 solvent reservoir, and optionally with a third assay column;
    a vacuum pump configured for selective fluidic coupling with the Stage1 manifold and the Stage 2 manifold;
    the vacuum system comprising:
        at least one sample container for containing a liquid sample;
        a drying gas manifold; and
        an easy connect fitting disposed at an opposing second end of at least one of the first, second and third assay columns for fluidic and reversible selective alternate connection to the corresponding at least one fluid sample fluid container, the drying gas manifold and a Stage 2 solvent reservoir.

2. The vacuum system of claim 1, wherein the at least one liquid sample comprises an organic solvent.

3. The vacuum system of claim 1, wherein at least one easy connect fitting comprises a female portion and a male portion at opposing ends of the easy connect fitting.

4. The vacuum system of claim 3, wherein the female portion comprises threaded female portion.

5. The vacuum system of claim 3, wherein the male portion comprises a male luer.

6. The vacuum system of claim 1, wherein at least one easy connect fitting comprises a union adapter including a female portion at opposing ends of the union adapter.

7. The vacuum system of claim 1, wherein at least one of easy connect fitting comprises a male portion machined into a body of a column at a first end of the column, and at least one easy connect fitting comprises a female portion machined into the body of the column at an opposing second end of the column;
    where the column is selected from at least one of the first column, the second assay column and the third assay column.

8. The vacuum system of claim 1 further comprising at least one frit being disposed at the at least one of a first end and an opposing second end of a column and a frit holder adjacent the frit and facing an interior of the column;
    where the column is selected from at least one of the first column, the second assay column and the third assay column.

9. The vacuum system of claim 1, wherein at least one of the first assay column, the second assay column, and the third assay column comprises a column packing material selected for at least one of purification of and extraction from the liquid sample of the at least one substance selected from the group consisting of a pesticide, a chlorinated pesticide, a dioxin, a brominated compound, a polychlorinated biphenyl and a polybrominated diphenyl ether.

10. The vacuum system of claim 1, wherein the Stage 1 manifold comprises a sensor for indicating an at least one of a bubble.

11. The vacuum system of claim 1 further comprising the third assay column;
    wherein the third assay column has an easy connect fitting disposed at a first entry of third assay column which is configured for fluidic and reversible selective alternate connection with the second assay column and the Stage 2 manifold; and
    wherein the third assay column has an easy connect fitting disposed at a first exit of the third assay column opposing the first entry of the third assay column which is configured for fluidic and reversible selective alternate connection with the Stage 1 manifold and the Stage 2 solvent reservoir.

12. The vacuum system of claim 11, wherein at least one male luer is disposed in at least one opposing end of at least one of the first, the second and the third assay columns.

13. The vacuum system of claim 12, where at least one washer is disposed in a groove in a column body adjacent to the at least one male luer on an interior side of the assay column.

14. The vacuum system of claim 13, wherein at least one female luer is disposed in at least one opposing end of at least one of the first, the second and the third assay columns.

15. The vacuum system of claim 14, wherein at least one washer is disposed in a groove disposed adjacent to the female luer on an interior side of the assay column.

16. The vacuum system of claim 1, wherein the Stage 2 solvent reservoir comprises a lid having a vacuum gauge and a vacuum regulator.

17. The vacuum system of claim 1, further comprising at least one washing fluid container for containing a washing fluid for washing at least one of the sample container and the at least one of the first, second and third assay columns selectively before or after extraction.

18. The vacuum system of claim 1, wherein the at least one of the first, second and third assay columns comprises an at least one assay cartridge.

19. The vacuum system of claim 1, wherein the at least one of the first assay columns, the second assay columns and the third assay columns comprises an at least one assay cartridge.

* * * * *